(12) United States Patent
Herr et al.

(10) Patent No.: US 10,307,272 B2
(45) Date of Patent: *Jun. 4, 2019

(54) METHOD FOR USING A MODEL-BASED CONTROLLER FOR A ROBOTIC LEG

(71) Applicant: Massachusetts Institute of Technology, Cambridge, MA (US)

(72) Inventors: Hugh M. Herr, Somerville, MA (US); Hartmut Geyer, Pittsburgh, PA (US); Michael Frederick Eilenberg, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/342,661

(22) Filed: Nov. 3, 2016

(65) Prior Publication Data

US 2017/0049587 A1  Feb. 23, 2017

Related U.S. Application Data

(60) Continuation of application No. 14/520,091, filed on Oct. 21, 2014, now Pat. No. 9,539,117, which is a
(Continued)

(51) Int. Cl.
*A61F 2/64* (2006.01)
*A61F 2/66* (2006.01)
(Continued)

(52) U.S. Cl.
CPC .................. *A61F 2/68* (2013.01); *A61F 2/64* (2013.01); *A61F 2/66* (2013.01); *A61F 5/0123* (2013.01);
(Continued)

(58) Field of Classification Search
CPC .... A61F 2/68; A61F 2/60; A61F 2/605; A61F 2/64; A61F 2/66; A61F 5/0123; A61F 5/0127; A61F 2005/0155; B25J 9/0006
See application file for complete search history.

(56) References Cited

U.S. PATENT DOCUMENTS 2,489,291 A   11/1949   Henschke et al.
2,529,968 A   11/1950   Sartin
(Continued)

FOREIGN PATENT DOCUMENTS

CN   101061984 A   10/2007
CN   101111211 A   1/2008
(Continued)

OTHER PUBLICATIONS

Abbas, J.J. et al., "Neural Network Control of Functional Neuromuscular Stimulation Systems: Computer Simulation Studies," *IEEE Transactions on Biomedical Engineering*, vol. 42, No. 11, Nov. 1995, pp. 1117-1127.
(Continued)

*Primary Examiner* — Marcia L Watkins
(74) *Attorney, Agent, or Firm* — Hamilton, Brook, Smith & Reynolds, P.C.

(57) ABSTRACT

A model-based neuromechanical controller for a robotic limb having at least one joint includes a finite state machine configured to receive feedback data relating to the state of the robotic limb and to determine the state of the robotic limb, a muscle model processor configured to receive state information from the finite state machine and, using muscle geometry and reflex architecture information and a neuromuscular model, to determine at least one desired joint torque or stiffness command to be sent to the robotic limb, and a joint command processor configured to command the biomimetic torques and stiffnesses determined by the muscle model processor at the robotic limb joint. The feedback data
(Continued)

is preferably provided by at least one sensor mounted at each joint of the robotic limb. In a preferred embodiment, the robotic limb is a leg and the finite state machine is synchronized to the leg gait cycle.

19 Claims, 16 Drawing Sheets

Related U.S. Application Data division of application No. 12/698,128, filed on Feb. 1, 2010, now Pat. No. 8,864,846, which is a continuation-in-part of application No. 12/608,627, filed on Oct. 29, 2009, now Pat. No. 8,870,967, which is a continuation of application No. 11/642,993, filed on Dec. 19, 2006, now abandoned, which is a continuation-in-part of application No. 11/600,291, filed on Nov. 15, 2006, now abandoned, which is a continuation-in-part of application No. 11/395,448, filed on Mar. 31, 2006, now abandoned, and a continuation-in-part of application No. 11/499,853, filed on Aug. 4, 2006, now Pat. No. 7,313,463, which is a continuation-in-part of application No. 11/395,448, filed on Mar. 31, 2006, now abandoned, said application No. 12/698,128 is a continuation-in-part of application No. 12/157,727, filed on Jun. 12, 2008, now Pat. No. 8,512,415, which is a continuation-in-part of application No. 11/642,993, filed on Dec. 19, 2006, now abandoned.

(60) Provisional application No. 61/148,545, filed on Jan. 30, 2009, provisional application No. 60/934,223, filed on Jun. 12, 2007, provisional application No. 60/751,680, filed on Dec. 19, 2005, provisional application No. 60/736,929, filed on Nov. 15, 2005, provisional application No. 60/705,651, filed on Aug. 4, 2005, provisional application No. 60/704,517, filed on Aug. 1, 2005, provisional application No. 60/666,876, filed on Mar. 31, 2005.

(51) Int. Cl.
| | |
|---|---|
| *A61F 2/70* | (2006.01) |
| *A61F 2/74* | (2006.01) |
| *A61F 2/76* | (2006.01) |
| *G16H 50/50* | (2018.01) |
| *G06F 19/00* | (2018.01) |
| *B25J 9/16* | (2006.01) |
| *B25J 9/10* | (2006.01) |
| *B25J 9/00* | (2006.01) |
| *A61F 5/01* | (2006.01) |
| *A61F 2/68* | (2006.01) |
| *A61F 2/60* | (2006.01) |

(52) U.S. Cl.
CPC .......... *A61F 5/0127* (2013.01); *B25J 9/0006* (2013.01); *B25J 9/1075* (2013.01); *B25J 9/1633* (2013.01); *G06F 19/00* (2013.01); *G16H 50/50* (2018.01); *A61F 2/605* (2013.01); *A61F 2002/701* (2013.01); *A61F 2002/704* (2013.01); *A61F 2002/705* (2013.01); *A61F 2002/741* (2013.01); *A61F 2002/745* (2013.01); *A61F 2002/747* (2013.01); *A61F 2002/764* (2013.01); *A61F 2002/7625* (2013.01); *A61F 2002/7635* (2013.01); *A61F 2002/7645* (2013.01); *A61F 2005/0155* (2013.01)

(56) References Cited

U.S. PATENT DOCUMENTS

| | | |
|---|---|---|
| 3,016,760 A | 1/1962 | Wrighton et al. |
| 3,098,645 A | 7/1963 | Owens |
| 3,207,497 A | 9/1965 | Schoonover |
| 3,449,769 A | 6/1969 | Mizen |
| 3,844,279 A | 10/1974 | Konvalin |
| 3,871,032 A | 3/1975 | Karas |
| 3,916,450 A | 11/1975 | Minor |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,843,921 A | 7/1989 | Kremer |
| 4,865,376 A | 9/1989 | Leaver et al. |
| 4,872,665 A | 10/1989 | Chareire |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,865,770 A | 2/1999 | Schectman |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |

(56) References Cited

U.S. PATENT DOCUMENTS

| | | |
|---|---|---|
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,314,490 B2 | 1/2008 | Bédard et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,485,152 B2 | 2/2009 | Haynes et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |

(56) References Cited

U.S. PATENT DOCUMENTS

| | | |
|---|---|---|
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| RE42,903 E | 11/2011 | Deffenbaugh et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,202,325 B2 | 6/2012 | Albrecht-Laatsch et al. |
| 8,287,477 B1 | 10/2012 | Herr et al. |
| 8,376,971 B1 | 2/2013 | Herr et al. |
| 8,419,804 B2 | 4/2013 | Herr et al. |
| 8,500,823 B2 | 8/2013 | Herr et al. |
| 8,512,415 B2 | 8/2013 | Herr et al. |
| 8,734,528 B2 | 5/2014 | Herr et al. |
| 8,864,846 B2 | 10/2014 | Herr et al. |
| 8,870,967 B2 | 10/2014 | Herr et al. |
| 9,149,370 B2 | 10/2015 | Herr et al. |
| 9,221,177 B2 | 12/2015 | Herr et al. |
| 9,333,097 B2 | 5/2016 | Herr et al. |
| 9,339,397 B2 | 5/2016 | Herr et al. |
| 9,539,117 B2 | 1/2017 | Herr et al. |
| 9,975,249 B2 | 5/2018 | Herr et al. |
| 10,137,011 B2 | 11/2018 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0181289 A1 | 9/2004 | Bedard et al. |
| 2005/0007834 A1 | 1/2005 | Hidaka |
| 2005/0038525 A1 | 2/2005 | Doddroe et al. |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0192677 A1 | 9/2005 | Ragnarsdottir et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0122711 A1 | 6/2006 | Bedard et al. |
| 2006/0211956 A1 | 9/2006 | Sankai |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0162152 A1 | 7/2007 | Herr et al. |
| 2007/0267791 A1 | 11/2007 | Hollander et al. |
| 2008/0114272 A1 | 5/2008 | Herr et al. |
| 2008/0155444 A1 | 6/2008 | Pannese et al. |
| 2008/0169729 A1 | 7/2008 | Asai |
| 2009/0030530 A1 | 1/2009 | Martin |
| 2009/0222105 A1 | 9/2009 | Clausen |
| 2009/0265018 A1 | 10/2009 | Goldfarb et al. |
| 2010/0113988 A1 | 5/2010 | Matsuoka et al. |
| 2010/0241242 A1 | 9/2010 | Herr et al. |
| 2010/0256537 A1 | 10/2010 | Menga |
| 2010/0280629 A1 | 11/2010 | Jung et al. |
| 2010/0324699 A1 | 12/2010 | Herr et al. |
| 2011/0040216 A1 | 2/2011 | Herr et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2011/0307079 A1 | 12/2011 | Oweiss |
| 2012/0136459 A1 | 5/2012 | Herr et al. |
| 2012/0209405 A1 | 8/2012 | Herr et al. |
| 2012/0271433 A1 | 10/2012 | Galea et al. |
| 2013/0110256 A1 | 5/2013 | Herr et al. |
| 2013/0158444 A1 | 6/2013 | Herr et al. |
| 2013/0197318 A1 | 8/2013 | Herr |
| 2013/0310979 A1 | 11/2013 | Herr et al. |

(56) References Cited

U.S. PATENT DOCUMENTS

| | | |
|---|---|---|
| 2014/0046455 A1 | 2/2014 | Herr et al. |
| 2014/0088729 A1 | 3/2014 | Herr et al. |
| 2014/0257519 A1 | 9/2014 | Herr et al. |
| 2015/0051710 A1 | 2/2015 | Herr et al. |
| 2016/0207201 A1 | 7/2016 | Herr et al. |
| 2016/0228265 A1 | 8/2016 | Herr et al. |
| 2016/0338857 A1 | 11/2016 | Herr et al. |
| 2017/0049587 A1 | 2/2017 | Herr et al. |

FOREIGN PATENT DOCUMENTS

| | | |
|---|---|---|
| EP | 1169982 | 1/2002 |
| EP | 1393866 | 3/2004 |
| JP | 2008-87143 A | 4/2008 |
| WO | WO 2001/054630 A1 | 8/2001 |
| WO | WO 2003/005934 A2 | 1/2003 |
| WO | WO 2003/03068453 | 8/2003 |
| WO | WO 2004/017872 A1 | 3/2004 |
| WO | WO 2004/019832 A1 | 3/2004 |
| WO | WO 2010/027968 A2 | 3/2010 |
| WO | WO 2010/088616 | 8/2010 |
| WO | WO 2010/088635 A1 | 8/2010 |

OTHER PUBLICATIONS

Abul-Haj, C.J. et al., "Functional Assessment of Control Systems for Cybernetic Elbow Prostheses-Part II: Application of the Technique," IEEE Transactions on Biomedical Engineering, vol. 17, No. 11, Nov. 1990, pp. 1037-1047.
Aeyels, et al., "An Emg-Based finite state approach for microcomputer-controlled above-knee prosthesis," IEEE, pp. 1315-1316 (1995).
af Klint, R., et al., "Sudden Drop in Ground Support Produces Force-Related Unload Response in Human Overground Walking," J. Neurophysiol., 101:1705-1712 (2009).
af Klint, R., et al., "Within-Step Modulation of Leg Muscle Activity by Afferent Feedback in Human Walking," The Journal of Physiology, 586(19):4643-4648 (2008).
Akazawa, K. et al., "Biomimetic EMG-Prosthesis-Hand, 18th Annual International Conference of the IEEE Engineering in Medicine and Biology Society," Amsterdam 1996, pp. 535 and 536.
Aminian, K. et al., "Estimation of Speed and Incline of Walking Using Neural Network," IEEE Transactions of Instrumentation and Measurement, 44(3): 743-746 (1995).
Anderson, F.C. et al., "Dynamic Optimization of Human Walking," Journal of Biomechanical Engineering, 123: 381-390 (2001).
Andrews, B.J. et al., "Hybrid FES Orthosis Incorporating Closed Loop Control and Sensory Feedback," J. Biomed. Eng., 10: 189-195 (1988).
Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.
Au, S. et al., "Powered Ankle-Foot Prosthesis for the Improvement of Amputee Ambulation", Proceedings of the 29th Annual International Conference of the IEEE Eng. Med. Biol. Soc., Cite Internationale, Lyon France, Aug. 23-26, 2007, 2007:3020-6.
Au, S. et al., "Powered Ankle-Foot Prosthesis to Assist Level-Ground and Stair-Descent Gaits," Neural Networks, 21: 654-666 (2008).
Au, S.K. et al., "An Ankle-Foot Emulation System for the Study of Human Walking Biomechanics," Proceedings of the 2006 IEEE International Conference on Robotics and Automation, Orlando, FLA, May 2006, pp. 2939-2945.
Au, S.K. et al., "An EMG-Position Controlled System for an Active Ankle-Foot Prosthesis: An Initial Experimental Study," Proceedings of the 2005 IEEE 9th International Conference on Rehabilitation Robotics, Chicago, IL., pp. 375-379.
Au, S.K. et al., "Biomechanical Design of a Powered Ankle-Foot Prosthesis," Proceedings of the 2007 IEEE 10th International Conference on Rehabilitation Robotics, Noordwijk, The Netherlands, Jun. 12-15, 2007 pp. 298-303.
Au, S.K. et al., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.
Au, S.K. et al., "Powered Ankle—Foot Prosthesis Improves Walking Metabolic Economy," IEEE Transactions on Robotics, 25(1): 51-66 (2009).
Au, et al., "Powered Ankle-Foot Prosthesis: The Importance of Series and Parallel Motor Elasticity," IEEE Robotics & Automation Magazine, pp. 52-59, Sep. 2008.
Au, S. K.-W., et al., "Powered Ankle-Foot Prosthesis for the Improvement of Amputee Walking Economy." Doctoral dissertation, Massachusetts Institute of Technology (2007).
Barth, D.G. et al., "Gait Analysis and Energy Cost of Below-Knee Amputees Wearing Six Different Prosthetic Feet," JPO, 4(2): 63 (1992).
Baten, Chris T.M. et al., "Inertial Sensing in Ambulatory Back Load Estimation," paper presented at the 18th Annual International Conference of the IEEE Engineering in Medicine and Biology Society, Amsterdam, 1996, pp. 497-498.
Bateni, H. et al., "Kinematic and Kinetic Variations of Below-Knee Amputee Gait," JPO, 14(1):112 (2002).
Blaya, J. et al., "Active Ankle Foot Orthoses (AAFO)," Artificial Intelligence Laboratory, Massachusetts Institute of Technology, Cambridge, MA, pp. 275-277 (No date given).
Blaya, J.A. et al., "Active Ankle Foot Orthoses (AAFO)," Retrieved from: http://www.ai,mit.edu. Artificial Intelligence Laboratory, Massachusetts Institute of Technology, Cambridge, Massachusetts, pp. 251-253 (No date given).
Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages (No date given).
Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).
Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts, 88 pages (Feb. 2003).
Blickhan, R., "The Spring-Mass Model for Running and Hopping," J. Biomechanics, 22(11 /12): 1217-1227 (1989).
Bortz, J.E. "A New Mathematical Formulation for Strapdown Inertial Navigation," IEEE Transactions on Aerospace and Electronic Systems, AES-7(1): 61-66 (1971).
Bouten, C.V. et al., "Assessment of Energy Expenditure for Physical Activity Using a Triaxial Accelerometer," Medicine and Science in Sports and Exercise, pp. 1516-1523 (1994).
Brockway, J.M., "Derivation of Formulae Used to Calculate Energy Expenditure in Man," Human Nutrition: Clinical Nutrition (1987), 41C, pp. 463-471.
Brown, T. Graham, "On the Nature of the Fundamental Activity of the Nervous Centres; Together with an Analysis of the Conditioning of Rhythmic Activity in Progression, and a Theory of the Evolution of Function in the Nervous System," pp. 24-46 (No date given).
Cavagna, G.A., et al., "The Sources of External Work in Level Walking and Running," J. Physiol. 262:639-657 (1976).
Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.
Clancy, E.A., et al., "Sampling, noise-reduction and amplitude estimation issues in surface electromyography," Journal of Electromyography and Kinesiology:, 12(1):1-16 (Feb. 2002) PMID: 11804807.
Colborne, G.R., et al., "Analysis of mechanical and metabolic factors in the gait of congenital below knee amputees," Am. J. Phys. Med. Rehabil., vol. 92, pp. 272-278, Oct. 1992.

(56) References Cited

OTHER PUBLICATIONS

Colgate, James Edward, "The Control of Dynamically Interacting Systems," Massachusetts Institute of Technology, Aug. 1988, pp. 1-15.
Collins, S.H. et al., "Controlled Energy Storage and Return Prosthesis Reduces Metabolic Cost of Walking," ISB XXth Congress-ASB 29$^{th}$ Annual Meeting, Jul. 31-Aug. 5, Cleveland, Ohio, pp. 804 (No date given).
Collins, S.H. et al., Supporting Online Material for "Efficient Bipedal Robots Based on Passive-Dynamic Walkers," Mechanical Engineering, University of Michigan, Ann Arbor, MI Feb. 11, 2005, pp. 1-8.
Collins, S.H., et al., "A Bipedal Walking Robot with Efficient and Human-Like Gait," 2005 IEEE, Int'l Conference on Robotics and Automation, Barcelona, Spain, pp. 1983-1988, (Apr. 2005).
Cornell University 2009 Disability Status Report, United States (2009).
Crago, P.E. et al., "New Control Strategies for Neuroprosthetic Systems," *Journal of Rehabilitation Research and Development*, vol. 33, No. 2, Apr. 1996, pp. 158-172.
Cronin, N.J., et al., "Mechanical and Neural Stretch Responses of the Human Soleus Muscle at Different Walking Speed," *J. Physiol.*, (2009).
Daley, M.A. et al., "Running Stability is Enhanced by a Proximo-Distal Gradient in Joint Neuromechanical Control," *The Journal of Experimental Biology*, vol. 210, pp. 383-394 (Feb. 2007).
Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).
Davids, J.R., "Book Reviews" *Journal of Pediatric Orthopedics* 12, pp. 815 (1992).
Deb, K., "Multi-Objective Optimization Using Evolutionary Algorithms," *Wiley* (2001).
Deb, K., et al., "A Hybrid Multi-Objective Evolutionary Approach to Engineering Shape Design," *International Conference on Evolutionary Multi-Criterion Optimization*, EMO-2001, pp. 385-399 (2001).
Deb, K., et al., "Controlled Elitist Non-Dominated Sorting Genetic Algorithms for Better Convergence," *International Conference on Evolutionary Multi-Criterion Optimization, EMO 2001*; pp. 67-81 (2001).
Delp, S., "Surgery Simulation: A Computer Graphics System to Analyze and Design Musculoskeletal Reconstructions of the Lower Limb," *PhD Thesis*, Stanford, (1990).
Delp, S., et al., "An Interactive Graphics-based Model of the Lower Extremity Orthopaedic Surgical Procedures," *IEEE Transactions on Biomedical Engineering*, 37(8):757-767 (1990).
Dietz, V. "Proprioception and Locomotor Disorders," *Nature Reviews*, vol. 3, pp. 781-790 (Oct. 2002).
Dietz, V. "Spinal Cord Pattern Generators for Locomotion," *Clinical Neurophysiology*, vol. 114, Issue 8, pp. 1-12 (Aug. 2003).
Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.
Doke, J. et al., "Mechanics and Energetics of Swinging the Human Leg," *The Journal of Experimental Biology*, vol. 208, pp. 439-445 (2005).
Dollar, A.M. et al., "Lower Extremity Exoskeletons and Active Orthoses: Challenges and State-of-the-Art," *IEEE Transactions on Robotics*, vol. 24, No. 1, Feb. 2008, pp. 1-15.
Donelan, J.M. et al., "Force Regulation of Ankle Extensor Muscle Activity in Freely Walking Cats," *Journal of Neurophysiology*, vol. 101, pp. 360-371 (2009).
Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).
Donelan, J.M. et al., "Simultaneous Positive and Negative External Mechanical Work in Human Walking," *Journal of Biomechanics*, vol. 35, 2002, pp. 117-124 (2002).
Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.
Drake, C., "Ankle & Foot Splints or Orthoses (AFOs)," HemiHelp Information Sheet, pp. 1-6, last revision Dec. 2011.
Drake, C., "Foot & Ankle Splints or Orthoses," HemiHelp Information Sheet No. 13, pp. 1-5, last updated Jun. 2009.
Eilenberg, M.F. "A Neuromuscular-Model Based Control Strategy for Powered Ankle-Foot Prostheses," Massachusetts Institute of Technology, pp. 1-90 (Jul. 20, 2010).
Eilenberg, M.F. et al., Control of a Powered Ankle-Foot Prosthesis Based on a Neuromuscular Model, "*IEEE Transactions on Neural Systems & Rehabilitation Eng.*", vol. 18(2):164-173 (2010).
Ekeberg, Ö et al., "Computer Simulation of Stepping in the Hind Legs of the Cat: An Examination of Mechanisms Regulating the Stance-to-Swing Transition," *J Neurophysical*, vol. 94, pp. 4256-4268 (2005).
Ekeberg, Ö et al., "Simulations of Neuromuscular Control in Lamprey Swimming," The Royal Society, *Phil. Trans. R. Soc. Land*, vol. 354, pp. 895-902 (1999).
Endo, K. et al., "A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.
Endo, K., et al., "A Model of Muscle-Tendon Function in Human Walking," In Proc. of ICRA, pp. 1909-1915 (2009).
Eppinger, S.D. et al., "Three Dynamic Problems in Robot Force Control," *IEEE Transactions on Robotics and Automation*, vol. 8, No. 6, pp. 772-778 (Dec. 1992).
Esquenazi, M.D., A., et al., "Rehabilitation After Amputation," *J Am Podiatr Med Assoc* vol. 91, No. 1, pp. 13-22 (Jan. 2001).
Farley, C.T. et al., "Energetics of Walking and Running: Insights From Simulated Reduced-Gravity Experiments," *J. Appl. Physiol.* 73(6):2709-2712 (1992).
Farry, K.A. et al., "Myoelectric Teleoperation of a Complex Robotic Hand," *IEEE Transactions on Robotics and Automation*, vol. 12, No. 5, pp. 775-778 (Oct. 1996).
Featherstone, R., "Robot Dynamics Algorithms," Edinburgh University, pp. 1-173 (1987).
Ferris, D.P., et al., "Robotic lower limb exoskeletons using proportional myoelectric control," pp. 2119-2124 (Sep. 2009).
Fite, K. et al., "Design and Control of an Electrically Powered Knee Prosthesis," Proceedings of the IEEE 10$^{th}$ International Conference on Rehabilitation Robotics, Jun. 12-15, 2007, The Netherlands, pp. 902-905.
Flowers, W.C., "A Man-Interactive Simulator System for Above-Knee Prosthetics Studies," MIT, pp. 1-94 (1972).
Fod, A. et al., "Automated Derivation of Primitives for Movement Classification," *Autonomous Robots*, vol. 12, No. 1, pp. 39-54 (Jan. 2002).
Frigon, A. et al., "Experiments and Models of Sensorimotor Interactions During Locomotion," *Biological Cybernetics*, vol. 95, pp. 606-627 (2006).
Fujita et al., "Joint Angle Control with Command Filter for Human Ankle Movement Using Functional Electrical Stimulation," IEEE Ninth Annual Conference of the Engineering in Medicine and Biology Society (1987).
Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).
Fukunaga, T., et al., "In Vivo Behavior of Human Muscle Tendon During Walking," *Proc. Biol. Sci.*, 268: 229-233 (2001).
Gates, D.H. Thesis: "Characterizing Ankle Function During Stair Ascent, Descent, and Level Walking for Ankle Prosthesis and Orthosis Design," Boston University, pp. 1-84 (2004).
Gates, D.H., et al., "Characterization of ankle function during stair ambulation," *Conference Proceedings: Annual International Conference of the IEEE Engineering in Medicine and Biology Society*.

(56) References Cited

OTHER PUBLICATIONS

*IEEE Engineering in Medicine and Biology Society. Conference*, 6: 4248-4251, (2004). PMID: 17271242.

Gerritsen, K.G.M. et al., "Direct Dynamics Simulation of the Impact Phase in Heel-Toe Running," *J. Biomechanics*, vol. 28, No. 6, pp. 661-668 (1995).

Geyer, H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).

Geyer, H. et al., "Positive Force Feedback in Bouncing Gaits?," *Proc. R Society. Lond. B*, 270, pp. 2173-2183 (2003).

Geyer, H. et al., "Compliant Leg Behavior Explains Basic Dynamics of Walking and Running," *Proc. R. Soc. B*, vol. 273, pp. 2861-2867 (2006).

Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).

Giszter, S., et al., "Convergent Force Fields Organized in the Frog's Spinal Cord," *Journal of Neuroscience*, 13(2): 467-491 (1993).

Godha, S. et al., "Integrated GPS/INS System for Pedestrian Navigation in a Signal Degraded Environment," ION GNSS, Fort Worth, TX, Sep. 26-29, 2006, pp. 1-14.

Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.

Goswami, A., "Postural Stability of Biped Robots and the Foot-Rotation Indicator (FRI) Point," *The International Journal of Robotics Research*, vol. 18, No. 6, pp. 523-533 (Jun. 1999).

Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).

Gregoire, L. et al., "Role of Mono- and Biarticular Muscles in Explosive Movements," *International Journal of Sports Medicine*, vol. 5, No. 6, pp. 299-352 (Dec. 1984).

Grey, M.J., et al., "Positive Force Feedback in Human Walking," *J. of Physiology*, 581(1):99-105 (2007).

Grieve, D., "Prediction of Gastrocnemius Length from Knee and Ankle Joint Posture," *International Series of Biomechanics*, 2A:405-412 (1978).

Grillner, S. and Zangger, P., "On the Central Generation of Locomotion in the Low Spinal Cat," *Experimental Brain Research*, 34: 241-261 (1979).

Grimes, D.L., "An Active Multi-Mode Above-Knee Prosthesis Controller," unpublished doctoral dissertation, Massachusetts Institute of Technology (1979).

Gu, W.J., "The Regulation of Angular Momentum During Human Walking," unpublished doctoral dissertation, Massachusetts Institute of Technology (2003).

Gunther, M. et al., "Human Leg Design: Optimal Axial Alignment Under Constraints," *J. Math. Biol.*, 48: 623-646 (2004).

Gunther, M., and Ruder, H., "Synthesis of Two-Dimensional Human Walking: a test of the λ-model," *Biol. Cybern.*, 89: 89-106 (2003).

Haimes, Y.Y., et al., "On a Bicriterion Formulation of the Problems of Integrated System Identification and System Optimization," *IEEE Transactions on Systems, Man and Cybernetics*, 1(3):296-297 (1971).

Hanafusa, et al., "A Robot Hand with Elastic Fingers and Its Application to Assembly Process," pp. 337-359, Robot Motion, Brady, et al., MIT Press, Cambridge, MA, 1982.

Hansen, A.H., et al., "The Human Ankle During Walking: Implications for Design of Biomimetic Ankle Prostheses," *Journal of Biomechanics*, 37: 1467-1474 (2004).

Hargrove, L.J., et al., "Real-Time myoelectric control of knee and ankle motions for transfemoral amputees," *JAMA: The Journal of the American Medical Association*, 305(15):1542-1544 (Apr. 2011).

Hargrove, L.J., et al., "Toward the development of a neural interface for lower limb prosthesis control," *Conference Proceedings: Annual International Conference of the IEEE Engineering in Medicine and Biology Society. IEEE Engineering in Medicine and Biology Society. Conference*, 2009:2111-2114, (2009). PMID: 19964782.

Hase, K., et al., "Computer Simulation Study of Human Locomotion with a Three-Dimensional Entire-Body Neuro-Musculo-Skeletal Model, Acquisition of Normal Walking," *JSME Int. J., Series C*, 45(4):1040-1050 (2002).

Hayes, W.C., et al., "Leg Motion Analysis During Gait by Multiaxial Accelerometry: Theoretical Foundations and Preliminary Validations," *Journal of Biomechanical Engineering*, 105: 283-289 (1983).

Heglund, N. et al., "A Simple Design for a Force-Plate to Measure Ground Reaction Forces," *J. Exp. Biol.*, 93: 333-338 (1981).

Herbert, R.D., et al., "Change in Length of Relaxed Muscle Fascicles and Tendons with Knee and Ankle Movement in Human," *J. of Physiology*, 539:637-645 (2002).

Herr, H.M. et al., "A Model of Scale Effects in mammalian Quadrupedal Running," *The Journal of Experimental Biology*, 205: 959-967 (2002).

Herr, H.M., and McMahon, T.A., "A Trotting Horse Model," *The International Journal of Robotics Research*, 19: 566-581 (2000).

Herr, H.M., et al., "Bionic Ankle-Foot Prosthesis Normalizes Walking Gait for Persons with Leg Amputation," *Proceedings of the Royal Society, Series B, Biological Sciences*, (2011).

Herr, H.M., and Popovic, M., "Angular Momentum in Human Walking," *The Journal of Experimental Biology*, 211: 467-481 (2008).

Herr, H.M., and Wilkenfeld, A., "User-adaptive Control of a Magnetorheological Prosthetic Knee," *Industrial Robot: An International Journal*, 30(1): 42-55 (2003).

Herr, Hugh et al. "New Horizons for Orthotic and Prosthetic Technology: Artificial Muscle for Ambulation," The MIT Media Laboratory, pp. 1-9, 2004.

Heyn, A., et al., "The Kinematics of the Swing Phase Obtained From Accelerometer and Gyroscope Measurements," paper presented at the $18^{th}$ Annual International Conference of the IEEE Engineering in Medicine and Biology Society, Amsterdam (1996)

Hill, A.V., "The Heat of Shortening and the Dynamic Constants of Muscle," *Proc. R. Soc. Lond.*, 126: 136-195 (1938).

Hirai, K., et al., "The Development of Honda Humanoid Robot," paper presented at the 1998 IEEE International Conference on Robotics & Automation (1998).

Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, Las Vegas, Nevada, pp. 1587-1596 (Sep. 2007).

Hof, A.L., et al., "Calf Muscle Moment, Work and Efficiency in Level Walking: Role of Series Elasticity," *J. Biochem.*, 16: 523-537 (1983).

Hofbaur, M.W., and Williams, B.C., "Mode Estimation of Probabilistic Hybrid Systems," MIT Space Systems and Artificial Intelligence Laboratories and Graz University of Technology, Department of Automatic Control (No date given).

Hofbaur, M.W., et al., "Hybrid Diagnosis with Unknown Behavioral Modes," Proceedings of the $13^{th}$ International Workshop on Principles of Diagnosis (DX02) (2002).

Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).

Hofmann, A.G., "Robust Execution of Bipedal Walking Tasks From Biomechanical Principles," unpublished doctoral dissertation for Massachusetts Institute of Technology (2006).

Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).

Hogan, N., "Impedance Control: An Approach to Manipulation: Part II—Implementation," *Journal of Dynamic Systems, Measurement and Control*, 107: 8-16 (1985).

(56) References Cited

OTHER PUBLICATIONS

Hogan, N., "A Review of the Methods of Processing EMG for Use As a Proportional Control Signal," *Biomedical Engineering*, 11(3): 81-86 (1976).
Hogan, N., "Impedance Control: An Approach to Manipulation: Part III—Application," *Journal of Dynamics Systems, Measurement and Control*, 107: 17-24 (1985).
Hogan, N., "Impedance Control: An Approach to Manipulation: Part I—Theory," Journal of Dynamic Systems, Measurement, and Control, 107: 1-7 (1985).
Hogan, N., and Buerger, S.P., "Impedance and Interaction Control, Robots and Automation Handbook, Chapter 19, © 2005 by CRC Press LLC, 24 pgs.".
Hogan, N. et al., "Myoelectric signal processing: Optimal estimation applied to electromyography—part i: Derivation of the optimal myoprocessor," *Biomedical Engineering, IEEE Transactions on*, BME-27(7):382-395 (Jul. 1980).
Holgate, M.A., et al., "The Sparky (Spring Ankle With Regenerative Kinetics) Project: Choosing a DC Motor Based Actuation Method," Proceedings of the 2nd Biennial IEEE-EMBS International Conf on Biomedical Robotics and Biomechatronics, Scottsdale, AZ, pp. 163-168, Oct. 19-22, 2008.
Hollander, K.W. et al., "Adjustable Robotic Tendon using a 'Jack Spring'®," Proceedings of the 2005 IEEE, $9^{th}$ International Conference on Rehabilitation Robotics, Jun. 28-Jul. 1, 2005, Chicago, IL, USA, pp. 113-118.
Howard, R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.
Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).
Huang, Q. et al., "Planning Walking Patterns for a Biped Robot," *IEEE Transactions on Robotics and Automation*,17(3): 280-289 (Jun. 2001).
Hultborn, H., "Spinal reflexes, mechanisms and concepts: From Eccles to Lundberg and beyond," *Progress in Neurobiology*,78: 215-232 (2006).
Ijspeert, A.J. et al., "From swimming to walking with a salamander robot driven by a spinal cord model," pp. 1-5, *Science*, 315(5817): 1416-20 (2007).
Ijspeert, A.J., "Central pattern generators for locomotion control in animals and robots: a review," *Preprint of Neural Networks*, vol. 21, No. 4, pp. 642-653 (2008).
International Preliminary Report on Patentability for International Application No. PCT/US2010/047279; dated Mar. 15, 2012.
International Search Report and Written Opinion for corresponding International Application No. PCT/US2010/022783, "Model-Based Neuromechanical Controller for a Robotic Leg" dated May 4, 2010.
International Search Report and Written Opinion for International Application No. PCT/US2009/055600, dated Apr. 29, 2010 (23 pages).
International Search Report and Written Opinion for International Application No. PCT/US2010/047279, dated Jan. 19, 2011 (11 pages).
International Search Report and Written Opinion for International Application No. PCT/US2011/031105, dated Oct. 11, 2011 (16 pages).
Ishikawa, M., et al., "Muscle-Tendon Interaction and Elastic Energy Usage in Human Walking," *J. Appl. Physiol.*, 99:603-608 (2005).
Ivashko, D.G. et al., "Modeling the spinal cord neural circuitry controlling cat hindlimb movement during locomotion," *Neurocomputing*, 52-54, pp. 621-629 (2003).
Jo, S., "Hierarchical Neural Control of Human Postural Balance and Bipedal Walking and Sagittal Plane," *PhD. Thesis*, MIT, (2007).
Johansson, J.L. et al., "A Clinical Comparison of Variable-Damping and Mechanically Passive Prosthetic Knee Devices," Variable-Damping vs. Mechanically Passive Prosthetic Knees, Aug. 2005.
Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).
Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).
Kadaba, M.P. et al., "Measurement of Lower Extremity Kinematics During Level Walking," *Journal of Orthapedic Research*, pp. 383-392, 1990.
Kadaba, M.P. et al., "Repeatability of Kinematic, Kinetic, and Electromyographic Data in Normal Adult Gait," *Journal of Orthapedic Research*, pp. 849-860, 1989.
Kajita, S. et al., "A Hop towards Running Humanoid Biped," Proceedings of the 2004 IEEE International Conference on Robotics & Automation, pp. 629-635, 2004.
Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.
Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).
Kaneko, K. et al., "Humanoid Robot HRP-2," Proceedings of the 2004 IEEE International Conference on Robotics & Automation, pp. 1083-1090 (Apr. 2004).
Kapti, A.O. et al., "Design and control of an active artificial knee joint," *Mechanism and Machine Theory*, vol. 41, pp. 1477-1485 (2006).
Katic, D. et al., "Survey of Intelligent Control Techniques for Humanoid Robots," *Journal of Intelligent and Robotic Systems*, vol. 37, pp. 117-141 (2003).
Kerrigan, D.C. et al., "A refined view of the determinants of gait: Significance of heel," *Archives of Physical Medicine and Rehabilitation*, vol. 81, Issue 8, pp. 1077-1080 (Aug. 2000).
Kerrigan, D.C. et al., "Quantification of pelvic rotation as a determinant of gait," Archives of Physical Medicine and Rehabilitation, vol. 82, Issue 2, pp. 217-220 (Feb. 2001).
Khatib, O. et al., "Coordination and Decentralized Cooperation of Multiple Mobile Manipulators," *Journal of Robotic Systems*, 13(11): 755-764 (1996).
Khatib, O. et al., "Whole-Body Dynamic Behavior and Control of Human-Like Robots," *International Journal of Humanoid Robotics*, vol. 1, No. 1, pp. 29-43 (2004).
Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).
Kim, J.-H. et al., "Realization of Dynamic Walking for the Humaniod Robot Platform KHR-1," *Advanced Robotics*, 18(7): 749-768, (2004).
Kirkwood, C.A. et al., "Automatic detection of gait events: a case study using inductive learning techniques," *J. Biomed. Eng.*, vol. 11, pp. 511-516 (Nov. 1989).
Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.
Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract (No date given).
Klute, G.K. et al., "Artificial Muscles: Actuators for Biorobotic Systems," *The International Journal of Robotics Research*, 21(4): 295-309 (2002).
Klute, G.K. et al., "Artificial Muscles: Actuators for Lower Limb Prostheses," Abstract in: Proceedings of the 2nd Annual Meeting of the VA rehabilitation Research and Development Service, Feb. 20-22, 2000, p. 107.
Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

(56) References Cited

OTHER PUBLICATIONS

Klute, G.K. et al., "Variable Stiffness Prosthesis for Transtibial Amputees," Dept of Veteran Affairs, Seattle, WA USA, 2 pages (2003).
Klute, G.K. et al., "Lower Limb Prostheses Powered by Muscle-like Pneumatic Actuators," Submitted to Oleodinamica e Pneumatica, Publisher Tecniche Nuove, Milano, Italy, Mar. 15, 2000, pp. 1-6.
Klute, G.K. et al., "McKibben Artificial Muscles: Pneumatic Actuators with Biomechanical Intelligence," IEEE/ASME 1999 International Conference on Advanced Intelligent Mechatronics (AIM '99), Atlanta, GA, Sep. 19-22, 1999, pp. 221-226.
Klute, G.K. et al., "Mechanical properties of prosthetic limbs: Adapting to the patient" Journal of Rehabilitation Research and Development, vol. 38, No. 3, pp. 299-307 (May/Jun. 2001).
Klute, G.K. et al., "Muscle-like Pneumatic Actuators for Below-knee Prostheses," "Actuator 2000: $7^{th}$ International Conference on New Actuators," Bremen, Germany on Jun. 19-21, 2000, pp. 289-292.
Klute, G.K. et al., "Powering Lower Limb Prosthetics with Muscle-like Actuators," Abstract in: Proceedings of the $1^{st}$ Annual Meeting of the VA Rehabilitation Research and Development Service, "Enabling Veterans: Meeting the Challenge of Rehabilitation in the Next Millenium," Washington, D.C., Oct. 1-3, 1998, p. 52.
Koganezawa, K. et al., Biomedical Engineering 1987, 2.3: Control Aspects of Artificial Leg, pp. 71-85.
Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.
Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).
Krishnaswamy, P., "A Computational Framework to Study Neural-Structural Interactions in Human Walking," *Master's Thesis, Massachusetts Institute of Technology*, (2010).
Krishnaswamy, P., et al., "Human Leg Model Predicts Ankle Muscle-Tendon Morphology, State, Roles and Energetics in Walking," *PLoS Comput. Biol.* 7(3): 1-16, 31001107.doi:10.10371/journal. pcbi.1001107 (2011). PMID: 21445231 PMCID: 3060164 (Mar. 2011).
Kuiken, T.A., et al., "Targeted muscle reinnervation for real-time myoelectric control of multifunction artificial arms," *JAMA: The Journal of the American Medical Association*, 301(6):619-628 (Feb. 2009).
Kuo, A.D., "A Simple Model of Bipedal Walking Predicts the Preferred Speed-Step Length Relationship," *Transactions of the ASME*, vol. 123, pp. 264-269 (Jun. 2001).
Kuo, A.D., "Energetics of Actively Powered Locomotion Using the Simplest Walking Model," *Journal of Biomechanical Engineering*, vol. 124, pp. 113-120 (Feb. 2002).
Lafortune, M.A., "Three-Dimensional Acceleration of the Tibia During Walking and Running," *J. Biomechanics*, vol. 24, No. 10, pp. 877-886 (1991).
LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.
Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.
Lichtwark, G.A., et al., "Interactions between the Human Gastrocnemius Muscle and the Achilles Tendon During Incline, Level and Decline Locomotion," *The Journal of Experimental Biology*, 209:4379-4388 (2006).
Light, L.H. et al., "Skeletal Transients on Heel Strike in Normal Walking with Different Footwear," J. Biomechanics, vol. 13, pp. 477-480 (1980).

Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.
Lloyd, R. et al., "Kinetic changes associated with load carriage using two rucksack designs," *Ergonomics*, vol. 43, No. 9, pp. 1331-1341 (2000).
Luinge, H.J., *Inertial Sensing of Human Movement*, Twente University Press, Enschede, the Netherlands, 80 pages (Feb. 15, 1973).
Lundberg, A., "Reflex control of stepping," The Norwegian Academy of Science and Letters, The Nansen Memorial Lecture, Oct. 10, 1968, 40 pages.
Ma, S.P., et al., "A Distribution-Moment Model of Energetics in Skeletal Muscle," *J. of Biomechanics*, 24:21-35 (1991).
Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.
MacKinnon, C., et al., "Control of Whole Body Balance in the Frontal Plane During Human Walking," *J. Biomech.*, 26(6):633-644 (1993).
Maganaris, C.N., "Force-length characteristics of in vivo human skeletal muscle," *Acta Physiol Scand*, 172: 279-285 (2001).
Maganaris, C.N., "Force-Length Characteristics of the in Vivo Human Gastroenemius Muscle," *Clinical Anatomy*, 16: 215-223 (2003).
Magnusson, S.P., et al., "Increased Cross-Sectional Area and Reduced Tensile Stress of the Achilles Tendon in Elderly Compared with Young Women,"*J. of Gerontology: Biological Sciences*, 58A(2):123-127 (2003).
Markowitz, J. , et al., "Speed Adaptation in a Powered Transtibial Prosthesis Controlled with a Neuromuscular Model," *Phil. Trans. R. Soc. B*, 366:1621-1631 (2011).
Martens, W.L. J., "Exploring the Information Content and Some Applications of Body Mounted Piezo-Resistive Accelerometers," 3 pages (No date given).
Martinez-Villalpando, E. C., "Design and Evaluation of a Biomimetic Agonist-Antagonist Active Knee Prosthesis." Doctoral dissertation, Massachusetts Institute of Technology (2012).
Maufroy, C. et al., "Towards a general neural controller for quadrupedal locomotion," Neural Networks, 21: 667-681 (2008).
Mayagoitia, R.E. et al., "Accelerometer and rate gyroscope measurement of kinematics: an inexpensive alternative to optical motion analysis systems," *Journal of Biomechanics*, 35: 537-542 (2002).
McFadyen, B.J. et al., "An Integrated Biomechanical Analysis of Normal Stair Ascent and Descent," J. Biomechanics, vol. 21, No, 9, pp. 733-744 (1988).
McGreer, T., "Passive Dynamic Walking," The International Journal of Robotics Research, 9, pp. 62-88 (1990).
McGreer, T., Chapter 4: "Principles of Walking and Running," *Advances in Comparative and Environmental Physiology*, vol. 11, pp. 113-139 (1992).
McIntosh, A.S. et al., "Gait dynamics on an inclined walkway," Journal of Biomechanics, vol. 39, Issue 13, pp. 2491-2502 (2006).
McMahon, T.A. et al., "Groucho Running," pp. 2326-2337 (1987).
McMahon, T.A. et al., "The Mechanics of Running: How Does Stiffness Couple with Speed?" J. Biomechanics, vol. 23, Suppl. 1, pp. 65-78 (1990).
Mergner, T., et al., "A Multisensory Posture Control Model of Human Upright Stance," *Prog. Brain Res.*, 142:189-201 (2003).
Minassian, K. et al., "Human lumbar cord circuitries can be activated by extrinsic tonic input to generate locomotor-like activity," Human Movement Science, 26: 275-295 (2007).
Mochon, S. et al., "Ballistic Walking," *J. Biomechanics*, vol. 13, pp. 49-57 (1980).
Molen, N.H., "Energy/Speed Relation of Below-Knee Amputees Walking on a Motor-Driven Treadmill," Physiol, 31: 173-185 (1973).
Morris, J.R.W., "Accelerometry—A Technique for the Measurement of Human Body Movements," J. Biomechanics, vol. 6, pp. 729-736 (1973).

(56) References Cited

OTHER PUBLICATIONS

Muraoka, T. et al., "Muscle fiber and tendon length changes in the human vastus lateralis during show pedaling," J. Appl. Physiol., 91: 2035-2040 (2001).
Naito, H., et al., "Development of Hip Disarticulation Prosthesies Using a Simulator Based on Neuro-Musculo-Skeletal Human Walking Model," *J. Biomechanics Abstract of the 5th World Congress of Biomechanics*, 39 (2006).
Nakagawa, A., "Intelligent Knee Mechanism and the Possibility to Apply the Principle to the Other Joints," paper presented at the Proceedings of the $20^{th}$ Annual International Conference of the IEEE Engineering in Medicine and Biology Society, 20(5): 2282-2287 (1998).
Neal, R. M. et al., "A View of the EM Algorithm That Justifies Incremental, Sparse, and Other Variants," pp. 1-14 (No date given).
Neptune, R., et al., "Modular Control of Human Walking: A simulation Study," *J. of Biomechanics*, 42:1282-1287 (2009).
Neptune, R.R., et al., "Forward Dynamics Simulations Provide Insight into Muscle Mechanical Work During Human Locomotion," *Exercise and Sport Science Reviews*, 37:203-210 (2009).
Neptune, R.R., et al., "The Effect of Walking Speed on Muscle Function and Mechanical Energetics," *Gait and Posture*, 28(1):135-143 (2008).
Ng, S.K. et al., "Fuzzy Model Identification for Classification of Gait Events in Paraplegics," IEEE Transactions on Fuzzy Systems, 5(4) (1997).
Nielsen, D.H. et al., "Comparison of Energy Cost and Gait Efficiency during Ambulation in Below-Knee Ampuees Using Different Prosthetic Feet," *JPO*, 1:24-31, http://www.oandp.org/jpo/library_/1989_01_024.asd, Retrieved on: Feb. 7, 2012.
O'Connor, S.M., et al., "Direction Dependent Control of Balance During Walking and Standing," *J. Neurophysiol*, 102:1411-1419 (2009).
Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).
Ogihara, N., and Yamazaki, N., "Generation of Human Bipedal Locomotion by a Bio-Mimetic Neuro-Musculo-Skeletal Model," *Biol. Cybern.*, 84: 1-11 (2001).
Palmer, M.L., "Sagittal Plane Characterization of Normal Human Ankle Function Across a Range of Walking Gait Speeds," Unpublished master's thesis, Massachusetts Institute of Technology, Massachusetts (2002).
Paluska, D., and Herr H., "The Effect of Series Elasticity on Actuator Power and Work Output: Implications for Robotic and Prosthetic Joint Design," Robotics and Autonomous Systems, 54:667-673 (2006).
Paluska, D., and Herr, H., "Series Elasticity and Actuator Power Output," paper presented at the Proceedings of the 2006 IEEE International Conference on Robotics and Automation (2006).
Pang, M.Y.C. and Yang, J.F., "The Initiation of the Swing Phase in Human Infact Stepping: Importance of Hip Position and Leg Loading," *Journal of Physiology*, 528(2):389-404 (2000).
Pasch, K.A., et al., "On the drive systems for high performance machines," *AMSE J. Mechanisms, Transmissions, and Automation in Design* 106(1):102-108 (Mar. 1984).
Paul, C., et al., "Development of a Human Neuro-Musculo-Skeletal Model for Investigation of Spinal Cord Injury," *Biol. Cybern.*, 93:153-170 (2005).
Pearson, K., et al., "Assessing Sensory Function in Locomotor Systems Using neurp-mechanical Simulations," *Trends in Neurosciences*, 29(11): 626-631 (2006).
Pearson, K.G., "Generating the Walking Gait: Role of Sensory Feedback," Progress in Brain Research, 143:123-129 (2004).
Peeraer, et al., "Development of EMG-based mode and intent recognition algorithms for a computer-controlled above-knee prosthesis," *Journal of Biomedical Engineering*, vol. 12., pp. 178-182, 1990.
Perry, J., et al., "Gait Analysis: Normal and Pathological Function," SLACK incorporated (1992).
Perry, J., et al., "Efficiency of Dynamic Elastic Response Prosthetic Feet," *Journal of Rehabilitation Research*, 30(1):137-143 (1993).
Petrofsky, J.S., et al., "Feedback Control System for Walking in Man," *Comput. Biol. Med.* 14(2): 135-149 (1984).
Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).
Popovic, D. and Sinkjaer, T., "Control of Movement for the Physically Disabled: Control for Rehabilitation Technology," (Springer Publisher) pp. 270-302, (No date given).
Popovic, D., et al., "Control Aspects of Active Above-Knee Prosthesis," *Int. J. Man-Machine Studies*, 35:751-767 (1991).
Popovic, M, et al., "Angular Momentum Primitives for Human Walking: Biomechanics and Control," paper presented at the Proceedings IEEE/RSJ International Conference on Intelligent Robots and Systems, Sendai, Japan 1685-1691 (2004).
Popovic, M., et al., "Angular Momentum Regulation During Human Walking: Biomechanics and Control," paper presented at the Proceedings IEEE International Conference on Robotics and Automation, 2405-2411 New Orleans, LA (2004).
Popovic, M., et al. ,"Conservation of Angular Momentum During Human Locomotion," *MIT Artificial Intelligence Laboratory*, pp. 231-232 (2002).
Popovic, M.B. and Herr, H., "Global Motion Control and Support Base Planning," Massachusetts Institute of Technology, pp. 1-8 (No date given).
Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).
Popovic, M.B., et al., "Zero Spin Angular Momentum Control: Definition and Applicability," Massachusetts Institute of Technology, pp. 1-16 (No date given).
Popovic, M.R, et al., "Gait Identification and Recognition Sensor," paper presented at the Proceedings of $6^{th}$ Vienna International Workshop on Functional Electrostiumlation (Sep. 1998).
Pratt, G.A. and Williamson, M.M., "Series Elastic Actuators." Paper presented at the meeting of the IEEE, pp. 399-406 (1995).
Pratt, G.A., "Legged Robots at MIT: What's New Since Raibert." Paper presented at the meeting of the IEEE, Robotics and Automation Magazine (Sep. 2000).
Pratt, G.A., "Low Impedance Walking Robots," *Integ. and Comp. Biol.*, 42: 174-181 (2002).
Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).
Prilutsky, BI, "Work, Energy Expenditure, and Efficiency of the Stretchshorting Cycle." *J. Appl. Biomech.*, 13(4):466-470 (1997).
Prochazka, A. and Yakovenko, S., "The Neuromechanical Tuning Hypothesis," *Progress in Brain Research*, 165: 257-267 (2007).
Prochazka, A., et al., "Positive Force Feedback Control of Muscles," *The American Physiological Society*, pp. 3226-3236 (1997).
Prochazka, A., et al., "Sensory Control of Locomotion: Reflexes Versus Higher-Level Control," *Sensorimotor Control of Movement and Posture*, pp. 357-367 (2002).
Raibert, M.H., "Legged Robots that Balance," MIT Press, Cambridge, MA, p. 89 (1985).
Ralson, H.J., "Neural Control of Locomotion," *Chapter Energetics of Human Walking*, pp. 399-406, Plenum Press (1976).
Rassier, D.E., et al., "Length Dependence of Active Force Production in Skeletal Muscle," *The American Physiological Society*, pp. 1445-1457 (1999).
Riener, R., et al., "Stair Ascent and Descent at Different Inclinations," *Gait and Posture*, 15: 32-44 (2002).
Rietman, J.S., et al., "Gait Analysis in Prosthetics: Opinions, Ideas and Conclusions," *Prosthetics and Orthotics International*, 26: 50-57 (2002).

(56) References Cited

OTHER PUBLICATIONS

Robinson, D.W., "Design and Analysis of Series Elasticity in Closed-Loop Actuator Force Control." Unpublished doctoral dissertation, Massachusetts Institute of Technology (2000).
Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).
Rosen, J., et al., "A Myosignal-Based Powered Exoskeleton System," *IEEE Transaction on Systems, Man, and Cybernetics—Part A: Systems and Humans*, 31(3): 210-222 (2001).
Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).
Rybak, I.A., et al., "Modelling Spinal Circuitry Involved in Locomotor Pattern Generation: Insights from Deletions During Fictive Locomotion," *J. Physiol.*, 577(2): 617-639 (2006).
Rybak, I.A., et al., "Modelling Spinal Circuitry Involved in Locomotor Pattern Generation: Insights from the Effects of Afferent Stimulation," *J. Physiol.*, 577(2): 641-658 (2006).
Sanderson, D.J. and Martin. P.E., "Lower Extremity Kinematic and Kinetic Adaptations in Unilateral Below-Knee Amputees During Walking," *Gait & Posture*, 6(2): 126-136 (1997).
Sanger, T.D., "Human Ann Movements Described by a Low-Dimensional Superposition of Principal Components," *The J. of Neuroscience*, 20(3): 1066-1072 (2000).
Sanger, T.D., "Bayesian filtering of myoelectric signals," *Journal of Neurophysiology*, 97(2): 1839-1845 (Feb. 2007).
Saranli, U., et al., "RHex: A Simple and Highly Mobile Hexapod Robot," *The International Journal of Robotics Research*, pp. 616-631 (2001).
Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).
Saxena, et al. "EMG operated electronic artificial-leg controller," *Medical and Biological Engineering and Computation*, vol. 15, pp. 553-557, 1997.
Schaal, S. and Atkeson, C.G., "Constructive Incremental Learning from Only Local Information," *Neural Computation*, 10(8): 2047-2084 (1998).
Schaal, S., "Is Imitation Learning the Route to Humanoid Robots?", *Trends in Cognitive Sciences*, 3: 233-242 (1999).
Scott, S.H. and Winter, D.A., "Biomechanical Model of the Human Foot: Kinematics and Kinetics During the Stance Phase of Walking," *J. Biomechanics*, 26(9): 1091-1104 (1993).
Sentis, L. and Khatib, O., "Task-Oriented Control of Humanoid Robots Through Prioritization." Paper presented at the IEEE-RAS/RSJ International Conference on Humanoid Robots, pp. 1-16 (No date given).
Seyfarth, A., et al., "A Movement Criterion for Running," *J. of Biomechanics*, 35: 649-655 (2002).
Seyfarth, A., et al., "Stable Operation of an Elastic Three-Segment Leg," *Biol. Cybern.*, 84: 365-382 (2001).
Seyfarth, A., et al., "Swing-Leg Retraction: A Simple Control Model for Stable Running," *The J. of Experimental Biology*, 206: 2547-2555 (2003).
Sinkjaer, T., et al., "Major role for sensory feedback in soleus EMG activity in the stance phase of walking in man," *Journal of Physiology*, 523.3: 817-827 (2000).
Skinner, H.B., and Effeney, D.J., "Gait Analysis in Amputees," *American Journal of Physical Medicine*, 64(2): 82-89 (1985).
Smidt, G.L., et al., "An Automated Accelerometry System for Gait Analysis," *J. Biomechanics*, 10: 367-375 (1977).
Srinivasan, M., "Energetics of Legged Locomotion: Why is Total Metabolic Cost Proportional to the Cost of Stance Work." ISB XXth Congress—ASB $29^{th}$ Annual Meeting, Cleveland, OH (Jul. 31-Aug. 5, 2003.

Stepien, J., et al., "Activity Levels Among Lower-Limb Amputees: Self-Report Versus Step Activity Monitor," *Arch. Phys. Med. Rehabil.*, 88: 896-900 (2007).
Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).
Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).
Sup, F., et al., "Design and Control of a Powered Transfemoral Prosthesis," *The International Journal of Robotics Research*, 27(2): 263-273 (2008).
Supplementary European Search Report Application No. 10736533.0, dated Aug. 16, 2013.
Supplementary European Search Report Application No. 10736550.0, dated Aug. 1, 2013.
Taga, G., "A model of the neuro-musculo-skeletal system for human locomotion," *Biol. Cybern.*, 73: 97-111 (1995).
Taga, G., "A Model of the Neuro-Musculo-Skeletal System for Anticipatory Adjustment of Human Locomotion during Obstacle Avoidance," *Biol. Cybern.*, 78:9-17 (1998).
Takayuki, F., et al., "Biped Locomotion using Multiple Link Virtual Inverted Pendulum Model," *T.IEE Japan*, 120-C (2): 208-214 (2000).
Thoroughman, K., and Shadmehr, R., "Learning of action through adaptive combination of motor primitives," *Nature*, 407: 742-747(2000).
Tomovie, R., and McHee, R.B., "A Finite State Approach to the Synthesis of Bioengineering Control Systems," *IEEE Transactions on Human Factors in Electronics*, 7(2): 65-69 (1966).
Tong, K., and Granat, M., "A practical gait analysis system using gyroscopes," *Medical Engineering & Physics*, 21: 87-94 (1999).
Türker, K., "Electromyography: Some Methodological Problems and Issues," *Phys. Ther.*, 73: 698-710 (1993).
Umberger, B.R., et al., "Mechanical Power and Efficiency of Level Walking with Different Stride Rates," *J. of Experimental Biology*, 210:3255-3265 (2007).
Van den Bogert, A. J., "Exotendons for Assistance of Human Locomotion," Biomedical Engineering OnLine, BioMed Central, 2(17):1-8 (2003).
Van den Bogert, A. J., et al., "A Method for Inverse Dynamic Analysis Using Accelerometry," *J. Biochemechanics*, 29(7): 949-954 (1996).
Veltink, P.H., et al., "The Feasibility of Posture and Movement Detection by Accelerometry," paper presented at the IEEE meeting (1993).
Visser, J.J., et al., "Length and Moment Ann of Human Leg Muscles as a Function of Knee and Hip-Joint Angles," *Eur. J. Appl. Physiol.*, 61:453-460 (1990).
Vukobratovic, M., and Stepanenko, J., "Mathematical Models of General Anthropomorphic Systems," Mathematical Biosciences, 17: 191-242 (1973).
Vukobratovic, M., Juricic, D., "Contribution to the Synthesis of Biped Gait," paper presented at the IEEE Transactions on Bio-Medical Engineering, BME-16(1) (Jan. 1969).
Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).
Wang, J., "EMG Control of Prosthetic Ankle Plantar Flexion," *MIT Master's Thesis* (2011).
Waters, R.L., et al., "Energy Cost of Walking of Amputees: The Influence of Level of Amputation," *The Journal of Bone and Joint Surgery*, 58A(1): 42-46 (1976).
Wilkenfeld, A., "Biologically Inspired Autoadaptive Control of a Knee Prosthesis," unpublished doctoral dissertation, Massachusetts Institute of Technology, Cambridge, MA (2000).
Wilkenfeld, A., and Herr, H., "An Auto-Adaptive External Knee Prosthesis," MIT Lab., (No date given).

(56) References Cited

OTHER PUBLICATIONS

Willems, P.A., et al., "External, Internal and Total Work in Human Locomotion," *J. of Experiment Biology*, 198:379-393 (1995).
Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).
Willemsen, A.Th.M., et al., "Real-Time Gait Assessment Utilizing a New Way of Accelerometry," *J. Biomechanics*, 23(8):859-863 (1990).
Williams, B.C., et al., "Mode Estimation of Model-Based Programs: Monitoring Systems with Complex Behavior," paper submitted to Massachusetts Institute of Technology, Cambridge, MA, (No date given).
Williamson, M.M., "Series Elastic Actuators," A.I. Technical Report submitted to Massachusetts Institute of Technology, Cambridge, Massachusetts (Jan. 1995).
Winter, D.A., "Energy Generation and Absorption at the Ankle and Knee during Fast, Natural, and Slow Cadences," *Clinical Orthopedics and Related Research*, 175: 147-154 (1983).
Winter, D.A., "Biomechanical Motor Patterns in Normal Walking," *J. of Motor Behavior*, 15(4):302-330 (1983).
Winter, D.A., and Robertson, D.G.E., "Joint Torque and Energy Patterns in Normal Gait," Biol. Cybernetics, 29:137-142 (1978).
Winter, D.A., and Sienko, S.E., "Biomechanics of Below-Knee Amputee Gait," J. Biomechanics, 21(5):361-367 (1988).
Wisse, M., "Essentials of Dynamic Walking: Analysis and Design of Two-legged Robots," 195 pages (No date given).
Woodward, M.I. and Cunningham, J.L., "Skeletal Accelerations Measured During Different Exercises," *Proc. Instn. Mech. Engrs.*, 207: 79-85 (1993).
Wu, G. and Ladin, Z., "The Study of Kinematic Transients in Locomotion Using the Integrated Kinematic Sensor," *IEEE Transactions on Rehabilitation Engineering*, 4(3): 193-200 (1996).
Yakovenko, S. et al., "Contribution of Stretch Reflexes to Locomotor Control: A Modeling Study," *Biol. Cybern.*, 90: 146-155 (2004).
Yamaguchi, G.T., et al., "A Survey of Human Musculotendon Actuator Parameters," *Technical Report: Multiple Muscle Systems Biomechanics and Movement Organization*, (1990).
Yun, X., "Dynamic State Feedback Control of Constrained Robot Manipulators." Paper presented at the Proceedings of the 27th Conference on Decision and Control, Austin, TX (Dec. 1988).
Zajac, F.E., "Muscle and tendon: properties, models, scaling, and application to biomechanics and motor control," *Critical Reviews in Biomedical Engineering*, 17(4):359-411 (1989).
Ziegler-Graham, K., et al., "Estimating the Prevalence of Limb Loss in the United States, 2005 to 2050," *Archives of Physical Medicine and Rehabilitation*, 89(3):422-429 (2008).
Zlatnik, D. et al., "Finite-State Control of a Trans-Femoral (TF) Prosthesis," *IEEE Transactions on Control Systems Technology*, 10(3): 408-420 (2002).
Geyer, H. et al., "A Muscle-Reflex Model that Encodes Principles of Legged Mechanics Produces Human Walking Dynamics and Muscle Activities," *IEEE Transactions on Neural Systems and Rehabilitation Engineering*, vol. X, No. X, pp. 1-10 (2010).
Non-final Office Action for U.S. Appl. No. 13/865,840, entitled "Neuromuscular Model-Based Sensing and Control Paradigm for a Robotic Leg," dated Jan. 14, 2015.
Notice of Allowance for U.S. Appl. No. 13/865,840, "Neuromuscular Model-Based Sensing and Control, Paradigm for a Robotic Leg", dated Aug. 25, 2015.
Non-final Office Action for U.S. Appl. No. 14/520,091, entitled "Model-Based Neuromechanical Controller for a Robotic Leg," dated Apr. 4, 2016.
Notice of Allowance for U.S. Appl. No. 14/520,091, entitled "Model-Based Neuromechanical Controller for a Robotic Leg," dated Sep. 8, 2016.
Non-Final Office Action from U.S. Appl. No. 14/978,445, dated Feb. 10, 2017.
PID Loop Descriptions, National Instruments, http://zone.ni.com/reference/en-XX/help/371093K-01/mclvhowto/pidloopdescriptions/, 4 pages, (Aug. 2011).
Final Office Action from U.S. Appl. No. 14/978,445, dated Jul. 17, 2017.
Notice of Allowance from U.S. Appl. No. 14/978,445, dated Jan. 4, 2018.

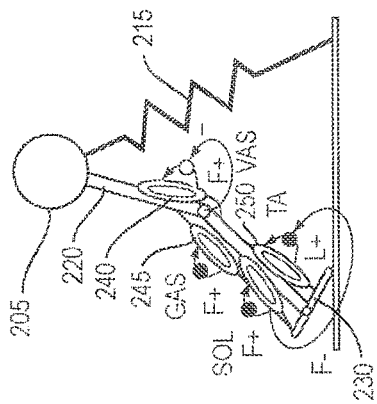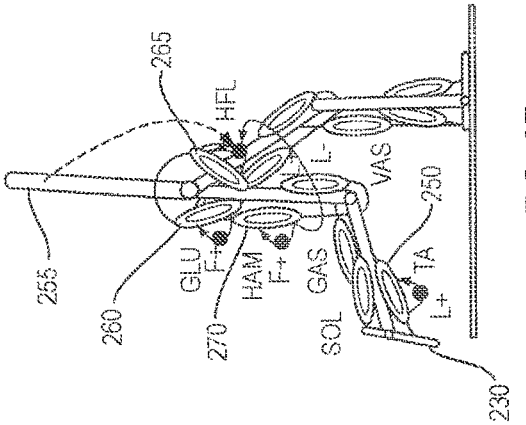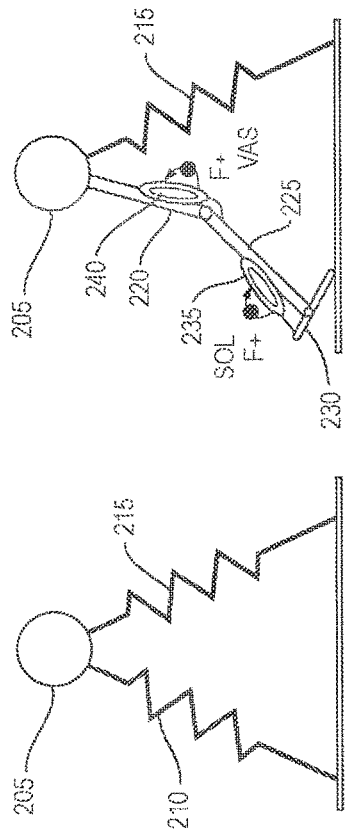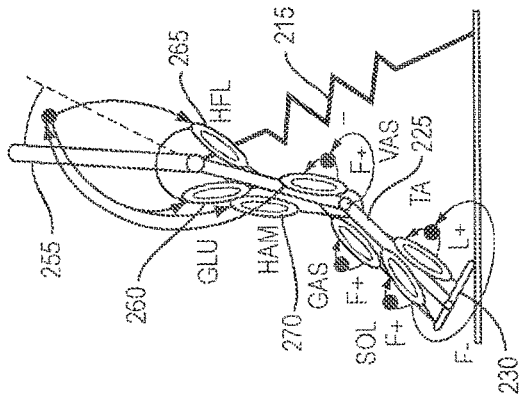
FIG. 2A  FIG. 2B  FIG. 2C
FIG. 2D  FIG. 2E  FIG. 2F

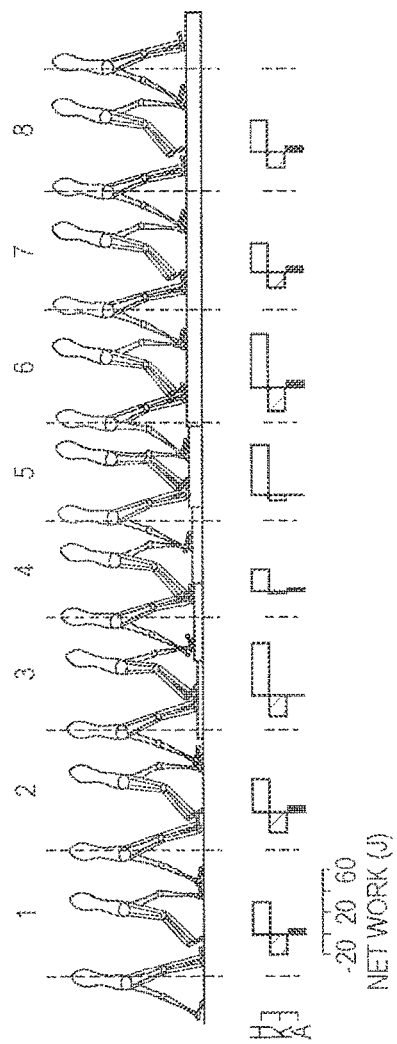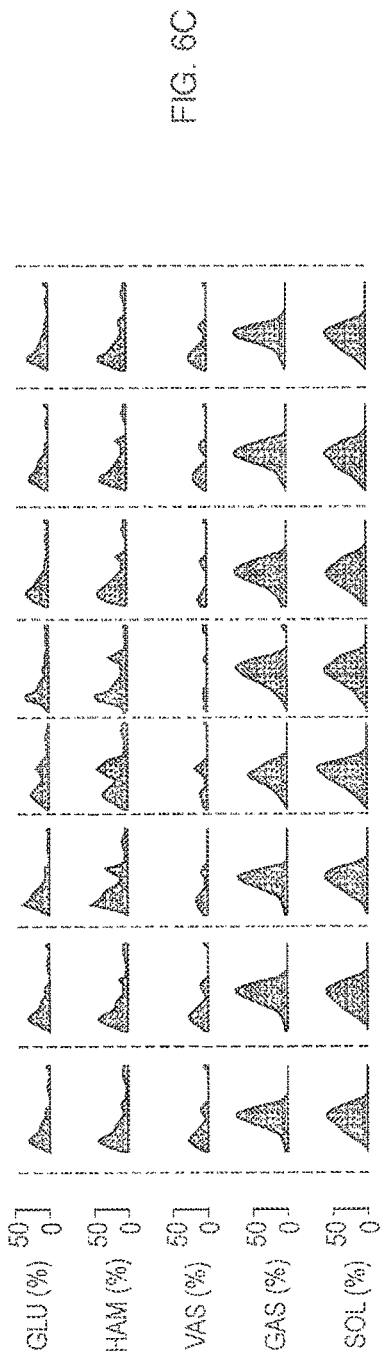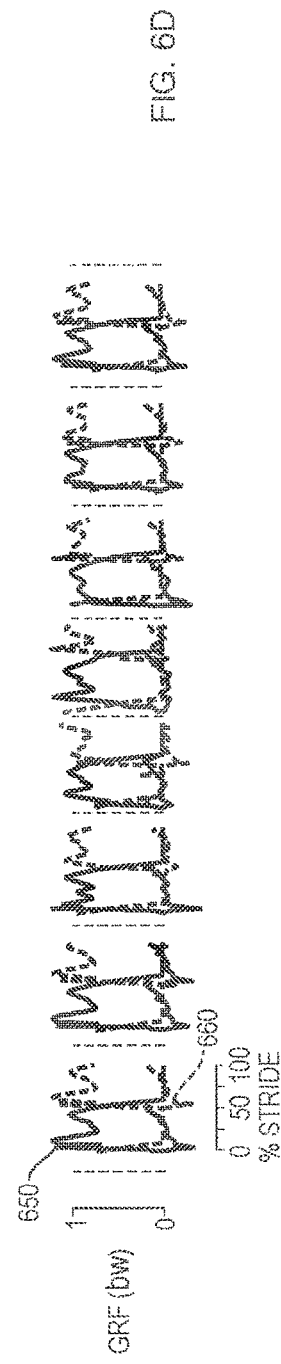
FIG. 6A
FIG. 6B
FIG. 6C
FIG. 6D

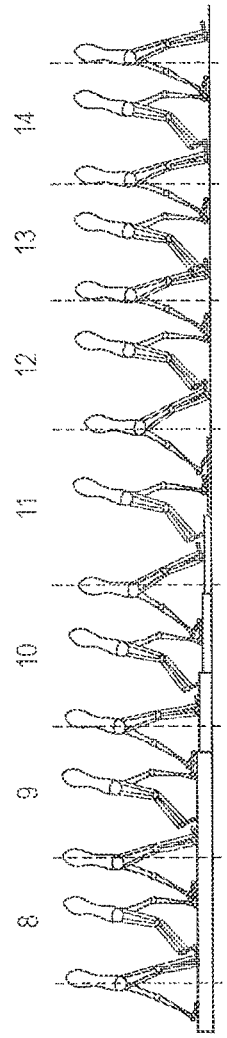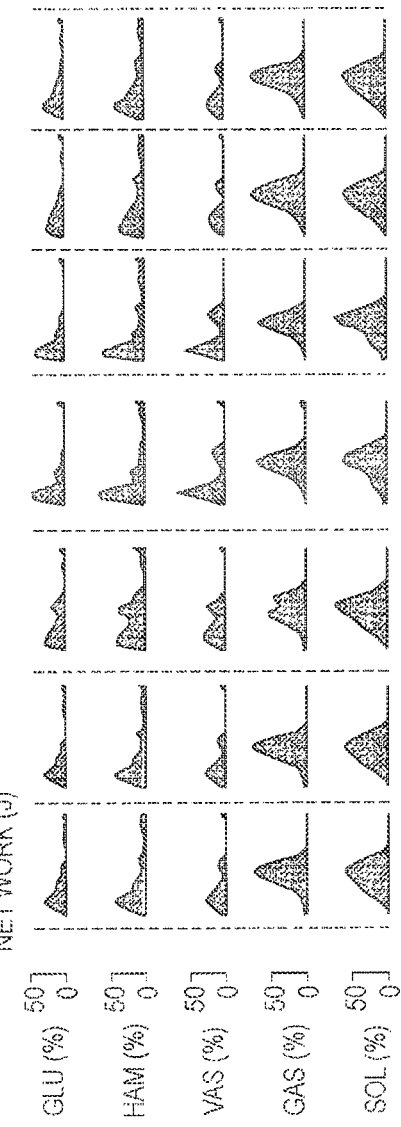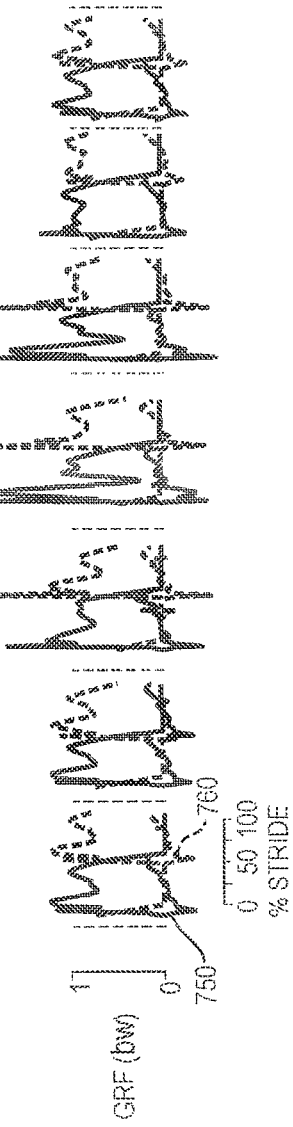
FIG. 7A
FIG. 7B
FIG. 7C
FIG. 7D

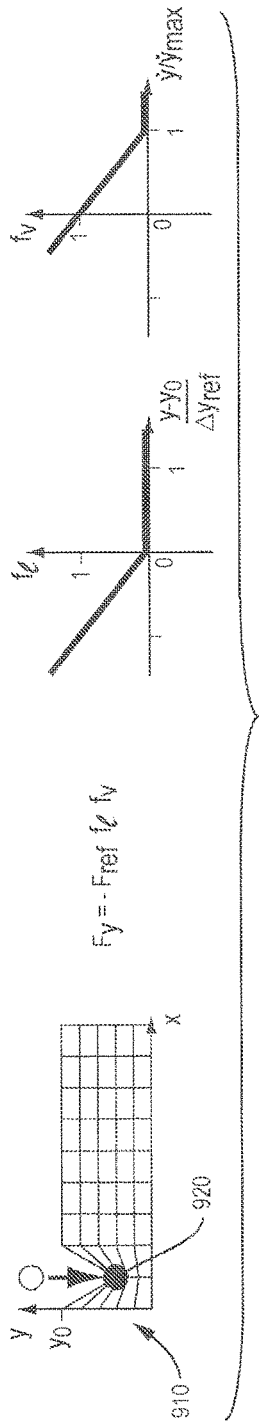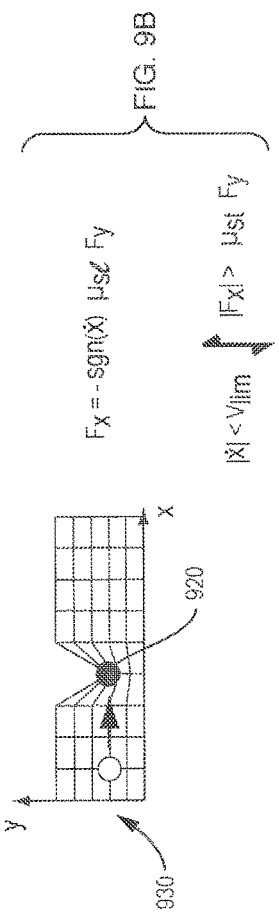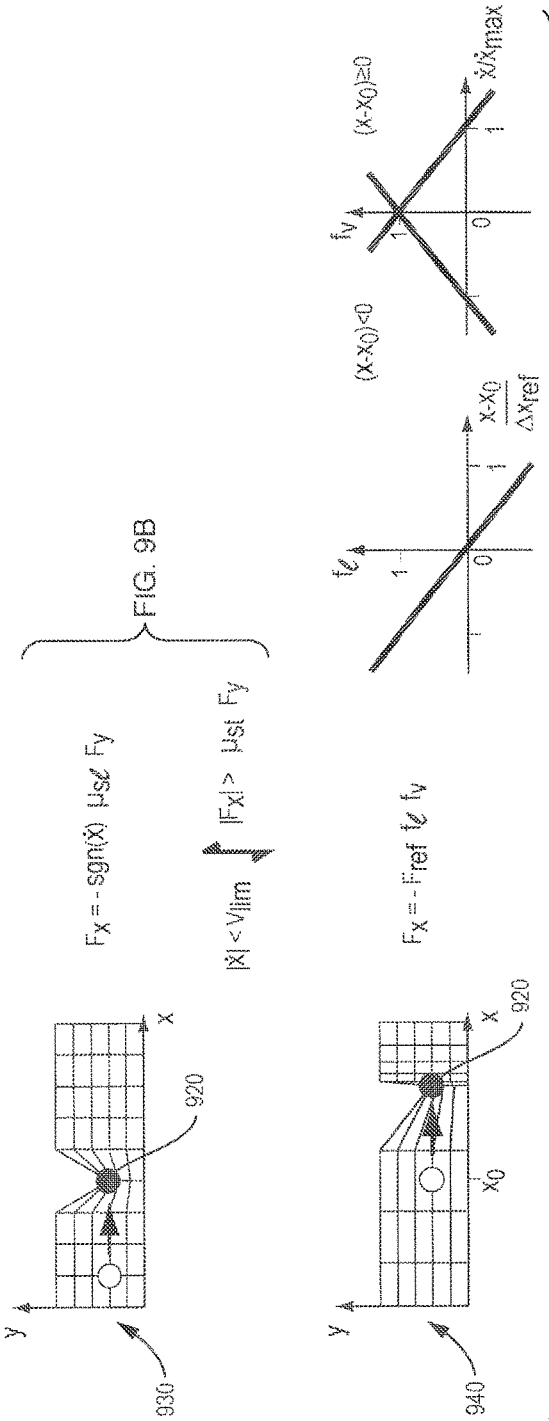
FIG. 9A
FIG. 9B
FIG. 9C

METHOD FOR USING A MODEL-BASED CONTROLLER FOR A ROBOTIC LEG

RELATED APPLICATIONS

This application is a continuation application U.S. patent application Ser. No. 14/520,091, filed Oct. 21, 2014, which is a divisional of U.S. patent application Ser. No. 12/698,128, filed Feb. 1, 2010, now U.S. Pat. No. 8,864,846, which claims the benefit of U.S. Provisional Patent Appl. Ser. No. 61/148,545, filed Jan. 30, 2009, and is a continuation-in-part of U.S. patent application Ser. No. 12/608,627, filed Oct. 29, 2009, now U.S. Pat. No. 8,870,967, which is a continuation of U.S. patent application Ser. No. 11/642,993, filed Dec. 19, 2006, now abandoned, which claims the benefit of the U.S. Provisional Patent Appl. Ser. No. 60/751,680, filed Dec. 19, 2005, and is a continuation-in-part of U.S. patent application Ser. No. 11/600,291, filed Nov. 15, 2006, now abandoned, which claims the benefit of U.S. Provisional Appl. No. 60/736,929, filed Nov. 15, 2005 and U.S. Provisional Appl. No. 60/705,651, filed Aug. 4, 2005, and is a continuation-in-part of U.S. patent application Ser. No. 11/395,448, filed Mar. 31, 2006, now abandoned, which claims the benefit of U.S. Provisional Patent Appl. No. 60/666,876, filed Mar. 31, 2005, and of U.S. Provisional Patent Appl. No. 60/704,517, filed Aug. 1, 2005, and U.S. patent application Ser. No. 11/600,291, filed Nov. 15, 2006, now abandoned, is a continuation-in-part of U.S. patent application Ser. No. 11/499,853, filed Aug. 4, 2006, now U.S. Pat. No. 7,313,463, which claims the benefit of U.S. Provisional Appl. 60/705,651, filed Aug. 4, 2005.

U.S. patent application Ser. No. 11/499,853, filed Aug. 4, 2006, now U.S. Pat. No. 7,313,463 is a continuation-in-part of U.S. patent application Ser. No. 11/395,448, filed Mar. 31, 2006, now abandoned, which claims the benefit of U.S. Provisional Appl. No. 60/704,517, filed Aug. 1, 2005, and U.S. Provisional Appl. No. 60/666,876, filed Mar. 31, 2005.

U.S. patent application Ser. No. 12/698,128, filed Feb. 1, 2010, now U.S. Pat. No. 8,864,846, is also a continuation-in-part of U.S. patent application Ser. No. 12/157,727, filed Jun. 12, 2008, now U.S. Pat. No. 8,512,415, which claims the benefit of U.S. Provisional Appl. No. 60/934,223, filed Jun. 12, 2007, and is a continuation-in-part of U.S. patent application Ser. No. 11/642,993, filed Dec. 19, 2006, now abandoned.

The present application claims the benefit of the filing date of each of the foregoing patent applications and incorporates the disclosures of each of the foregoing applications herein by reference in their entirety.

GOVERNMENT SUPPORT

This invention was made with U.S. government support under Grant Numbers VA241-P-0026; 65OD70025 and VA241-P-0479, 650-D85022, awarded by the United States Veterans Administration. The government has certain rights in this invention.

FIELD OF THE TECHNOLOGY

The present invention relates to control of artificial joints and limbs for use in prosthetic, orthotic, exoskeletal, or robotic devices and, in particular, to control methodology for a robotic leg based on a neuromuscular model of locomotion.

BACKGROUND OF THE INVENTION

Legged locomotion of animals and humans is controlled by a complex network of neurons. Proposed in the early 20th century [Brown, T. G., 1914. On the nature of the fundamental activity of the nervous centres; together with an analysis of the conditioning of rhythmic activity in progression, and a theory of the evolution of function in the nervous system. J Physiol 48 (1), 18-46.]. and firmly established today [Orlovsky, G., Deliagina, T., Grillner, S., 1999. Neuronal control of locomotion: from mollusc to man. Oxford University Press, New York], the central pattern generator (CPG) forms the basis of this network.

In the current view, the CPG consists of layers of neuron pools in the spinal cord [Rybak, I. A., Shevtsova, N. A., Lafreniere-Roula, M., McCrea, D. A., 2006. Modelling spinal circuitry involved in locomotor pattern generation: insights from deletions during fictive locomotion. J Physiol 577 (Pt 2), 617-639] which, through other neuron pools channeling muscle synergies, provide rhythmic activity to the leg extensor and flexor muscles [Dietz, V, 2003. Spinal cord pattern generators for locomotion. Clin Neurophysiol 114 (8), 1379-1389; Minassian, K., Persy, I., Rattay, F., Pinter, M. M., Kern, H., Dimitrijevic, M. R., 2007. Human lumbar cord circuitries can be activated by extrinsic tonic input to generate locomotor-like activity. Hum Mov Sci 26 (2), 275-295] sufficient to generate stepping movements, even in the absence of spinal reflexes [Grillner, S., Zangger, P., 1979. On the central generation of locomotion in the low spinal cat. Exp Brain Res 34 (2), 241-261; Frigon, A., Rossignol, S., 2006. Experiments and models of sensorimotor interactions during locomotion. Biol Cybern 95 (6), 607-627]. Spinal reflexes are nevertheless part of this complex network [Rybak, I. A., Stecina, K., Shevtsova, N. A., McCrea, D. A., 2006. Modelling spinal circuitry involved in locomotor pattern generation: insights from the effects of afferent stimulation. J Physiol 577 (Pt 2), 641-658], contributing to the selection of locomotive patterns, the timing of the extensor and flexor activities, and the modulation of the CPG output.

Using this combination of a central pattern generation and modulating reflexes, neuromuscular models of lampreys [Ekeberg, O., Grillner, S., 1999. Simulations of neuromuscular control in lamprey swimming. Philos Trans R Soc Lond B Biol Sci 354 (1385), 895-902], salamanders [Ijspeert, A., Crespi, A., Ryczko, D., Cabelguen, J.-M., 2007. From swimming to walking with a salamander robot driven by a spinal cord model. Science 315 (5817), 1416-1420], cats [Ivashko, D. G., Prilutski, B. I., Markin, S. N., Chapin, J. K., Rybak, I. A., 2003. Modeling the spinal cord neural circuitry controlling cat hindlimb movement during locomotion. Neurocomputing 52-54, 621-629; Yakovenko, S., Gritsenko, V, Prochazka, A., 2004. Contribution of stretch reflexes to locomotor control: a modeling study. Biol Cybern 90 (2), 146-155; Maufroy, C., Kimura, H., Takase, K., 2008. Towards a general neural controller for quadrupedal locomotion. Neural Netw 21(4), 667-681], and humans [Ogihara, N., Yamazaki, N., 2001. Generation of human bipedal locomotion by a bio-mimetic neuro-musculo-skeletal model. Biol Cybern 84 (1), 1-11; Paul, C., Bellotti, M., Jezernik, S., Curt, A., 2005. Development of a human neuro-musculo-skeletal model for investigation of spinal cord injury. Biol Cybern 93 (3), 153-170] have developed into essential tools for studying different control strategies in animal and human locomotion. The emphasis of these models has been to reproduce the architecture of the CPG and underlying reflexes suggested by experiments [Pearson, K., Ekeberg, O., Buschges, A., 2006. Assessing sensory function in locomotor systems using neuro-mechanical simulations. Trends Neurosci 29 (11), 625-631]. However, little attention has been paid to understanding how such architectures might represent or encode principles of locomotion mechanics.

These principles suggest that, in contrast to the complexity of the identified neural networks, legged locomotion requires little or no control. For instance, two conceptual models of walking [Alexander, R., 1976. Mechanics of bipedal locomotion. In: Perspectives in experimental biology (Ed. Davies, P. S.) Pergamon, Oxford; Mochon, S., McMahon, T., 1980. Ballistic walking. J. Biomech. 13 (1), 49-57] and running [Blickhan, R., 1989. The spring-mass model for running and hopping. J. of Biomech. 22, 1217-1227; McMahon, T., Cheng, G., 1990. The mechanism of running: how does stiffness couple with speed? J. of Biomech. 23, 65-78] have been put forth that capture dominant mechanisms of legged locomotion. Researchers have demonstrated the capacity of these models to self-stabilize if the mechanical system is properly tuned [McGeer, T., 1990. Passive dynamic walking. Int. J. Rob. Res. 9 (2), 62-82; McGeer, T., 1992. Principles of walking and running. Vol. 11 of Advances in Comparative and Environmental Physiology. Springer-Verlag Berlin Heidelberg, Ch. 4; Seyfarth, A., Geyer, H., Günther, M., Blickhan, R., 2002. A movement criterion for running. J. of Biomech. 35, 649-655; Ghigliazza, R., Altendorfer, R., Holmes, P., Koditschek, D., 2003. A simply stabilized running model. SIAM J. Applied. Dynamical Systems 2 (2), 187-218]. Walking and running robots have moreover demonstrated the practical relevance and control benefits derived from this principle [Raibert, M., 1986. Legged robots that balance. MIT press, Cambridge; McGeer, T., 1990. Passive dynamic walking. Int. J. Rob. Res. 9 (2), 62-82; Saranli, U., Buehler, M., Koditschek, D., 2001. Rhex: A simple and highly mobile hexapod robot. Int. Jour. Rob. Res. 20(7), 616-631; Collins, S., Ruina, A., Tedrake, R., Wisse, M., 2005. Efficient bipedal robots based on passive-dynamic walkers. Science 307 (5712), 1082-1085]. But it remains an open question how this and other principles of legged mechanics are integrated into the human motor control system.

The importance of this interplay between mechanics and motor control has been recognized by neuroscientists and biomechanists alike [Pearson, K., Ekeberg, O., Buschges, A., 2006. Assessing sensory function in locomotor systems using neuro-mechanical simulations. Trends Neurosci 29 (11), 625-631]. For instance, although it is generally accepted that the CPG forms a central drive for motor activity in locomotion [Grillner, S., Zangger, P., 1979. On the central generation of locomotion in the low spinal cat. Exp Brain Res 34 (2), 241-261; Dietz, V, 2003. Spinal cord pattern generators for locomotion. Clin Neurophysiol 114 (8), 1379-1389; Frigon, A., Rossignol, S., 2006. Experiments and models of sensorimotor interactions during locomotion. Biol Cybern 95 (6), 607-627; Ijspeert, A. J., 2008. Central pattern generators for locomotion control in animals and robots: a review. Neural Netw 21(4), 642-653], Lundberg suggested in 1969 that, out of its rather simple central input, spinal reflexes, which relay information about locomotion mechanics, could shape the complex muscle activities seen in real locomotion [Lundberg, A., 1969. Reflex control of stepping. In: The Nansen memorial lecture V, Oslo: Universitetsforlaget, 5-42]. Refining this idea, Taga later proposed that, because "centrally generated rhythms are entrained by sensory signals which are induced by rhythmic movements of the motor apparatus . . . [,] motor output is an emergent property of the dynamic interaction between the neural system, the musculo-skeletal system, and the environment" [Taga, G., 1995. A model of the neuro-musculo-skeletal system for human locomotion. I. Emergence of basic gait. Biol. Cybern. 73 (2), 97-111]. In support, he presented a neuromuscular model of human locomotion that combines a CPG with sensory feedback and demonstrates how basic gait can emerge from the global entrainment between the rhythmic activities of the neural and of the musculo-skeletal system.

What the actual ratio of central and reflex inputs is that generates the motor output continues to be debated [Pearson, K. G., 2004. Generating the walking gait: role of sensory feedback. Prog Brain Res 143, 123-129; Frigon, A., Rossignol, S., 2006. Experiments and models of sensorimotor interactions during locomotion. Biol Cybern 95 (6), 607-627; Hultborn, H., 2006. Spinal reflexes, mechanisms and concepts: from Eccles to Lundberg and beyond. Prog Neurobiol 78 (3-5), 215-232; Prochazka, A., Yakovenko, S., 2007. The neuromechanical tuning hypothesis. Prog Brain Res 165, 255-265]. For instance, for walking cats, it has been estimated that only about 30 percent of the muscle activity observed in the weight bearing leg extensors can be attributed to muscle reflexes [Prochazka, A., Gritsenko, V, Yakovenko, S., 2002. Sensory control of locomotion: reflexes versus higher-level control. Adv Exp Med Biol 508, 357-367; Donelan, J. M., McVea, D. A., Pearson, K. G., 2009. Force regulation of ankle extensor muscle activity in freely walking cats. J Neurophysiol 101 (1), 360-371].

In humans, the contribution of reflexes to the muscle activities in locomotion seems to be more prominent. Sinkjaer and colleagues estimated from unloading experiments that reflexes contribute about 50 percent to the soleus muscle activity during stance in walking [Sinkjaer, T., Andersen, J. B., Ladouceur, M., Christensen, L. O., Nielsen, J. B., 2000. Major role for sensory feedback in soleus EMG activity in the stance phase of walking in man. J Physiol 523 Pt 3, 817-827]. More recently, Grey and colleagues found that the soleus activity changes proportionally to changes in the Achilles tendon force, suggesting a direct relationship between positive force feedback and activity for this muscle [Grey, M. J., Nielsen, J. B., Mazzaro, N., Sinkjaer, T., 2007. Positive force feedback in human walking. J Physiol 581 (1), 99-105]. Whether such a large reflex contribution is present for all leg muscles remains open. Perhaps a proximo-distal gradient exists in motor control where proximal leg muscles are mainly controlled by central inputs while distal leg muscles are dominated by reflex inputs due to higher proprioceptive feedback gains and a larger sensitivity to mechanical effects, as Daley and colleagues concluded from locomotion experiments with birds [Daley, M. A., Felix, G., Biewener, A. A., 2007. Running stability is enhanced by a proximo-distal gradient in joint neuromechanical control. J Exp Biol 210 (Pt 3), 383-394].

Adaptation to terrain is an important aspect of walking. Today's commercially-available ankle-foot prostheses utilize lightweight, passive structures that are designed to present appropriate elasticity during the stance phase of walking [S. Ron, Prosthetics and Orthotics: Lower Limb and Spinal. Lippincott Williams & Wilkins 2002]. The advanced composites used in these devices permit some energy storage during controlled dorsiflexion and plantar flexion, and subsequent energy release during powered plantar flexion, much like the Achilles tendon in the intact human [A. L. Hof, B. A. Geelen, Jw. Van den Berg, "Calf muscle moment, work and efficiency in level walking; role of series elasticity," Journal of Biomechanics, Vol. 16, No. 7, pp. 523-537, 1983; D. A. Winter, "Biomechanical motor pattern in normal walking," Journal of Motor Behavior, Vol. 15, No. 4, pp. 302-330, 1983].

Although this passive-elastic behavior is a good approximation to the ankle's function during slow walking, normal and fast walking speeds require the addition of external energy, and thus cannot be implemented by any passive ankle-foot device [M. Palmer, "Sagittal plane characterization of normal human ankle function across a range of walking gait speeds," Master's Thesis, Massachusetts Institute of Technology, Cambridge, Mass., 2002; D. H. Gates, "Characterizing ankle function during stair ascent, descent, and level walking for ankle prosthesis and orthosis design," Master's Thesis, Boston University, 2004; A. H. Hansen, D. S. Childress, S. C. Miff, S. A. Gard, K. P. Mesplay, "The human ankle during walking: implication for the design of biomimetic ankle prosthesis," Journal of Biomechanics, Vol. 37, Issue 10, pp. 1467-1474, 2004]. This deficiency is reflected in the gait of transtibial amputees using passive ankle-foot prostheses. Their self-selected walking speed is slower, and stride length shorter, than normal [D. A. Winter and S. E. Sienko. "Biomechanics of below-knee amputee gait," Journal of Biomechanics, 21, pp. 361-367, 1988]. In addition, their gait is distinctly asymmetric: the range of ankle movement on the unaffected side is smaller [H. B. Skinner and D. J. Effeney, "Gait analysis in amputees," Am J Phys Med, Vol. 64, pp. 82-89, 1985; H. Bateni and S. Olney, "Kinematic and kinetic variations of below-knee amputee gait," Journal of Prosthetics & Orthotics, Vol. 14, No. 1, pp. 2-13, 2002], while, on the affected side, the hip extension moment is greater and the knee flexion moment is smaller [D. A. Winter and S. E. Sienko. "Biomechanics of below-knee amputee gait," Journal of Biomechanics, 21, pp. 361-367, 1988; H. Bateni and S. Olney, "Kinematic and kinetic variations of below-knee amputee gait," Journal of Prosthetics & Orthotics, Vol. 14, No. 1, pp. 2-13, 2002]. They also expend greater metabolic energy walking than non-amputees [N. H. Molen, "Energy/speed relation of below-knee amputees walking on motor-driven treadmill," Int. Z. Angew, Physio, Vol. 31, p 173, 1973; G. R. Colborne, S. Naumann, P. E. Longmuir, and D. Berbrayer, "Analysis of mechanical and metabolic factors in the gait of congenital below knee amputees," Am. J. Phys. Med. Rehabil., Vol. 92, pp 272-278, 1992; R. L. Waters, J. Perry, D. Antonelli, H. Hislop. "Energy cost of walking amputees: the influence of level of amputation," J Bone Joint Surg. Am., Vol. 58, No. 1, pp. 4246, 1976; E. G. Gonzalez, P. J. Corcoran, and L. R. Rodolfo. Energy expenditure in B/K amputees: correlation with stump length. Archs. Phys. Med. Rehabil. 55, 111-119, 1974; D. J. Sanderson and P. E. Martin. "Lower extremity kinematic and kinetic adaptations in unilateral below-knee amputees during walking," Gait and Posture. 6, 126-136, 1997; A. Esquenazi, and R. DiGiacomo. "Rehabilitation After Amputation," Journ Am Podiatr Med Assoc, 91(1): 13-22, 2001]. These differences could possibly be a result of the amputees' greater use of hip power to compensate for the lack of ankle power [A. D. Kuo, "Energetics of actively powered locomotion using the simplest walking model," J Biomech Eng., Vol. 124, pp. 113-120, 2002; A. D. Kuo, J. M. Donelan, and A. Ruina, "Energetic consequences of walking like an inverted pendulum: Step-sto-step transitions," Exerc. Sport Sci. Rev., Vol. 33, No. 2, pp. 88-97, 2005; A. Ruina, J. E. Bertram, and M. Srinivasan, "A collisional model of the energetic cost of support work qualitatively explains leg sequencing in walking and galloping, pseudo-elastic leg behavior in running and the walk-to-run transition." J. Theor. Biol., Vol. 237, No. 2, pp. 170-192, 2005].

Passive ankle-foot prostheses cannot provide the capability of adaptation to terrain. To provide for a normal, economical gait beyond slow walking speeds, powered ankle-foot prostheses have now been developed [S. Au and H. Herr. "Initial experimental study on dynamic interaction between an amputee and a powered ankle-foot prosthesis," Workshop on Dynamic Walking: Mechanics and Control of Human and Robot Locomotion, Ann Arbor, Mich., May 2006; S. K. Au, J. Weber, and H. Herr, "Biomechanical design of a powered ankle-foot prosthesis," Proc. IEEE Int. Conf. On Rehabilitation Robotics, Noordwijk, The Netherlands, pp. 298-303, June 2007; S. Au, J. Weber, E. Martinez-Villapando, and H. Herr. "Powered Ankle-Foot Prosthesis for the Improvement of Amputee Ambulation," IEEE Engineering in Medicine and Biology International Conference. August 23-26, Lyon, France, pp. 3020-3026, 2007; H. Herr, J. Weber, S. Au. "Powered Ankle-Foot Prosthesis," Biomechanics of the Lower Limb in Health, Disease and Rehabilitation. September 3-5, Manchester, England, pp. 72-74, 2007; S. K. Au, "Powered Ankle-Foot Prosthesis for the Improvement of Amputee Walking Economy," Ph.D. Thesis, Massachusetts Institute of Technology, Cambridge, Mass., 2007; S. Au, J. Weber, and H. Herr. "Powered Ankle-foot Prosthesis Improves Walking Metabolic Economy," IEEE Trans. on Robotics, Vol. 25, pp. 51-66, 2009; J. Hitt, R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp 2939-2945, May 2006; S. K. Au, H. Herr, "On the Design of a Powered Ankle-Foot Prosthesis: The Importance of Series and Parallel Elasticity," IEEE Robotics & Automation Magazine. pp. 52-59, September 2008]. Some of these are of size and weight comparable to the intact human ankle-foot, and have the elastic energy storage, motor power, and battery energy to provide for a day's typical walking activity [S. K. Au, H. Herr, "On the Design of a Powered Ankle-Foot Prosthesis: The Importance of Series and Parallel Elasticity," IEEE Robotics & Automation Magazine. pp. 52-59, September 2008].

The use of active motor power in these prostheses raises the issue of control. In previous work with these powered devices, the approach taken was to match the torque-ankle state profile of the intact human ankle for the activity to be performed [S. K. Au, "Powered Ankle-Foot Prosthesis for the Improvement of Amputee Walking Economy," Ph.D. Thesis, Massachusetts Institute of Technology, Cambridge, Mass., 2007; J. Hitt, R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom., Orlando, Fla., pp 2939-2945, May 2006; F. Sup, A. Bohara, and M. Goldfarb, "Design and Control of a Powered Transfemoral Prosthesis," The International Journal of Robotics Research, Vol. 27, No. 2, pp. 263-273, 2008]. The provision of motor power meant that the open work loops of the angle-torque profiles in faster walking could be supported, rather than just the spring-like behavior provided by passive devices. However, this control approach exhibited no inherent adaptation. Instead, torque profiles were required for all intended activities and variation of terrain, along with an appropriate means to select among them.

In general, existing commercially available active ankle prostheses are only able to reconfigure the ankle joint angle during the swing phase, requiring several strides to converge to a terrain-appropriate ankle position at first ground contact. Further, they do not provide any of the stance phase power necessary for normal gait, and therefore cannot adapt net stance work with terrain slope. In particular, control schemes for powered ankle-foot prostheses rely upon fixed torque-ankle state relationships obtained from measurements of intact humans walking at target speeds and across known terrains. Although effective at their intended gait speed and terrain, these controllers do not allow for adaptation to environmental disturbances such as speed transients and terrain variation.

Neuromuscular models with a positive force feedback reflex scheme as the basis of control have recently been employed in simulation studies of the biomechanics of legged locomotion [H. Geyer, H. Herr, "A muscle-reflex model that encodes principles of legged mechanics predicts human walking dynamics and muscle activities," (Submitted for publication); H. Geyer, A. Seyfarth, R. Blickhan, "Positive force feedback in bouncing gaits?," Proc. R Society. Lond. B 270, pp. 2173-2183, 2003]. Such studies show promise regarding the need for terrain adaptation.

SUMMARY OF THE INVENTION

In one aspect, the present invention is a controller and a control methodology for a biomimetic robotic leg based on a neuromuscular model of human locomotion. The control architecture commands biomimetic torques at the ankle, knee, and hip joints of a powered leg prosthesis, orthosis, or exoskeleton during walking. In a preferred embodiment, the powered device includes artificial ankle and knee joints that are torque controllable. Appropriate joint torques are provided to the user as determined by the feedback information provided by sensors mounted at each joint of the robotic leg device. These sensors include, but are not limited to, angular joint displacement and velocity using digital encoders, hall-effect sensors or the like, torque sensors at the ankle and knee joints, and at least one inertial measurement unit (IMU) located between the knee and the ankle joints.

Sensory information of joint state (position and velocity) from the robotic leg is used as inputs to a neuromuscular model of human locomotion. Joint state sensory information from the robotic leg is used to determine the internal state for each of its virtual muscles, and what the individual virtual muscle force and stiffness should be given particular levels of muscle activation is determined from a spinal reflex model. If the robotic leg is a leg prosthesis worn by a transfemoral amputee, angular sensors at the ankle and knee measure joint state for these joints. For the hip joint, the absolute orientation of the user's thigh is determined using both the angular joint sensor at the prosthetic knee and an IMU positioned between the prosthetic knee and the ankle joints. To estimate hip position and velocity, the control architecture works under the assumption that the upper body (torso) maintains a relative vertical position during gait.

In one aspect, the invention is a model-based neuromechanical controller for a robotic limb comprising at least one joint, the controller comprising a neuromuscular model including a muscle model, muscle tendon lever arm and muscle tendon length equations that define muscle geometry, and reflex control equations, the neuromuscular model being configured to receive feedback data relating to a measured state of the robotic limb and, using the feedback data, and the muscle model, muscle tendon lever arm and muscle tendon length equations and reflex control equations of the neuromuscular model, to determine at least one torque command, the controller further comprising a torque control system in communication with the neuromuscular model, whereby the torque control system receives the at least one torque command from the neuromuscular model for controlling the robotic limb joint. In a preferred embodiment, the feedback data is provided by at least one sensor mounted at each joint of the robotic limb. In another preferred embodiment, the robotic limb is a leg and the controller further includes a finite state machine synchronized to the leg gait cycle, the finite state machine being configured to receive the feedback data from the at least one sensor to determine a gait phase of the robotic leg using the feedback data received.

In another aspect, the invention is a model-based method for controlling a robotic limb comprising at least one joint, comprising the steps of receiving feedback data relating to the state of the robotic limb at a finite state machine, determining the state of the robotic limb using the finite state machine and the received feedback data, determining, using a neuromuscular model that includes muscle tendon lever arm and muscle tendon length equations and reflex control equations, and state information from the finite state machine, at least one desired joint torque or stiffness command to be sent to the robotic limb and commanding the biomimetic torques and stiffnesses determined by the muscle model processor at the robotic limb joint.

BRIEF DESCRIPTION OF THE DRAWINGS

Other aspects, advantages and novel features of the invention will become more apparent from the following detailed description of the invention when considered in conjunction with the accompanying drawings wherein:

FIGS. 2A-F depict six stages in the evolution of a general neuromuscular model architecture, according to one aspect of the present invention;

FIGS. 6A-D depict adaptation to walking up stairs, including snapshots of the model (FIG. 6A), net work (FIG. 6B), extensor muscle activation patterns (FIG. 6C), and the corresponding ground reaction force (FIG. 6D), according to one aspect of the present invention;

FIGS. 7A-D depict adaptation to walking down stairs, including snapshots of the model (FIG. 7A), net work (FIG. 7B), extensor muscle activation patterns (FIG. 7C), and the corresponding ground reaction force (FIG. 7D), according to one aspect of the present invention;

FIGS. 9A-C depict a contact model, according to one aspect of the present invention;

DETAILED DESCRIPTION

Figure 1:
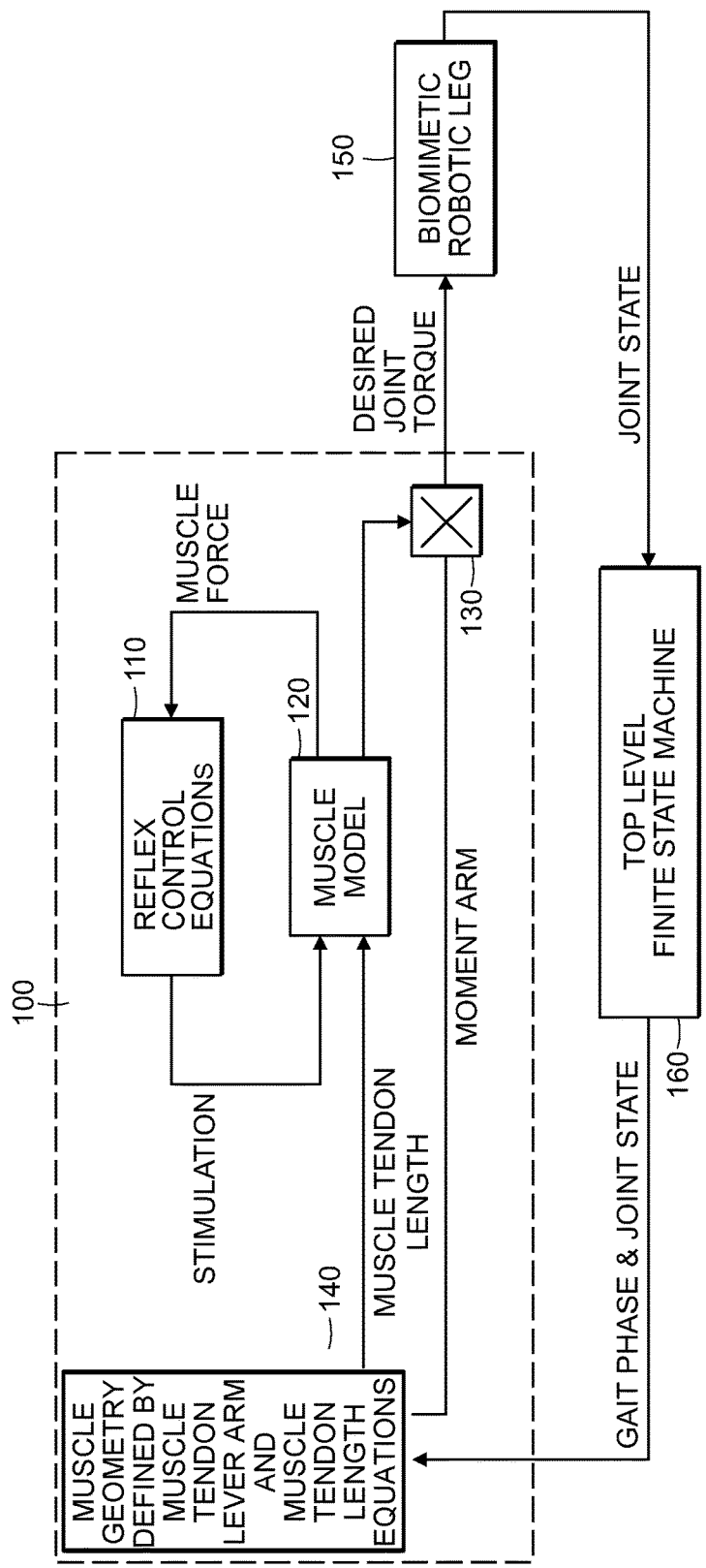
FIG. 1 is a block diagram of an exemplary embodiment of a general neuromuscular model architecture, according to one aspect of the present invention.

A control architecture is presented to command biomimetic torques at the ankle, knee, and hip joints of a powered leg prosthesis, orthosis, or exoskeleton during walking. In this embodiment, the powered device includes artificial ankle and knee joints that are torque controllable. Appropriate joint torques are provided to the user as determined by the feedback information provided by sensors mounted at each joint of the robotic leg device. These sensors include, but are not limited to, angular joint displacement and velocity using digital encoders, hall-effect sensors or the like, torque sensors at the ankle and knee joints and at least one inertial measurement unit (IMU) located between the knee and the ankle joints.

Sensory information of joint state (position and velocity) from the robotic leg (hip, knee and ankle) is used as inputs to a neuromuscular model of human locomotion. This model uses joint state sensory information from the robotic leg to determine the internal state for each of its virtual muscles, and establishes what the individual virtual muscle force and stiffness should be given particular levels of muscle activation determined from a spinal reflex model. If the robotic leg is a leg prosthesis worn by a transfemoral amputee, angular sensors at the ankle and knee measure joint state for these joints. For the hip joint, the absolute orientation of the user's thigh is determined using both the angular joint sensor at the prosthetic knee and an IMU positioned between the prosthetic knee and the ankle joints. To estimate hip position and velocity, the control architecture works under the assumption that the upper body (torso) maintains a relative vertical position during gait.

As used herein, and in the Appl.s incorporated by reference herein, the following terms expressly include, but are not to be limited to:

"Actuator" means a type of motor, as defined below.

"Agonist" means a contracting element that is resisted or counteracted by another element, the antagonist.

"Agonist-antagonist actuator" means a mechanism comprising (at least) two actuators that operate in opposition to one another: an agonist actuator that, when energized, draws two elements together and an antagonist actuator that, when energized, urges the two elements apart.

"Antagonist" means an expanding element that is resisted or counteracted by another element, the agonist.

"Biomimetic" means a man-made structure or mechanism that mimics the properties and behavior of biological structures or mechanisms, such as joints or limbs.

"Dorsiflexion" means bending the ankle joint so that the end of the foot moves upward.

"Elastic" means capable of resuming an original shape after deformation by stretching or compression.

"Extension" means a bending movement around a joint in a limb that increases the angle between the bones of the limb at the joint.

"Flexion" means a bending movement around a joint in a limb that decreases the angle between the bones of the limb at the joint.

"Motor" means an active element that produces or imparts motion by converting supplied energy into mechanical energy, including electric, pneumatic, or hydraulic motors and actuators.

"Plantarflexion" means bending the ankle joint so that the end of the foot moves downward.

"Spring" means an elastic device, such as a metal coil or leaf structure, which regains its original shape after being compressed or extended.

An exemplary embodiment of a neuromuscular model-based control scheme according to this aspect of the invention is shown as a block diagram in FIG. 1. In FIG. 1, a neuromuscular model 100 according to the invention includes reflex control equations 110 for each modeled muscle unit 120. The predicted forces and stiffnesses from all the modeled muscles are used to compute 130 model estimates of desired joint torques and stiffnesses using muscle moment arm values provided by muscle tendon lever arm and muscle tendon length equations that define muscle geometry 140, which determines moment arm and muscle tendon length values from joint state, e.g., joint angle, and data from the literature. A muscle tendon unit (MTU), also referred to a muscle tendon complex (MTC), and associated parameters, are described below with reference to FIGS. 8, 14 and 15. For the purposes of this description, MTU has the same meaning as MTC. The model estimates are then sent to torque control system of biomimetic robotic leg 150 as desired net torque and stiffness values for joints of biomimetic robotic leg 150. Top level finite state machine 160 then tracks the torque and stiffness values at each robotic joint of biomimetic robotic leg 150. Finite state machine 160 receives joint state as an input and provides gait phase and joint state as outputs to neuromuscular model 100.

In order for each of the virtual muscle to produce its required force, a muscle stimulation parameter STIM(t) is required. This parameter can be determined from either an outside input or a local feedback loop. In the control methodology for the exemplary biomimetic leg, the STIM(t)

is computed based on local feedback loops. This architecture is based on the reflex feedback framework developed by Geyer and Herr [H. Geyer, H. Herr, "A muscle-reflex model that encodes principles of legged mechanics predicts human walking dynamics and muscle activities," (Submitted for publication), herein incorporated by reference in its entirety]. In this framework the neural-control is designed to mimic the stretch reflex of an intact human muscle. This neuromuscular reflex-based control methodology allows the biomimetic robotic leg to replicate human-like joint mechanics.

Neuromechanical model. A human model with a reflex control that encodes principles of legged mechanics predicts human walking dynamics and muscle activities. While neuroscientists identify increasingly complex neural networks that control animal and human gait, biomechanists find that locomotion requires little motor control if principles of legged mechanics are heeded. Here it is shown how muscle reflex behavior could be vital to link these two observations. A model of human locomotion was developed that is driven by muscle reflex behaviors that encode principles of legged mechanics. Equipped with this principle-based reflex control, the model stabilizes into the walking gait from its dynamic interplay with the ground, tolerates ground disturbances, and self-adapts to stairs. Moreover, the model shows qualitative agreement with joint angles, joint torques and muscle activations known from experiments, suggesting that human motor output could largely be shaped by muscle reflex behaviors that link principles of legged mechanics into the neural networks responsible for locomotion.

A human walking model with a motor control is based on muscle reflexes, which are designed to include such principles of legged mechanics. These principles derive from simple conceptual models of legged locomotion and include the reliance on compliant leg behavior in stance [Blickhan, R., 1989. The spring-mass model for running and hopping. J. of Biomech. 22, 1217-1227; Ghigliazza, R., Altendorfer, R., Holmes, P., Koditschek, D., 2003. A simply stabilized running model. SIAM J. Applied. Dynamical Systems 2 (2), 187-218; Geyer, H., Seyfarth, A., Blickhan, R., 2006. Compliant leg behaviour explains the basic dynamics of walking and running. Proc. R. Soc. Lond. B 273, 2861-2867], the stabilization of segmented legs based on static joint torque equilibria [Seyfarth, A., Günther, M., Blickhan, R., 2001. Stable operation of an elastic three-segmented leg. Biol. Cybern. 84, 365-382; Günther, M., Keppler, V, Seyfarth, A., Blickhan, R., 2004. Human leg design: optimal axial alignment under constraints. J. Math. Biol. 48, 623-646], the exploitation of ballistic swing-leg mechanics [Mochon, S., McMahon, T., 1980. Ballistic walking. J. Biomech. 13 (1), 49-57], and the enhancement of gait stability using swing-leg retraction [Seyfarth, A., Geyer, H., Günther, M., Blickhan, R., 2002. A movement criterion for running. J. of Biomech. 35, 649-655; Seyfarth, A., Geyer, H., Herr, H. M., 2003. Swing-leg retraction: a simple control model for stable running. J. Exp. Biol. 206, 2547-2555]. Hill-type muscles combined with spinal reflexes are employed, including positive force and length feedback schemes, to effectively encode these mechanical features.

Comparing the model's behavior with kinetic, kinematic, and electromyographic evidence from the literature for human walking, it has been shown that a neuromuscular model with a motor control designed to encode principles of legged mechanics can produce biological walking mechanics and muscle activities. This reflex control allows the model to tolerate sudden changes in ground level and to adapt to stair ascent and descent without parameter interventions.

The structure and control of the human model evolves in six steps from a conceptual point-mass model into a neuromuscular biped with an upper body and two, three-segment legs each actuated by seven muscles and controlled by muscle reflexes. FIGS. 2A-F depict six stages in the evolution of a general neuromuscular model architecture, according to this aspect of the present invention. The first three stages integrate and stabilize compliant leg behavior in stance (FIG. 2A-C). The fourth stage adds an upper body and its balance control (FIG. 2D). The last two stages prepare and ensure the pro- and retraction of the legs during swing (FIGS. 2E and 2F).

In FIGS. 2A-F, described in more detail in the paragraphs that follow, evolving from a stance leg configuration (FIG. 2A), compliant leg behavior as key to walk and run is generated (FIG. 2B) by driving the soleus muscle (SOL) and the lumped vasti group muscles (VAS) with positive force feedbacks F+. To prevent knee overextension the biarticular gastrocnemius muscle (GAS) is added (FIG. 2C) using F+, and the VAS gets inhibited if the knee extends beyond a 170° threshold. To prevent ankle overextension, the tibialis anterior muscle (TA) is added whose pulling of the ankle joint into a flexed position by positive length feedback L+ is suppressed under normal stance conditions by negative force feedback F− from soleus. To allow leg swings, an upper body is added (FIG. 2D). It is driven into a reference lean with respect to the vertical by the hip flexor (HFL) and co-activated hip extensor muscles (GLU, HAM) of the stance leg, where the biarticular HAM prevents knee overextension resulting from hip extensor moments. The landing of the other (leading) leg initiates swing by adding/subtracting a constant stimulation to HFL/GLU, respectively, and by suppressing VAS proportionally to the load borne by the other leg (FIG. 2E). The actual leg swing is facilitated by HFL using L+ until it gets suppressed by L− of HAM (FIG. 2F). HFL's stimulation is biased dependent on the upper body's lean at take-off. Moreover, using F+ for GLU and HAM retracts and straightens the leg toward the end of swing. Finally, the now unsuppressed L+ of TA drives the ankle to a flexed position (FIG. 2G).

Stance leg compliance and stability. The bipedal spring-mass model is used as the starting point for the conceptual basis for human locomotion (FIG. 2A). Although this model consists only of point-mass 205 that progresses on two massless spring legs 210, 215, it reproduces the center of mass dynamics observed in human walking and running, unifying both gaits in one conceptual framework based on compliant leg behavior in stance [Geyer, H., Seyfarth, A., Blickhan, R., 2006. Compliant leg behaviour explains the basic dynamics of walking and running. Proc. R. Soc. Lond. B 273, 2861-2867].

To implement compliant behavior in neuromuscular legs, each spring 210, 215 is replaced with thigh 220, shank 225, and foot 230, and a soleus muscle (SOL) 235 and a vasti muscle group (VAS) 240 are added, both generating their muscle activity through local positive force feedback (F+) during the stance period of gait (FIG. 2B). This force reflex is modeled in the same way as in Geyer, H., Seyfarth, A., Blickhan, R., 2003. Positive force feedback in bouncing gaits? Proc. R. Soc. Lond. B 270, 2173-2183. Under positive force feedback, the stimulation $S_m(t)$ of a muscle m is the sum of a pre-stimulation $S_{0,m}$, and the muscle's time-delayed ($\Delta t$) and gained (G) force $F_m$: $S_m(t)=S_{0,m}+GF_m(t-\Delta t_m)$.

While compliant leg behavior is essential, it also threatens joint stability in segmented legs [Seyfarth, A., Günther, M., Blickhan, R., 2001. Stable operation of an elastic three-segmented leg. Biol. Cybern. 84, 365-382; Günther, M., Keppler, V, Seyfarth, A., Blickhan, R., 2004. Human leg design: optimal axial alignment under constraints. J. Math. Biol. 48, 623-646]. In segmented legs, the knee and ankle torques, $\tau_k$ and $\tau_a$, obey the static equilibrium $\tau_k/\tau_a = h_k/h_a$, where $h_k$ and $h_a$ are the perpendicular distances from the knee and the ankle to the leg force vector Fleg, respectively. In effect, a large extension torque at one joint forces the other joint closer to Fleg, threatening its overextension for spring-like behaving legs [for details see Seyfarth, A., Günther, M., Blickhan, R., 2001. Stable operation of an elastic three-segmented leg. Biol. Cybern. 84, 365-382].

This tendency to overextend at the knee or the ankle is countered by adding the gastrocnemius (GAS) 245 and tibialis anterior (TA) 250 muscles (FIG. 2C). Like SOL and VAS, the biarticular GAS uses local positive force feedback (F+) during the stance period of gait. This muscle reflex not only prevents knee hyperextension resulting from large extension torques at the ankle, but also contributes to generating an overall compliant leg behavior. In contrast, the monoarticular TA uses local positive length feedback (L+) with $S_{TA}(t) = S_{0,TA} + G_{TA}(l_{CE,TA} - l_{off,TA})(t - \Delta_{t,TA})$ where $l_{CE,TA}$ is the TA fiber length and $l_{off,TA}$ is a length offset. Flexing the foot, TA's L+ prevents the ankle from overextending when large knee torques develop. This muscle reflex is not required however if sufficient activity of the ankle extensor muscles preserves the torque equilibrium of knee and ankle. To avoid that TA unnecessarily fights SOL in this situation, the TA stimulation is inhibited with a negative force feedback (F−) from the SOL, resulting in $S_{TA}(t) = S_{0,TA} + G_{TA}(l_{CE,TA} - l_{off,TA})(t - \Delta_{t,TA}) - G_{SOLTA} F_{SOL}(t - \Delta t_{SOL})$. To further protect the knee from hyperextending, the VAS gets inhibited if the knee extends beyond a 170 deg threshold, $S_{VAS}(t) = S_{0,VAS} + G_{VAS} F_{VAS} (t - \Delta t_{VAS}) - k_\varphi \Delta \varphi_k (t - \Delta t_k)$, where $k_\varphi$ is a proportional gain, $\Delta \varphi_k = \varphi_k - 170$ deg, and $\varphi_k$ is the knee angle. This reflex inhibition is only active if $\Delta \varphi > 0$ and the knee is actually extending.

Upper body and its balance. In the next step of evolving from the conceptual spring-mass model into a neuromuscular biped, the point mass representation is discarded and an upper body 255 around which the legs can be swung (FIG. 2D) is introduced. This upper body 255 combines head, arms and trunk (HAT). To balance the HAT 255 during locomotion, to each leg is added a gluteus muscle group (GLU) 260 and a hip flexor muscle group (HFL) 265. The GLU 260 and the HFL 265 are stimulated with a proportional-derivative signal of the HAT's 255 forward lean angle θ with respect to gravity, $S_{GLU/HFL} \sim \pm [k_p (\theta - \theta_{ref}) + k_d d\theta/dt]$, where $k_p$ and $k_d$ are the proportional and derivative gains, and $\theta_{ref}$ is a reference lean angle [for similar approaches compare, for instance, Günther, M., Ruder, H., 2003. Synthesis of two-dimensional human walking: a test of the λ-model. Biol. Cybern. 89, 89-106]. Also included is the biarticular hamstring muscle group (HAM) 270 with $S_{HAM} \sim S_{GLU}$ to counter knee hyperextension that results from a large hip torque developed by the GLU 260 when pulling back the heavy HAT 255. Since hip torques can only balance the HAT 255 if the legs bear sufficient weight, the stimulations of the GLU 260, HAM 270, and HFL 265 are modulated for each leg proportionally to the amount of body weight it bears. As a result, each leg's hip muscles contribute to the HAT's balance control only during stance.

Swing leg pro- and retraction. The human model's structure is complete, except for a muscle-reflex control that produces swing leg pro- and retraction. It is assumed that a stance leg's functional importance reduces in proportion to the amount of body weight (bw) borne by the contralateral leg, and initiate swing leg protraction already in double support (FIG. 2E). The human model detects which leg enters stance last (contralateral leg), and suppresses F+ of the ipsilateral leg's VAS 240 in proportion to the weight the contralateral leg bears, $S_{VAS}(t) = S_{0,VAS} + G_{VAS} F_{VAS}(t - \Delta t_{VAS}) - k_\varphi \Delta \varphi_k (t - \Delta t_k) - k_{bw} |F_{leg}^{contra}|$. The contralateral suppression allows the knee to break its functional spring behavior, and flex while the ankle extends, pushing the leg off the ground and forward. While this catapult mechanism can initiate swing only if the ankle pushes sufficiently, the model further prepares swing leg protraction by increasing the stimulation of the HFL 265, and decreasing that of the GLU 260, by a fixed amount ΔS in double support.

During actual swing, the main reliance is on a leg's ballistic motion, but it is influenced in two ways (FIG. 2F). On one hand, protraction of the swing leg is facilitated. The HFL 265 is stimulated using positive length feedback (L+) biased by the forward pitch angle $\theta_{ref}$ of the HAT 255 at the stance-to-swing transition, $S_{HFL}(t) = S_{0,HFL} + k_{lean} (\theta - \theta_{ref})_{TO} + G_{HFL}(l_{CE,HFL} - l_{off,HFL})(t - \Delta_{t,HFL})$. Using this approach, it is ensured that the swing leg's ballistic motion gains the momentum to bring it forward in time [Mochon, S., McMahon, T., 1980. Ballistic walking. J. Biomech. 13 (1), 49-57].

Furthermore, the swing leg is also prevented from overreaching and its retraction is ensured. If legs reach and maintain a proper orientation during swing, legged systems self-stabilize into a gait cycle [McGeer, T., 1990. Passive dynamic walking. Int. J. Rob. Res. 9 (2), 62-82; Seyfarth, A., Geyer, H., Günther, M., Blickhan, R., 2002. A movement criterion for running. J. of Biomech. 35, 649-655; Ghigliazza, R., Altendorfer, R., Holmes, P., Koditschek, D., 2003. A simply stabilized running model. SIAM J. Applied. Dynamical Systems 2 (2), 187-218; Geyer, H., Seyfarth, A., Blickhan, R., 2006. Compliant leg behaviour explains the basic dynamics of walking and running. Proc. R. Soc. Lond. B 273, 2861-2867]. The tolerance of this mechanical self-stability against disturbances can largely be enhanced if swing legs additionally retract before landing [Seyfarth, A., Geyer, H., 2002. Natural control of spring-like running—optimized self-stabilization. In: Proceedings of the 5th international conference on climbing and walking robots. Professional Engineering Publishing Limited, pp. 81-85; Seyfarth, A., Geyer, H., Herr, H. M., 2003. Swing-leg retraction: a simple control model for stable running. J. Exp. Biol. 206, 2547-2555]. To implement this halt-and-retract strategy, three muscle reflexes are included in the human model. The overreaching of the swing leg that would result from the forward impulse the leg receives when the knee reaches full extension during protraction is prevented. Hereto, the HFL's L+ is inhibited proportional to the stretch which the HAM receives in swing, $S_{HFL}(t) = k_{lean} (\theta - \theta_{ref}) TO + G_{HFL}(l_{CE,HFL} - l_{off,HFL})(t - \Delta_{t,HFL}) - G_{HAMHFL}(l_{CE,HAM} - l_{off,HAM})(t - \Delta_{t,HAM})$. In addition, F+ is used for the GLU, $S_{GLU}(t) = S_{0,GLU} + G_{GLU} F_{GLU}(t - \Delta t_{GLU})$, and for the HAM, $S_{HAM}(t) = S_{0,HAM} + G_{HAM} F_{HAM} (t - \Delta t_{HAM})$, to ensure that, dependent on the actual protraction momentum, the swing leg not only halts, but also transfers part of this momentum into leg straightening and retraction. Finally, the TA L+ introduced to ensure foot clearance is kept throughout the swing. The SOL, GAS, and VAS remain silent during this phase.

Reflex control parameters. The different reflex contributions to the muscle stimulations Sm(t) are governed through the equations used in the model. No parameter optimization was performed. Parameters were derived from previous knowledge of reflex behavior (F+, L+) or by making plausible estimates. All muscle stimulations are limited in range from 0.01 to 1 before being translated into muscle activations $A_m(t)$. Table 1 presents the stance reflex equations used in the preferred embodiment.

TABLE 1

$$S_{SOL}(t) = S_{0,SOL} + G_{SOL}F_{SOL}(t_1)$$
$$= 0.01 + 1.2/F_{max,SOL}F_{SOL}(t_1)$$

$$S_{TA}(t) = S_{0,TA} + G_{TA}[\ell_{CE,TA}(t_1) - \ell_{off,TA}] - G_{SOL,TA}F_{SOL}(t_1)$$
$$= 0.01 + 1.1[\ell_{CE,TA}(t_1) - 0.71\ell_{opt,TA}] - 0.3/F_{max,SOL}F_{SOL}(t_1)$$

$$S_{GAS}(t) = S_{0,GAS} + G_{GAS}F_{GAS}(t_1)$$
$$= 0.01 + 1.1/F_{max,GAS}F_{GAS}(t_1)$$

$$S_{VAS}(t) = S_{0,VAS} + G_{VAS}F_{VAS}(t_m) - k_\varphi[\varphi_k(t_m) - \varphi_{k,off}][\varphi_k(t_m) > \varphi_{k,off}]$$
$$[d\varphi_k/dt(t_m) > 0] - k_{bw}|F_{leg}^{contra}(t_s)|^*DSup$$
$$= 0.09 + 1.15/F_{max,VAS}F_{VAS}(t_m) - 1.15[\varphi_k(t_m) - 2.97][\varphi_k(t_m) > 2.97]$$
$$[d\varphi_k/dt(t_m) > 0] - 0.00167|F_{leg}^{contra}(t_s)|^*DSup$$

$$S_{HAM}(t) = S_{0,HAM} + \{k_p[\theta(t_s) - \theta_{ref}] + k_d d\theta/dt(t_s)\} + k_{bw}|F_{leg}^{ipsi}(t_s)|$$
$$= 0.05 + \{1.9[\theta(t_s) - 0.105] + 0.25d\theta/dt(t_s)\} + 0.00167|F_{leg}^{ipsi}(t_s)|$$

$$S_{GLU}(t) = S_{0,GLU} + \{k_p[\theta(t_s) - \theta_{ref}] + k_d d\theta/dt(t_s)\} + k_{bw}|F_{leg}^{ipsi}(t_s)| - 0.25^*DSup$$
$$= 0.05 + \{1.3[\theta(t_s) - 0.105] + 0.25d\theta/dt(t_s)\} + 0.00167|F_{leg}^{ipsi}(t_s)| - 0.25^*DSup$$

$$S_{HFL}(t) = S_{0,HFL} + \{k_p[\theta(t_s) - \theta_{ref}] + k_d d\theta/dt(t_s)\} - k_{bw}|F_{leg}^{ipsi}(t_s)| + \Delta S^*DSup$$
$$= 0.05 + \{1.9[\theta(t_s) - 0.105] + 0.25d\theta/dt(t_s)\} - 0.00167|F_{leg}^{ipsi}(t_s)| - 0.25^*DSup$$

($t_1 = t - 20$ ms, $t_m = t - 10$ ms, and $t_s = t - 5$ ms, DSup is 1 if leg is trailing leg in double support, otherwise 0,
$\{\}_{+/-}$ refers to only positive/negative values)

Table 2 presents the swing reflex equations used in the preferred embodiment.

TABLE 2

$$S_{SOL}(t) = S_{0,SOL}$$
$$= 0.01$$

$$S_{TA}(t) = S_{0,TA} + G_{TA}[\ell_{CE,TA}(t_1) - \ell_{off,TA}]$$
$$= 0.01 + 1.1[\ell_{CE,TA}(t_1) - 0.71\ell_{opt,TA}]$$

$$S_{GAS}(t) = S_{0,GAS}$$
$$= 0.01$$

$$S_{VAS}(t) = S_{0,VAS}$$
$$= 0.01$$

$$S_{HAM}(t) = S_{0,HAM} + G_{HAM}F_{HAM}(t_s)$$
$$= 0.01 + 0.65/F_{max,HAM}F_{HAM}(t_s)$$

$$S_{GLU}(t) = S_{0,GLU} + G_{GLU}F_{GLU}(t_s)$$
$$= 0.01 + 0.4/F_{max,GLU}F_{GLU}(t_s)$$

TABLE 2-continued $$S_{HFL}(t) = S_{0,HFL} + GH_{FL}[\ell_{CE,HFL}(t_s) - \ell_{off,HFL}] - G_{HAM,HFL}[\ell_{CE,HAM}(t_s) - \ell_{off,HAM}] +$$

$$\{k_{lean}[\theta(t_s) - \theta_{ref}]\}PTO$$

$$= 0.01 + 0.35[\ell_{CE,HFL}(t_s) - 0.6\ell_{opt,HFL}] - 4[\ell_{CE,HAM}(t_s) - 0.85\ell_{opt,HAM}] +$$

$$\{1.15[\theta(t_s) - 0.105]\}PTO$$

({ }PTO: constant value taken at previous take off.)

Figure 3:
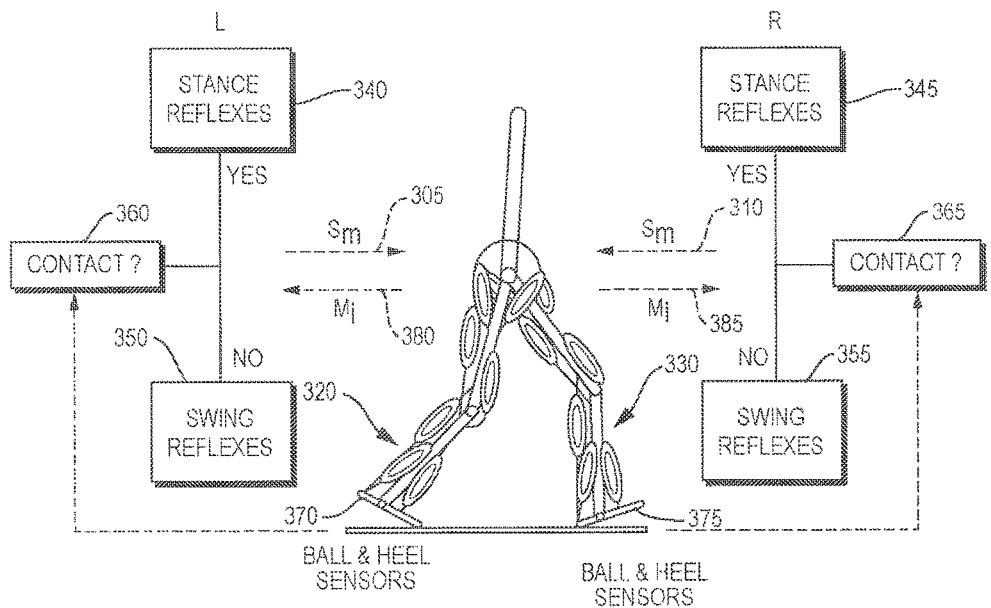
FIG. 3 graphically depicts pattern generation, according to one aspect of a general neuromuscular model architecture according to the present invention.

Results. Although the human model has no central pattern generator (CPG) that feed-forwardly activates its muscles, it switches for each leg between the different reflexes for stance and swing using sensors located at the ball and heel of each foot to detect ground. As a result, the model's dynamic interaction with its mechanical environment becomes a vital part of generating muscle activities. FIG. 3 graphically depicts pattern generation according to this aspect of the invention. In FIG. 3, instead of a central pattern, reflexes generate the muscle stimulations, $S_m$ 305, 310. Left (L) 320 and right (R) 330 leg have separate stance 340, 345 and swing 350, 355 reflexes, which are selected based on contact sensing 360, 365 from ball and heel sensors 370, 375. The reflex outputs depend on mechanical inputs, $M_i$ 380, 385, intertwining mechanics and motor control.

Figure 4A:
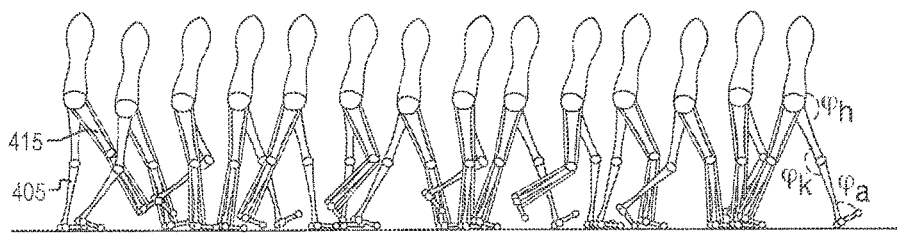
FIGS. 4A and 4B depict walking of a human model self-organized from dynamic interplay between model and ground, and the corresponding ground reaction force, respectively, according to one aspect of the present invention.
Figure 4B:
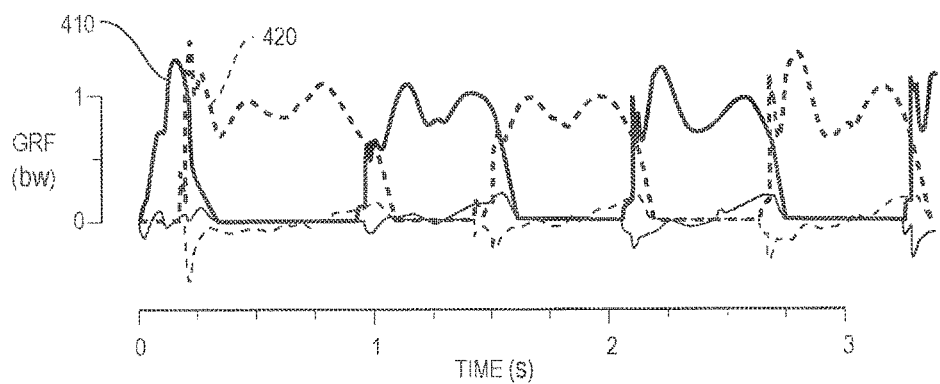

Walking gait. To study how important this interdependence of mechanics and motor control can be to human locomotion, the model was started with its left leg in stance and its right leg in swing at a normal walking speed v0=1.3 ms−1. Since the modeled muscle reflexes include time delays of up to 20 ms, all muscles are silent at first. FIGS. 4A and 4B depict walking of a human model self-organized from dynamic interplay between model and ground and the corresponding ground reaction force, respectively, according to one aspect of the present invention. In FIGS. 4A and 4B, snapshots of human model taken every 250 ms (FIG. 4A) and corresponding model GRF (FIG. 4B) are shown, with separate plots for left 405, 410 and right 415, 420 legs (30 Hz low-pass filtered). Starting with a horizontal speed of 1.3 ms$^{-1}$, the model slows down in the first two steps, but then rapidly recovers into walking at the same speed. Leg muscles are shown only for the right leg 415, indicating muscle activation >10%. Initial conditions for $\varphi_{a,k,h}$ (definition of ankle, knee and hip angle) for each leg were: $\varphi_{a,k,h}$=85 deg, 175 deg, 175 deg (left leg) and $\varphi_{a,k,h}$=90 deg, 175 deg, 140 deg (right leg).

Because of these disturbed initial conditions, the model slightly collapses and slows down in its first step (FIG. 4A). If its parameters are chosen properly, however, the model rapidly recovers in the following steps, and walking self-organizes from the dynamic interplay between model and ground. Here the vertical ground reaction force (GRF) of the legs in stance shows the M-shape pattern characteristic for walking gaits (FIG. 4B), indicating similar whole-body dynamics of model and humans for steady state walking.

Figures 5A, 5B, 5C:
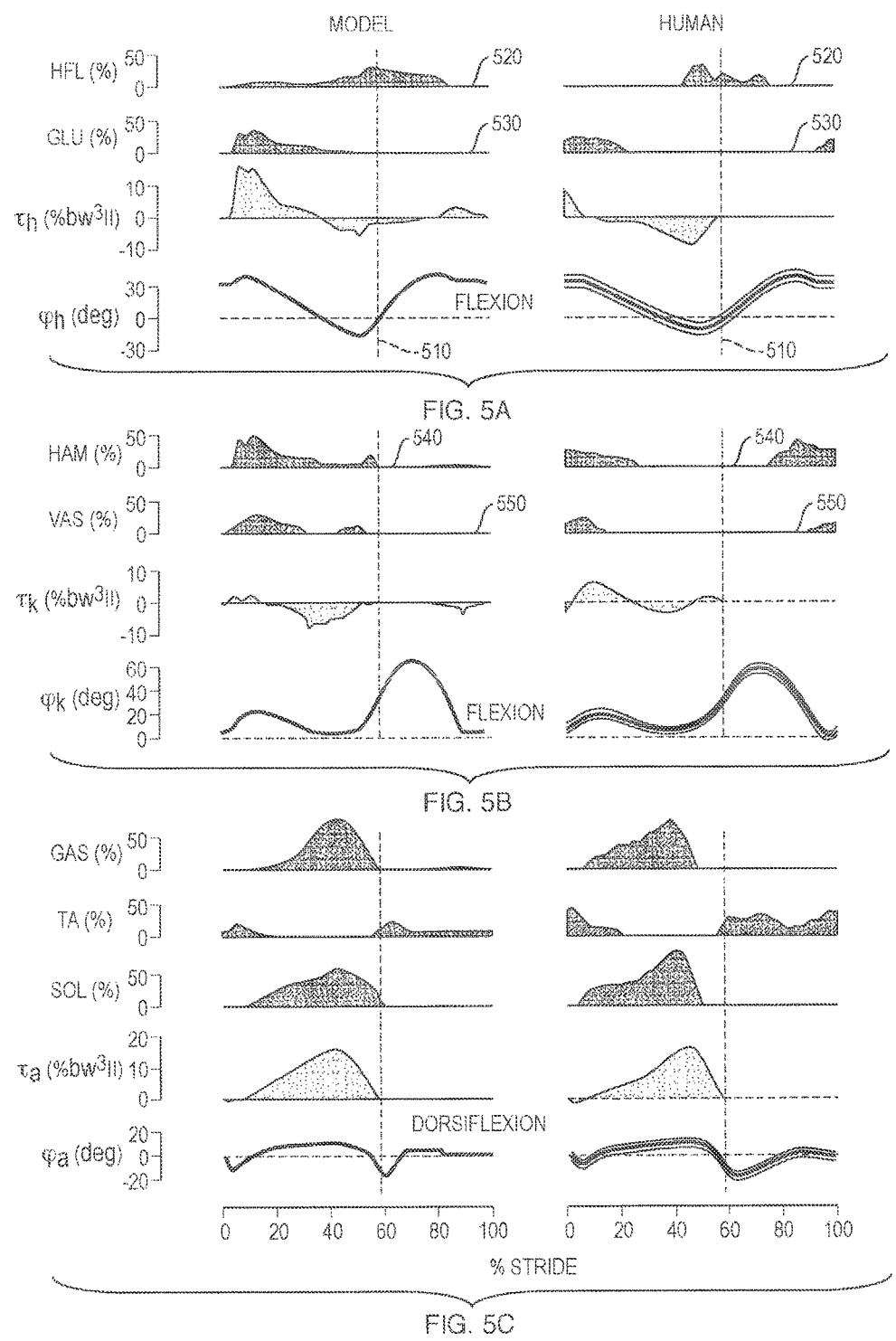
FIGS. 5A-C compare steady state walking for the model and a human subject for hip, knee, and ankle, respectively, according to one aspect of the present invention.

Steady-state patterns of angles, torques and muscle activations. This similarity also holds upon closer inspection; the model shows qualitative agreement with angle, torque and muscle activation patterns known from human walking data. FIGS. 5A-C compare steady state walking at 1.3 ms$^{-1}$ for the model and a human subject for hip (FIG. 5A), knee (FIG. 5B), and ankle (FIG. 5C), respectively, according to one aspect of the present invention. In FIGS. 5A-C, normalized to one stride from heel-strike to heel-strike of the same leg, the model's steady-state patterns of muscle activations, torques, and angles of hip, knee and ankle are compared to human walking data (adapted from Perry, 1992). Vertical dotted lines 510 around 60% of stride indicate toe off. Compared muscles are adductor longus (HFL) 520, upper gluteus maximum (GLU) 530, semimembranosis (HAM) 540, and vastus lateralis (VAS) 550.

The strongest agreement between model prediction and walking data can be found at the ankle (FIG. 5C). The reflex model not only generates ankle kinematics $\varphi_a$ and torques $\tau_a$ observed for the human ankle in walking, but also predicts SOL, TA and GAS activities that resemble the experimental SOL, TA and GAS activities as inferred from their surface electromyographs. For SOL and GAS, this activity is generated exclusively by their local F+ reflexes in stance. For TA, its L+ reflex responds with higher activity to plantar flexion of the foot in early stance, but gets suppressed by F− from SOL during the remainder of that phase. Only when SOL activity reduces at the transition from stance to swing (60% of stride), does the TA's L+ resume, pulling the foot against plantar flexion.

The comparison shows a weaker agreement for the knee and the hip. For instance, although the general trajectory $\varphi_k$ of the human knee is captured by the model, its knee flexes about 10 degree or 30% more than the human's in early stance (FIG. 5B). Related to this larger knee flexion, the model lacks the observed VAS activity in late swing that continues into early stance. Only after heel-strike, the F+ of VAS engages and can activate the muscle group in response to the loading of the leg. The delay in extensor activities causes not only a relatively weak knee in early stance, but also the heavy HAT to tilt forward after impact. Since the balance control of the HAT engages gradually with the weight borne by the stance leg, the balance reflexes are silent until heel-strike and then must produce unnaturally large GLU and HAM activities to return the HAT to its reference lean (FIG. 5C). Hence, the model's hip trajectory $\varphi_h$ and torque pattern $\tau_h$ least resemble that of humans whose hip extensors GLU and HAM are active before impact and can prevent such an exaggerated tilt of the trunk.

Self-adaptation to ground changes. Despite its limited reflex control, the human model tolerates sudden, and self-adapts to permanent, changes of the ground level. FIGS. 6A-D show an example in which the model encounters a sequence of stairs going up 4 cm each. FIGS. 6A-D depict adaptation to walking up stairs, including snapshots of the model (FIG. 6A), net work (FIG. 6B), extensor muscle activation patterns (FIG. 6C), and the corresponding ground reaction force (FIG. 6D), according to one aspect of the present invention. In FIGS. 6A-D, approaching from steady-state walking at 1.3 ms$^{-1}$, eight strides of the human model are shown covering five steps of 4 cm incline each. The model returns to steady-state walking on the 8th stride. One stride is defined from heel-strike to heel-strike of the right leg. Shown in FIG. 6A are snapshots of the model at heel-strike and toe-off of the right leg. For this leg are further shown, in FIG. 6B, the net work during stance generated at hip, knee and ankle with positive work being extension work; in FIG. 6C, the activation patterns of the five extensor muscles of each stride; and, in FIG. 6D, the corresponding ground reaction forces 650 normalized to body weight (bw), with ground reaction forces of the left leg 660 are included for comparison.

Approaching from steady-state walking (1st stride), the model hits the stairs at the end of the 2nd stride with the foot of its outstretched right leg (FIG. 6A). This early impact slows down the model and tilts the upper body forward, which is countered by a large hip torque generated by the GLU and HAM (3rd stride, FIGS. 6B and 6C). Since hip extension torques tend to also extend the knee, the VAS does not feel as much force as in steady-state and its force feedback control lowers its muscle stimulation (FIG. 6C), even though the net work at the knee during stance remains about the same as in steady state. In contrast, the slow down of the model reduces the force the ankle extensors GAS and SOL feel during stance, and their force feedback reflexes produce slightly less muscle stimulation, lowering the net work of the ankle (FIGS. 6B and 6C). In strides 4 and 5 the model settles into upstair walking at about 1 ms$^{-1}$ where the forward and upward thrust is generated mainly at the hip and knee. After reaching the plateau in the 6th stride, the model recovers into its original steady-state walking speed of 1.3 ms$^{-1}$ in the 8th stride.

FIGS. 7A-D depict adaptation to walking down stairs, including snapshots of the model (FIG. 7A), net work (FIG. 7B), extensor muscle activation patterns (FIG. 7C), and the corresponding ground reaction force (FIG. 7D), according to one aspect of the present invention. In FIGS. 7A-D, approaching from steady-state walking at 1.3 ms$^{-1}$, eight strides of the human model are shown covering five steps of 4 cm incline each. The model returns to steady-state walking on the 8th stride. One stride is defined from heel-strike to heel-strike of the right leg. Shown in FIG. 7A are snapshots of the model at heel-strike and toe-off of the right leg. For this leg are further shown, in FIG. 7B, the net work during stance generated at hip, knee and ankle with positive work being extension work; in FIG. 7C, the activation patterns of the five extensor muscles of each stride; and, in FIG. 7D, the corresponding ground reaction forces 750 normalized to body weight (bw), with ground reaction forces of the left leg 760 are included for comparison. The model returns to steady state walking at 1.3 ms$^{-1}$ in the 14th stride after covering five steps down with 4 cm decline each.

FIGS. 7A-D continues the walking sequence with the model encountering stairs going down. At the end of the 9th stride, the model hits the first step down with its right foot (FIG. 7A). The downward motion accelerates the model and results in an overall larger first impact of the right leg in the 10th stride with a stronger response of most extensor muscles (FIGS. 7C and 7D). Only the GAS generates less force, because the knee stays more flexed than usual in this stride. As a result, positive net work at the ankle increases substantially (FIG. 7B). This increase and a larger HFL stimulation (not shown) caused by the forward lean of the upper body at its take-off (FIG. 7A) propel the right leg forward in swing increasing the step length (FIG. 7A). After the transitional 10th stride, the model keeps the larger step length in the downward motion (strides 11 and 12), where the model's downward acceleration is countered by increased activity of the GLU, HAM and VAS immediately following impact (FIGS. 7C and 7D), which reduces net positive work at the hip and increases net negative work at the knee (FIG. 7B), and stabilizes the model into walking down at about 1.5 ms$^{-1}$. Back on level ground, the lack of downward acceleration slows down the model, which automatically reduces its step length (FIG. 7A) and drives it back into steady-state walking at 1.3 ms$^{-1}$ within the 13th and 14th step.

For both walking up and down stairs, no single control is responsible. The key to the model's tolerance and adaptation are its dynamic muscle-reflex responses. The rebound of the stance leg depends on how much load the leg extensors SOL, GAS and VAS feel, which guarantees that the leg yields sufficiently to allow forward progression when going up, but brakes substantially when going down. On the other hand, the forward propulsion of the swing leg varies with the model dynamics. Sudden deceleration after impact of the opposite leg, forward lean of the upper body, and ankle extension rate near the end of stance-all contribute to leg propulsion in swing. These combined features ensure that the swing leg protracts enough in upstair walking and substantially in downstair walking. For the latter, the force feedbacks of GLU and HAM constrain excess rotations of the leg and instead force it to rapidly retract and straighten.

Figure 8:
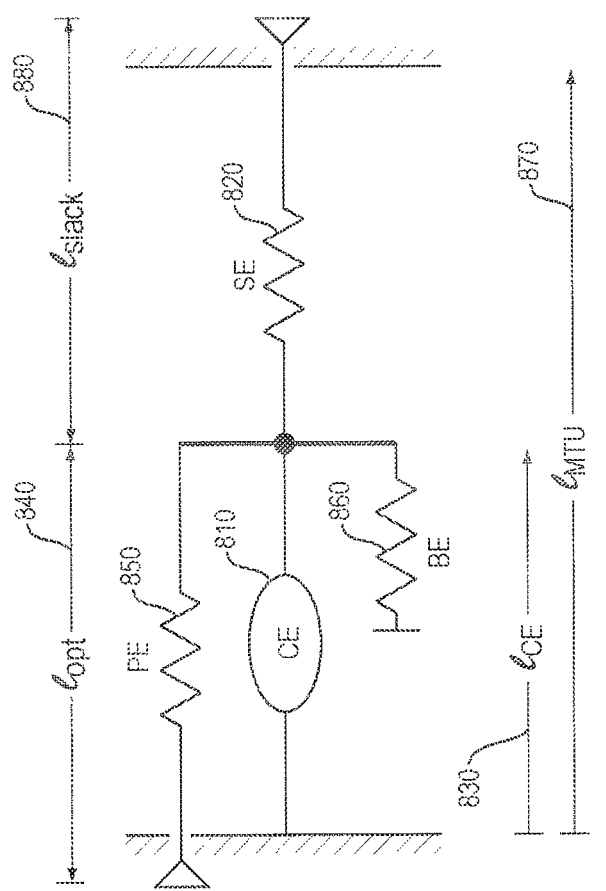
FIG. 8 is a schematic of a muscle-tendon model, according to one aspect of the present invention.

Muscle tendon units. All 14 muscle-tendon units (MTUs) of the biped have the same model structure. FIG. 8 is a schematic of a muscle-tendon model, according to one aspect of the present invention. In FIG. 8, active, contractile element (CE) 810 together with series elasticity (SE) 820 form the muscle-tendon unit (MTU) in normal operation. If CE 810 stretches beyond its optimum length $l_{CE}$ 830 ($l_{CE}$>$l_{opt}$ 840), parallel elasticity (PE) 850 engages. Conversely, buffer elasticity (BE) 860 prevents the active CE 810 from collapsing if SE 820 is slack ($l_{MTU}$ 870–$l_{CE}$ 830<$l_{slack}$ 880).

As seen in FIG. 8, an active, Hill-type contractile element (CE) produces force in line with a series elasticity (SE). Although the MTUs are fitted into the skeleton such that the individual CEs operate mainly on the ascending limb of their force-length relationship, the MTU model includes a parallel elasticity (PE), which engages if the CE stretches beyond its optimum length $t_{opt}$. In addition, a buffer elasticity (BE) ensures that the CE cannot collapse when the geometry of the leg shortens the MTU so much that it becomes slack. Note that BE is merely a numerical tool that allows the MTU to describe a slack muscle, for instance, a slack GAS when the knee overly flexes. BE does however not result in forces outside the MTU.

Table 3 presents individual MTU parameters. All parameters are estimated from Yamaguchi et al. [Yamaguchi, G. T., Sawa, A. G.-U., Moran, D. W., Fessler, M. J., Winters, J. M., 1990. A survey of human musculotendon actuator parameters. In: Winters, J., Woo, S.-Y. (Eds.), Multiple Muscle Systems: Biomechanics and Movement Organization. Springer-Verlag, New York, pp. 717-778]. The maximum isometric forces $F_{max}$ are estimated from individual or grouped muscle-physiological cross-sectional areas assuming a force of 25N per cm$^{-2}$. The maximum contraction speeds $v_{max}$ are set to 6 $l_{opt}$ s$^{-1}$ for slow muscles and to 12 $l_{opt}$ s$^{-1}$ for medium fast muscles. The optimum CE lengths $l_{opt}$ and the SE slack lengths $l_{slack}$ reflect muscle fiber and tendon lengths.

TABLE 3

|  | SOL | TA | GAS | VAS | HAM | GLU | HFL |
|---|---|---|---|---|---|---|---|
| $F_{max}$ (N) | 4000 | 800 | 1500 | 6000 | 3000 | 1500 | 2000 |
| $v_{max}$ ($\ell_{opt}$ s$^{-1}$) | 6 | 12 | 12 | 12 | 12 | 12 | 12 |

TABLE 3-continued

|  | SOL | TA | GAS | VAS | HAM | GLU | HFL |
|---|---|---|---|---|---|---|---|
| $\ell_{opt}$ (cm) | 4 | 6 | 5 | 8 | 10 | 11 | 11 |
| $\ell_{slack}$ (cm) | 26 | 24 | 40 | 23 | 31 | 13 | 10 |

Details on how CE and SE were modeled can be found in Geyer et al. [Geyer, H., Seyfarth, A., Blickhan, R., 2003. Positive force feedback in bouncing gaits? Proc. R. Soc. Lond. B 270, 2173-2183]. The force of the CE, $F_{CE}=A F_{max} f_l (l_{CE}) f_v (v_{CE})$, is a product of muscle activation A, CE force-length relationship $f_l (l_{CE})$, and CE force-velocity relationship $f_v (v_{CE})$. Based on this product approach, the MTU dynamics are computed by integrating the CE velocity $v_{CE}$, which is found by inverting $f_v (v_{CE})$. Given that $F_{SE}=F_{CE}+FP_E-F_{BE}$, $f_v (V_{CE})=(F_{SE}-F_{PE}+F_{BE})/(A F_{max} f_l(l_{CE}))$. This equation has a numerically critical point during muscle stretch when $F_{SE}-F_{PE}$ approaches zero. To speed up simulations, this critical point is avoided by introducing $f_v (v_{CE})$ into the force production of the parallel elasticity $F_{PE} \sim (l_{CE}-l_{opt})^2 f_v (v_{CE})$. Note that PE engages outside the normal range of operation in the model, and like BE, plays a minor role for the muscle dynamics during normal locomotion. With this approach, however, $f_v (v_{CE})=(F_{SE}+F_{BE})/(A F_{max} f_l (l_{CE})+F_{PE})$ is obtained, which can numerically be integrated using coarse time steps. While this approach is convenient to speed up the model simulation, it was also critical when muscle dynamics were emulated on PC boards with fixed and limited time resolution.

The MTUs have common and individual parameters. The common parameters include the time constant of the excitation contraction coupling, $t_{ecc}=0.01$; the CE force-length relationship's width, $w=0.56 l_{opt}$, and residual force factor, $c=0.05$; the CE force-velocity relationship's eccentric force enhancement, $N=1.5$, and shape factor, $K=5$; and the SE reference strain, $\varepsilon_{ref}=0.04$ [for details, see Geyer, H., Seyfarth, A., Blickhan, R., 2003. Positive force feedback in bouncing gaits? Proc. R. Soc. Lond. B 270, 2173-2183]. Also common parameters are the PE reference strain $\varepsilon_{PE}=w$ where $F_{PE}=F_{max} (l_{CE}/l_{opt}-1)^2/\varepsilon_{PE}^2 f_v (v_{CE})$, and the BE rest length $l_{min}=l_{opt}-w$ and its reference compression $\varepsilon_{BE}=w/2$ where $F_{BE}=F_{max} [(l_{min}-l_{CE})/l_{opt}]^2/\varepsilon_{PE}^2$. The individual MTU attachment parameters are readily available from the literature and distinguish each muscle or muscle group. Their values are listed in Table 4.

$\Delta l_m = \rho r(\varphi-\varphi_{ref})$ for the hip. The reference angle $\varphi_{ref}$ is the joint angle where $l_m=l_{opt}+l_{slack}$. The factor $\rho$ accounts for muscle pennation angles and ensures that an MTU's fiber length stays within physiological limits throughout the working range of the joint. The specific parameters for each muscle and joint are listed in Table 4. These values are either supported by experimental evidence [Muraoka, T., Kawakami, Y., Tachi, M., Fukunaga, T., 2001. Muscle fiber and tendon length changes in the human vastus lateralis during slow pedaling. J. Appl. Physiol. 91, 2035-2040; Maganaris, C., 2001. Force-length characteristics of in vivo human skeletal muscle. Acta Physiol. Scand. 172, 279-285; Maganaris, C., 2003. Force-length characteristics of the in vivo human gastrocnemius muscle. Clin. Anat. 16, 215-223; Oda, T., Kanehisa, H., Chino, K., Kurihara, T., Nagayoshi, T., Kato, E., Fukunaga, T., Kawakami, Y, 2005. In vivo length-force relationships on muscle fiver and muscle tendon complex in the tibialis anterior muscle. Int. J. Sport and Health Sciences 3, 245-252], or were obtained through rough anatomical estimates.

The seven segments of the human model are simple rigid bodies whose parameters are listed in Table 5. Their values are similar to those used in other modeling studies, for instance, in Günther and Ruder [Günther, M., Ruder, H., 2003. Synthesis of two-dimensional human walking: a test of the λ-model. Biol. Cybern. 89, 89-106]. The segments are connected by revolute joints. As in humans, these joints have free ranges of operation ($70°<\varphi_a<130°$, $\varphi_k<175°$ and $\varphi_h<230°$) outside of which mechanical soft limits engage, which is modelled in the same way as the ground impact points. The model's segments have different masses $m_S$ and lengths $l_S$, and characteristic distances of their local center of mass, $d_{G,S}$, and joint location, $d_{J,S}$ (measured from distal end), and inertias $\Theta_S$.

TABLE 5

|  | Feet | Shanks | Thighs | HAT |
|---|---|---|---|---|
| $l_S$ (cm) | 20 | 50 | 50 | 80 |
| $d_{G,S}$ (cm) | 14 | 30 | 30 | 35 |
| $d_{J,S}$ (cm) | 16 | 50 | 50 | — |
| $m_S$ (cm) | 1.25 | 3.5 | 8.5 | 53.5 |
| $\Theta_S$ (kgm2) | 0.005 | 0.05 | 0.15 | 3 |

TABLE 4

| MTU attachment parameters | | | | | | | | |
|---|---|---|---|---|---|---|---|---|
| | ankle | | | knee | | | hip | |
| | SOL | TA | GAS | GAS | VAS | HAM | HAM | GLU | HFL |
| $r_0$ (cm) | 5 | 4 | 5 | 5 | 6 | 5 | 8 | 10 | 10 |
| $\varphi_{max}$ (deg) | 110 | 80 | 110 | 140 | 165 | 180 | — | — | — |
| $\varphi_{ref}$ (deg) | 80 | 110 | 80 | 165 | 125 | 180 | 155 | 150 | 180 |
| $\rho$ | 0.5 | 0.7 | 0.7 | 0.7 | 0.7 | 0.7 | 0.7 | 0.5 | 0.5 |

Musculoskeletal connections and mass distribution. The MTUs connect to the skeleton by spanning one or two joints. The transfer from muscle forces $F_m$ to joint torques $\tau_m$ is modeled using variable lever arms $r_m(\varphi)=r_0 \cos(\varphi-\varphi_{max})$ for the ankle and knee where $\varphi$ is the joint angle, $\varphi_{max}$ is the angle at which $r_m$ reaches its maximum, and $\tau_m=r_m(\varphi)F_m$. For the hip, it is simply assumed that $r_m(\varphi)=r_0$. On the other hand, changes $\Delta l_m$ in MTU lengths are modeled as $\Delta l_m=\rho r [\sin(\varphi-\varphi_{max})-\sin(\varphi_{ref}-\varphi_{max})]$ for the ankle and knee; and as Ground contacts and joint limits. Each foot segment of the bipedal model has contact points at its toe and heel. When impacting the ground, a contact point (CP) gets pushed back by a vertical reaction force $F_y=-F_{ref} f_1 f_v$, which, like the muscle force, is the product of a force-length relationship $f_1$ ($\Delta y_{CP})=\Delta y_{CP}/\Delta y_{ref}$ and a force-velocity relationship $f_v$ ($dy_{CP}/dt)=1-dy_{CP}/dt/v_{max}$ (FIG. 9). This product approach to modeling vertical reaction forces is similar to existing approaches that describe the vertical force as the sum of a spring and a nonlinear spring-damper term [Scott, S., Winter, D., 1993. Biomechanical model of the human foot: kinematics and kinetics during the stance phase of walking. J. Biomech. 26 (9), 1091-1104; Gerritsen, K., van den Bogert, A., Nigg, B., 1995. Direct dynamics simulation of the impact phase in heel-toe running. J. Biomech. 28 (6), 661-668; Günther, M., Ruder, H., 2003. Synthesis of two-dimensional human walking: a test of the λ-model. Biol. Cybern. 89, 89-106]. By separating spring and damper terms, however, the parameters of the contact model can be interpreted as two basic material properties: a ground stiffness $k=F_{ref}/\Delta y_{ref}$ and a maximum relaxation speed $v_{max}$, which characterizes how quickly the ground surface can restore its shape after being deformed. For instance, $v_{max}=\infty$ describes a perfectly elastic ground impact where the ground always pushes back against the CP, and $v_{max}=0$ describes a perfectly inelastic impact where the ground, like sand, pushes back on the CP for downward velocities, but cannot push back for upward velocities. Note that the same impact model is used to describe the mechanical soft limits of the model's joints (see previous section) with a soft limit stiffness of 0.3N m deg$^{-1}$ and a maximum relaxation speed of 1 deg s$^{-1}$.

FIGS. 9A-C depict a contact model, according to one aspect of the present invention. In FIGS. 9A-C, contact occurs 910 if contact point 920 falls below $y_0$. The vertical ground reaction force $F_y$ is, like the muscle force, modeled as the product of a force-length ($f_l$) and a force-velocity relationship ($f_v$) with $\Delta y_{ref}$ being the ground compression at which $F_y=F_{ref}$ when dy/dt=0, and $dy_{ref}/dt$ being the maximum relaxation speed of the ground (small diagrams). Initially, the horizontal ground reaction force $F_x$ is modeled as sliding friction proportional to Fy with sliding coefficient $\mu_{sl}$. If however contact point 920 slows down 930 to below a minimum speed $v_{lim}$, the horizontal model switches to stiction 930. During stiction 930, $F_x$ is also modeled as the product of force-length and force-velocity relationships, which slightly differ from those earlier in order to allow for interactions with the ground in both directions around the stiction reference point $x_0$. The model switches back to sliding friction if $F_x$ exceeds the stiction limit force $\mu_{st} F_y$. Parameters: $F_{ref}$=815N, $\Delta y_{ref}$=0.01 m, $dy_{ref}/dt$=0.03 ms$^{-1}$, $\Delta x_{ref}$=0.1 m, $dx_{ref}/dt$=0.03 ms$^{-1}$, $v_{lim}$=0.01 ms$^{-1}$, $\mu_{s1}$=0.8, $\mu_{st}$=0.9.

In addition to the vertical reaction force, a horizontal reaction force is applied to the CP during ground contact. Initially, this force is modeled as a kinetic friction force that opposes the CP's motion on the ground with a force $F_x=\mu_{sl} F_y$. When the CP slows down to below a speed $v_{lim}$, the horizontal reaction force is modelled as a stiction force computed in a manner similar to that in which the vertical impact force is computed (FIGS. 9A-C). Stiction changes back to kinetic friction if the stiction force exceeds a limit force $F_{lim}=\mu_{st} F_y$. Thus, dependent on the transition conditions, both types of horizontal reaction force interchange until the CP leaves the ground surface.

The results suggest that mechanics and motor control cannot be viewed separately in human locomotion. A neuromuscular model of human locomotion according to one aspect of the invention self-organizes into the walking gait after an initial push, tolerates sudden changes in ground level, and adapts to stair walking without interventions. Central to this model's tolerance and adaptiveness is its reliance on muscle reflexes, which integrate sensory information about locomotion mechanics into the activation of the leg muscles. Having no CPG, the model shows that in principle no central input is required to generate walking motions, suggesting that reflex inputs that continuously mediate between the nervous system and its mechanical environment may even take precedence over central inputs in the control of normal human locomotion.

In addition, the model results suggest that these continuous reflex inputs encode principles of legged mechanics. Current experimental and modeling research on the role of spinal reflexes during locomotion focuses on their contribution to the timing of swing and stance phases and to the production of muscle force in load bearing extensor muscles [Pang, M. Y., Yang, J. F., 2000. The initiation of the swing phase in human infant stepping: importance of hip position and leg loading. J Physiol 528 Pt 2, 389-404; Dietz, V, 2002. Proprioception and locomotor disorders. Nat Rev Neurosci 3 (10), 781-790; Ivashko, D. G., Prilutski, B. I., Markin, S. N., Chapin, J. K., Rybak, I. A., 2003. Modeling the spinal cord neural circuitry controlling cat hindlimb movement during locomotion. Neurocomputing 52-54, 621-629; Yakovenko, S., Gritsenko, V, Prochazka, A., 2004. Contribution of stretch reflexes to locomotor control: a modeling study. Biol Cybern 90 (2), 146-155; Ekeberg, O., Pearson, K., 2005. Computer simulation of stepping in the hind legs of the cat: an examination of mechanisms regulating the stance-to-swing transition. J Neurophysiol 94 (6), 4256-4268; Maufroy, C., Kimura, H., Takase, K., 2008. Towards a general neural controller for quadrupedal locomotion. Neural Netw 21(4), 667-681; Donelan, J. M., Pearson, K. G., 2004. Contribution of sensory feedback to ongoing ankle extensor activity during the stance phase of walking. Can J Physiol Pharmacol 82 (8-9), 589-598; Frigon, A., Rossignol, S., 2006. Experiments and models of sensorimotor interactions during locomotion. Biol Cybern 95 (6), 607-627; Grey, M. J., Nielsen, J. B., Mazzaro, N., Sinkjaer, T., 2007. Positive force feedback in human walking. J Physiol 581 (1), 99-105]. The reflex contribution to load bearing has started to link positive force feedback to the underlying dynamics of the locomotor system [Prochazka, A., Gillard, D., Bennett, D., 1997. Positive force feedback control of muscles. J. of Neurophys. 77, 3226-3236; Geyer, H., Seyfarth, A., Blickhan, R., 2003. Positive force feedback in bouncing gaits? Proc. R. Soc. Lond. B 270, 2173-2183]. There appears to be no previous work that systematically expands on the idea of encoding principles of legged dynamics in the motor control system. While some of the muscle reflexes implemented in the human model were simple expedients to let it enter cyclic motions (trunk balance, swing-leg initiation), mainly the stance phase reflexes encoded principles of legged dynamics and control described previously, including compliant stance leg behavior [Blickhan, R., 1989. The spring-mass model for running and hopping. J. of Biomech. 22, 1217-1227; McMahon, T., Cheng, G., 1990. The mechanism of running: how does stiffness couple with speed? J. of Biomech. 23, 65-78; Geyer, H., Seyfarth, A., Blickhan, R., 2006. Compliant leg behaviour explains the basic dynamics of walking and running. Proc. R. Soc. Lond. B 273, 2861-2867], stabilization of segmented chains [Seyfarth, A., Günther, M., Blickhan, R., 2001. Stable operation of an elastic three-segmented leg. Biol. Cybern. 84, 365-382; Günther, M., Keppler, V, Seyfarth, A., Blickhan, R., 2004. Human leg design: optimal axial alignment under constraints. J. Math. Biol. 48, 623-646], and swing-leg retraction [Herr, H., McMahon, T., 2000. A trotting horse model. Int. J. Robotics Res. 19, 566-581; Herr, H., McMahon, T., 2001. A galloping horse model. Int. J. Robotics Res. 20, 26-37; Herr, H. M., Huang, G. T., McMahon, T. A., April 2002. A model of scale effects in mammalian quadrupedal running. J Exp Biol 205 (Pt 7), 959-967; Seyfarth, A., Geyer, H., 2002. Natural control of spring-like running—optimized self-stabilization. In: Proceedings of the 5th international conference on climbing and walking robots. Professional Engineering Publishing Limited, pp. 81-85; Seyfarth, A., Geyer, H., Herr, H. M., 2003. Swing-leg retraction: a simple control model for stable running. J. Exp. Biol. 206, 2547-2555]. Based on these functional reflexes, the model not only converges to known joint angle and torque trajectories of human walking, but also predicts some individual muscle activation patterns observed in walking experiments. This match between predicted and observed muscle activations suggests that principles of legged mechanics could play a larger role in motor control than anticipated before, with muscle reflexes linking these principles into the neural networks responsible for locomotion.

In a preferred embodiment, the neuromechanical model of the invention has been implemented as a muscle reflex controller for a powered ankle-foot prosthesis. This embodiment is an adaptive muscle-reflex controller, based on simulation studies, that utilizes an ankle plantar flexor comprising a Hill-type muscle with a positive force feedback reflex. The model's parameters were fitted to match the human ankle's torque-angle profile as obtained from level-ground walking measurements of a weight and height-matched intact subject walking at 1 m/sec. Using this single parameter set, clinical trials were conducted with a transtibial amputee walking on level ground, ramp ascent, and ramp descent conditions. During these trials, an adaptation of prosthetic ankle work was observed in response to ground slope variation, in a manner comparable to intact subjects, without the difficulties of explicit terrain sensing. Specifically, the energy provided by the prosthesis was directly correlated to the ground slope angle. This study highlights the importance of neuromuscular controllers for enhancing the adaptiveness of powered prosthetic devices across varied terrain surfaces.

In order to produce a controller with the ability to adapt, the neuromuscular model with a positive force feedback reflex scheme as the basis of control of the invention was used as part of the control system for a powered ankle-foot prosthesis. The controller presented here employs a model of the ankle-foot complex for determining the physical torque to command at the ankle joint. In this model, the ankle joint is provided with two virtual actuators. For plantar flexion torque, the actuator is a Hill-type muscle with a positive force feedback reflex scheme. This scheme models the reflexive muscle response due to some combination of afferent signals from muscle spindles and Golgi tendon organs. For dorsiflexion torque, an impedance is provided by a virtual rotary spring-damper.

The parameters of this neuromuscular model were fitted by an optimization procedure to provide the best match between the measured ankle torque of an intact subject walking at a target speed of 1.0 m/sec, and the model's output torque when given as inputs the measured motion of the intact subject. The neuromuscular model-based prosthetic controller was used to provide torque commands to a powered ankle-foot prosthesis worn by an amputee. This control strategy was evaluated using two criteria. First, the controller was tested for the ability to produce prosthesis ankle torque and ankle angle profiles that qualitatively match those of a comparable, intact subject at a target level-ground walking speed. The second performance criterion was the controller's ability to exhibit a biologically-consistent trend of increasing gait cycle net-work for increasing walking slope without changing controller parameters. Detecting variations in ground slope is difficult using typical sensors, so a controller with an inherent ability to adapt to these changes is of particular value.

Figure 10A:
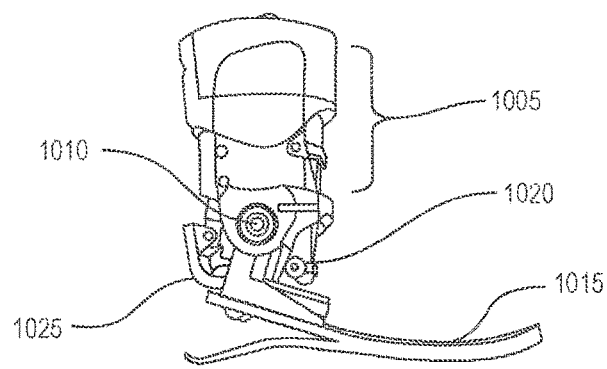
FIGS. 10A-C depict an exemplary embodiment of an ankle-foot prosthesis used in a preferred embodiment, depicting the physical system (FIG. 10A), a diagram of the drive train (FIG. 10B), and a mechanical model (FIG. 10C), respectively, according to one aspect of the present invention.
Figure 10B:
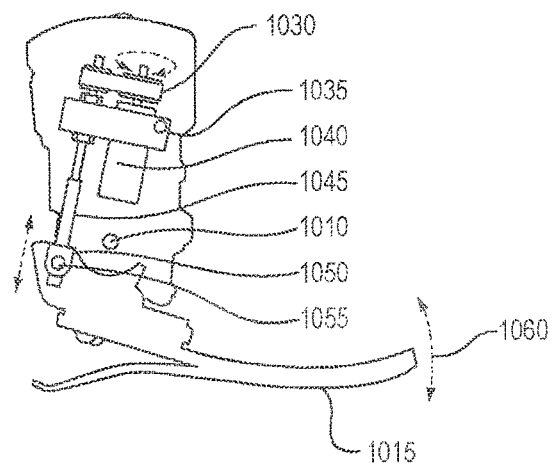
Figure 10C:
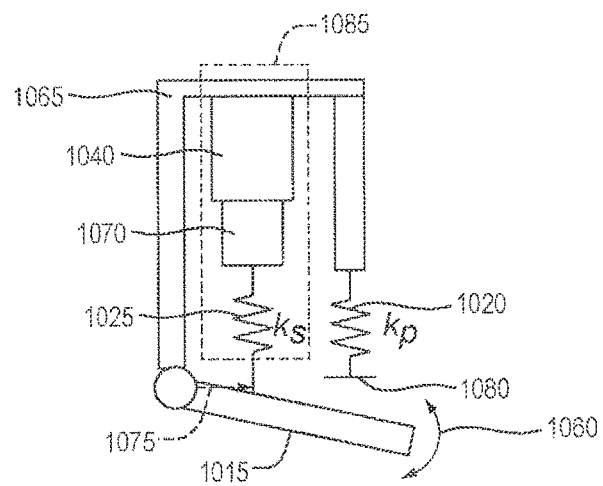

FIGS. 10A-C depict the physical system (FIG. 10A), a diagram of the drive train (FIG. 10B), and a mechanical model (FIG. 10C) for an exemplary embodiment of an ankle-foot prosthesis used in a preferred embodiment. The ankle-foot prosthesis used for this study is one in development by iWalk, LLC. This prosthesis is a successor to the series of prototypes developed in the Biomechatronics Group of the MIT Media Laboratory, which are described in U.S. patent application Ser. No. 12/157,727, filed Jun. 12, 2008, the entire disclosure of which has been incorporated by reference herein in its entirety. The prosthesis is a completely self-contained device having the weight (1.8 kg) and size of the intact biological ankle-foot complex. Seen in FIG. 10A are housing 1005 for the motor, transmission, and electronics, ankle joint 1010, foot 1015, unidirectional parallel leaf spring 1020, and series leaf spring 1025. Depicted in FIG. 10B are timing belt 1030, pin joint main housing 1035, motor 1040, ball screw 1045, ankle joint 1010, ball nut 1050 pin joint (series spring) 1055, and foot motion indicator 1060. Depicted in the mechanical model of FIG. 10C are parent link 1065, motor 1040, transmission 1070, series spring 1025, unidirectional parallel spring 1020, foot 1015, series spring movement arm $r_s$ 1075, spring rest length 1080, and SEA 1085. The rotary elements in the physical system are shown as linear equivalents in the model schematic for clarity.

The ankle joint is a rolling bearing design joining a lower foot structure to an upper leg shank structure topped with a prosthetic pyramid fixture for attachment to the amputee's socket. The foot includes a passive low profile Flex-Foot™ (Osur™) to minimize ground contact shock to the amputee. A unidirectional leaf spring, the parallel spring, acts across the ankle joint, engaging when the ankle and foot are perpendicular to each other. It acts in parallel to a powered drive train, providing the passive function of an Achilles tendon. The powered drive train is a motorized link across the ankle joint as represented in FIG. 10B. From the upper leg shank end, it consists, in series, of a brushless motor, (Powermax EC-30, 200 Watt, 48V, Maxon) operating at 24V, a belt drive transmission with 40/15 reduction, and a 3 mm pitch linear ball screw. At this operating voltage, the theoretical maximum torque that can be generated by the motor through the drivetrain is approximately 340 Nm.

At the foot, the series spring, a Kevlar-composite leaf spring, connects the foot to the ball nut with a moment arm, $r_s$, that is direction-dependent. Therefore, the effective rotary stiffness of the series spring, as evaluated by locking the drive train and exerting a torque about the ankle joint, is 533 N·m/rad for positive torque, and 1200 N·m/rad for negative torque, where positive torque (or plantar flexion torque) is that tending to compress the series spring as represented in FIG. 10C. The drive train and the series spring together comprise a series-elastic actuator (SEA) [G. A. Pratt and M. M. Williamson, "Series elastic actuators," Proceedings on IEEE/RSJ International Conference on Intelligent Robots and Systems, Pittsburgh, pp. 399-406, 1995]. The arrangement of these components is shown schematically in FIG. 10C.

Sensors. A hall-effect angle sensor at the ankle joint is a primary control input, and has a range of −0.19 to 0.19 radians, where zero corresponds to the foot being perpendicular to the shank. Joint angle is estimated with a linear hall-effect sensor (Allegro A1395) mounted on the main housing. This sensor is proximate to a magnet that is rigidly connected to the foot structure so that the magnetic axis is tangent to the arc of the magnet's motion. As a result of this arrangement, the magnetic field strength at the sensor location varies as the magnet rotates past the sensor. Strain gauges are located inside the prosthetic pyramid attachment, allowing for an estimate of the torque at the ankle joint. Strain gauges located on the series spring permit sensing of the output torque of the motorized drive train, thereby allowing for closed-loop force control of the SEA. The motor itself contains Hall-effect commutation sensors and is fitted with an optical shaft encoder that enables the use of advanced brushless motor control techniques.

Microcontroller. Overall control and communications for the ankle-foot prosthesis are provided by a single-chip, 16-bit, DSP oriented microcontroller, the Microchip Technology Incorporated dsPIC33FJ128MC706. The microcontroller operates at 40 million instructions per second, with 128 kilo-bytes of flash program memory, and 16384 bytes of RAM. It provides adequate computation to support real time control.

Motor Controller. A second 16-bit dsPIC33FJ128MC706 was used as a dedicated motor controller. The high computation load and speed requirements of modern brushless motor control methodologies, along with task isolation from the main microcontroller's real time demands motivated this architecture. A high speed digital link between the main microcontroller and the motor microcontroller supplied virtually instantaneous command of the motor.

Wireless Interface. For development and data collection, a high speed serial port of the microcontroller is dedicated to external communications. This port may be used directly via cable or may have a wide variety of wireless communication devices attached. For the present study, the 500 Hz sensor and internal state information is telemetered over the serial port at 460 Kilobaud and transmitted via an IEEE 802.11g wireless local area network device (Lantronix Wiport).

Battery. All power for the prosthesis was provided by a 0.22 kg lithium polymer battery having a 165 Watt-Hour/kg energy density. The battery was able to provide a day's power requirements including 5000 steps of powered walking.

Optimal Mechanical Component Selection. Meeting the requirements for mass, size, torque, speed, energy efficiency, shock tolerance, and nearly silent operation is not a trivial task. Of particular importance is the modeling and optimization of the drive train for the production of the biological torques and motions of walking. Some effects of the motor selection, overall transmission ratio, series elastic spring, and parallel spring are described in S. K. Au, H. Herr, "On the Design of a Powered Ankle-Foot Prosthesis: The Importance of Series and Parallel Elasticity," IEEE Robotics & Automation Magazine. pp. 52-59, September 2008.

Control Architecture. The purpose of the control architecture is to command an ankle torque appropriate to the amputee's gait cycle as determined from available sensor measurements of prosthetic ankle state. The controller determines the appropriate torque using a neuromuscular model of the human ankle-foot complex. In this model, a hinge joint, representing the human ankle joint, is actuated by two competing virtual actuators: a unidirectional plantar flexor which is a Hill-type muscle model, and a dorsiflexor which acts as either a bi-directional proportional-derivative position controller, or a unidirectional virtual rotary spring-damper, depending on the gait phase. A finite state machine maintains an estimate of the phase of the amputee's gait. Depending on this estimated gait phase, one or the other, or both of the virtual actuators produce torques at the virtual ankle joint. The net virtual torque is then used as the ankle torque command to the prosthesis hardware. Physical torque at the ankle joint is produced by both the motorized drive train and the parallel spring. The ankle angle sensor is used to determine the torque produced by the parallel spring, and the remaining desired torque is commanded through the motor controller.

Figure 11:
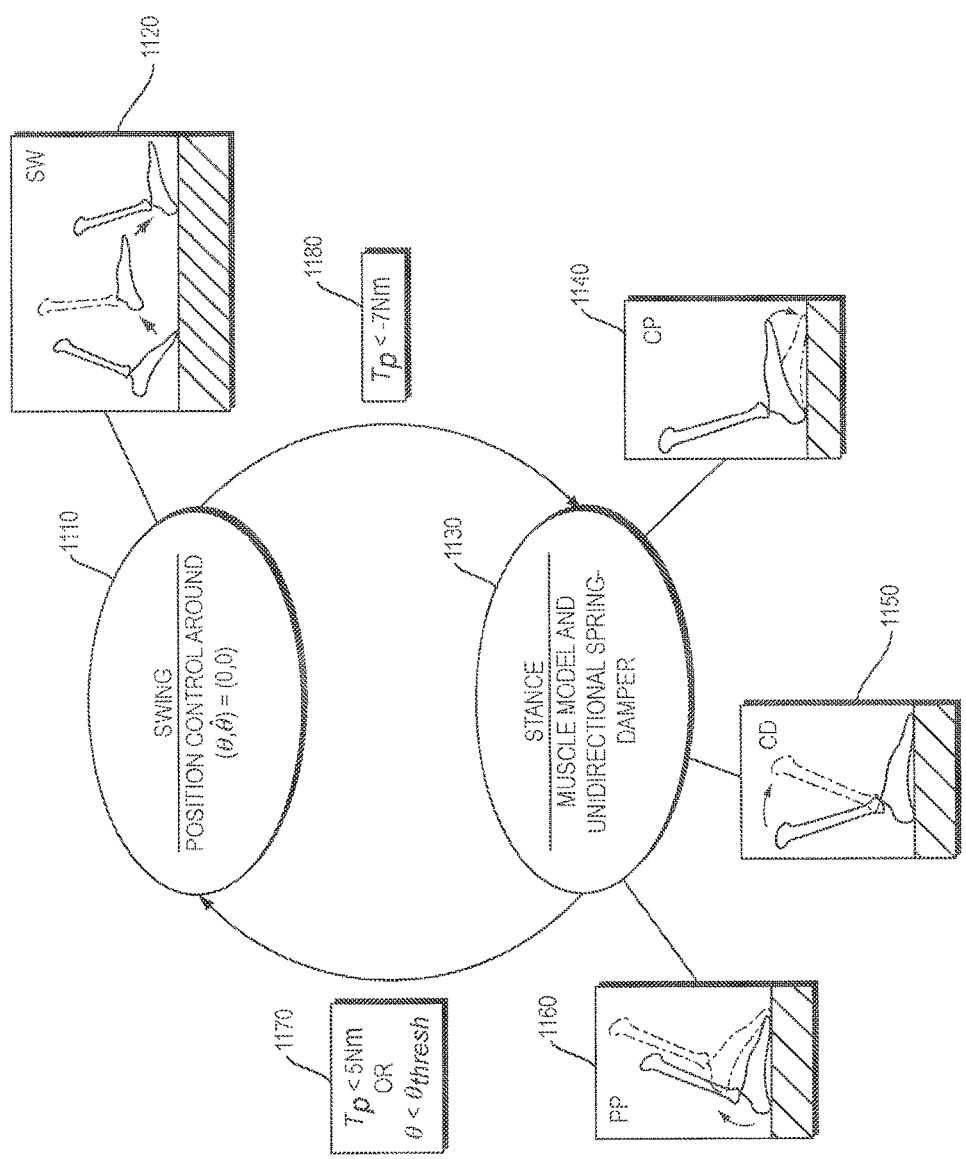
FIG. 11 is a diagram of an exemplary embodiment of a finite state machine synchronized to the gait cycle, with state transition thresholds and equivalent ankle-foot biomechanics during each state, used to implement top level control of the ankle-foot prosthesis of FIGS. 10A-C, according to one aspect of the present invention.

Top Level State Machine Control. Top level control of the prosthesis is implemented by a finite state machine synchronized to the gait cycle. During walking, two states are recognized: swing phase and stance phase. Prosthesis sensor inputs (ankle torque as estimated from the pyramid strain gauges, ankle angle, and motor velocity) are continuously observed to determine state transitions. Conditions for these state transitions were experimentally determined. FIG. 11 depicts the operation of the state machine and the transition conditions. The dorsiflexor and plantar flexor virtual actuators develop torque depending on the gait state estimate from the state machine.

In FIG. 11, the swing state 1110 is visually depicted as SW 1120, and stance 1130 is divided into controlled plantar flexion (CP) 1140, controlled dorsiflexion (CD) 1150, and powered plantar flexion (PP) 1160. State transitions 1170, 1180 are determined using the prosthesis ankle torque, $T_P$, as measured from the pyramid strain gauges, and prosthesis ankle angle, $\theta$.

The transition to swing phase when the foot leaves the ground is detected by either a drop in total ankle torque to less than 5 N·m, as measured using the pyramid strain gauges, or a drop in measured ankle angle, $\theta$, below −0.19 radians to prevent angle sensor saturation. Positive torque is defined as actuator torque tending to plantar flex the ankle, and positive angles correspond to dorsiflexion. To prevent premature state transitions, the ankle torque developed during the stance phase must exceed 20 Nm for these transitions to be enabled. In addition, a 200 ms buffer time provides a minimum time frame for the stance period. The transition to stance phase upon heel-strike is detected by a decrease in torque below −7 N·m as measured using the pyramid strain gauges.

Figure 12:
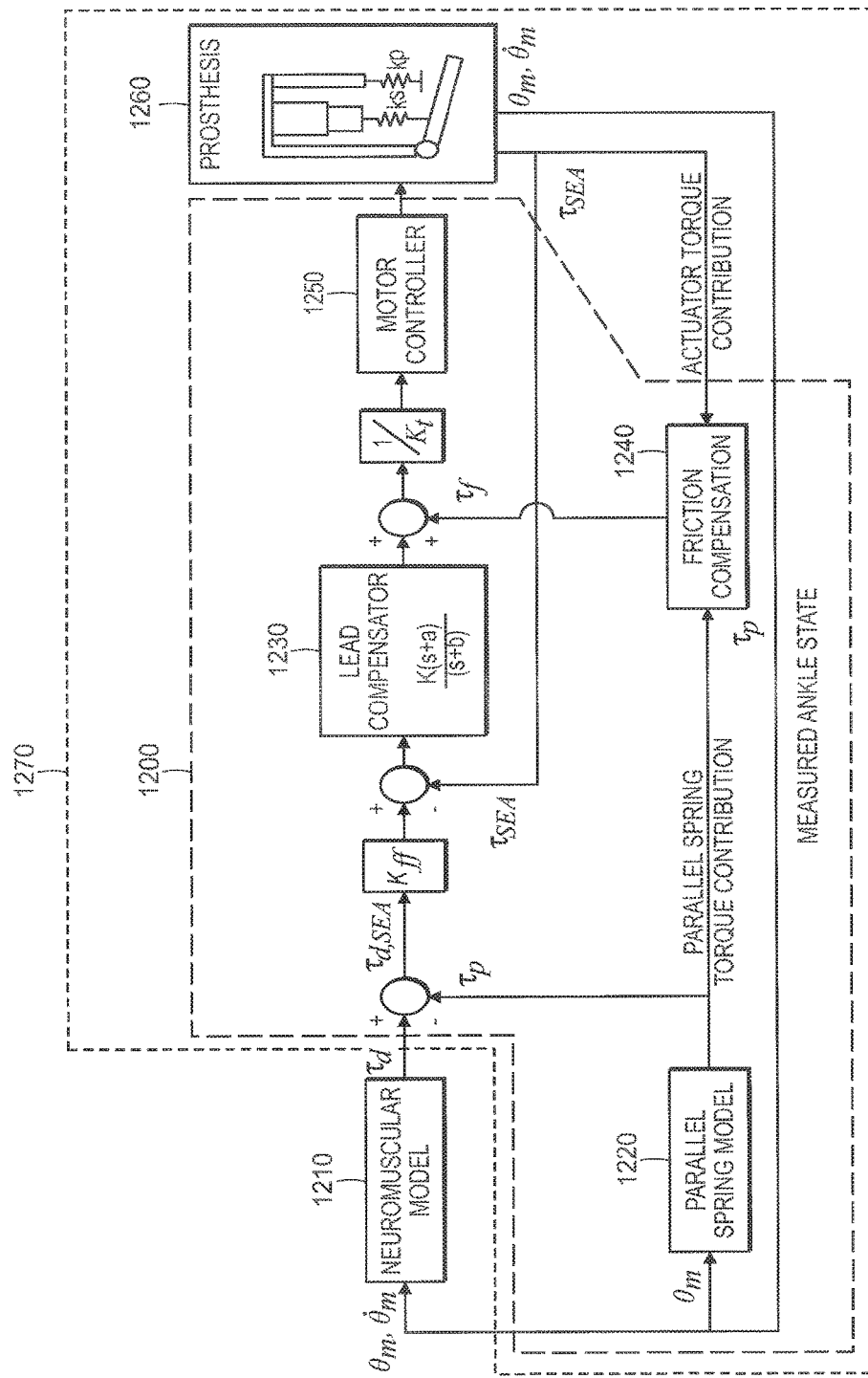
FIG. 12 is a block diagram of an exemplary embodiment of a control system for an ankle-foot prosthesis, according to one aspect of the present invention.

A block diagram of an exemplary embodiment of a control system for an ankle-foot prosthesis according to this aspect of the invention is shown in FIG. 12. Depicted in FIG. 12 are neuromuscular model 1210 and biomimetic robotic limb 1270. Robotic limb 1270 includes torque control system 1200 and robotic limb joint 1260. Torque control system 1200 includes parallel spring model 1220, lead compensator 1230, friction compensator 1240, and motor controller 1250.

The prosthesis measured ankle state, $(\theta_m, \dot{\theta}_m)$ is used to produce a torque command from the neuromuscular model, $\tau_d$. This desired ankle torque is fed through a torque control system to obtain a current command to the prosthesis actuator. The three primary components of this torque control system are the feedforward gain $K_{ff}$, lead compensator, and friction compensation term. The parallel spring contribution to prosthesis ankle torque, $\tau_p$, is subtracted from the desired ankle torque to obtain the desired actuator torque $\tau_{d,SEA}$. The closed-loop torque controller then enforces the desired actuator torque using the measured actuator torque, $\tau_{SEA}$. Finally, the friction compensation term produces an additional torque value, $\tau_f$, which is added to the output of the closed-loop torque controller.

Figure 13A:
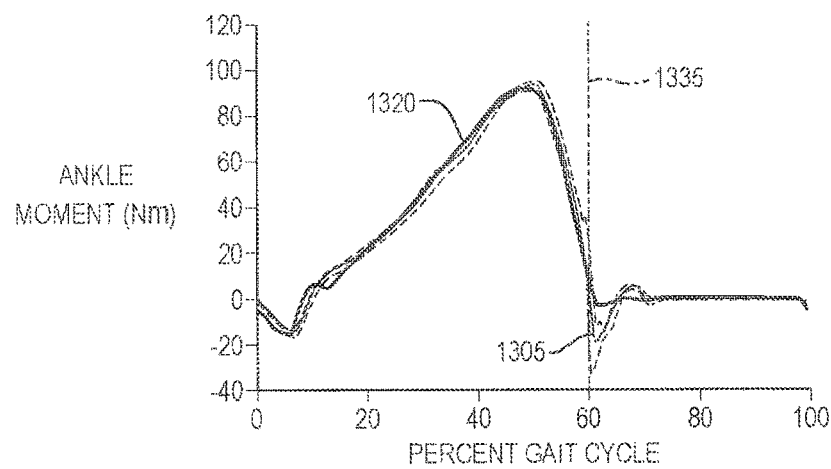
FIGS. 13A-C are exemplary plots of prosthesis torque over one complete gait cycle for three walking conditions: level-ground (FIG. 13A), ramp ascent (FIG. 13B), and ramp descent (FIG. 13C), according to one aspect of the present invention.
Figure 13B:
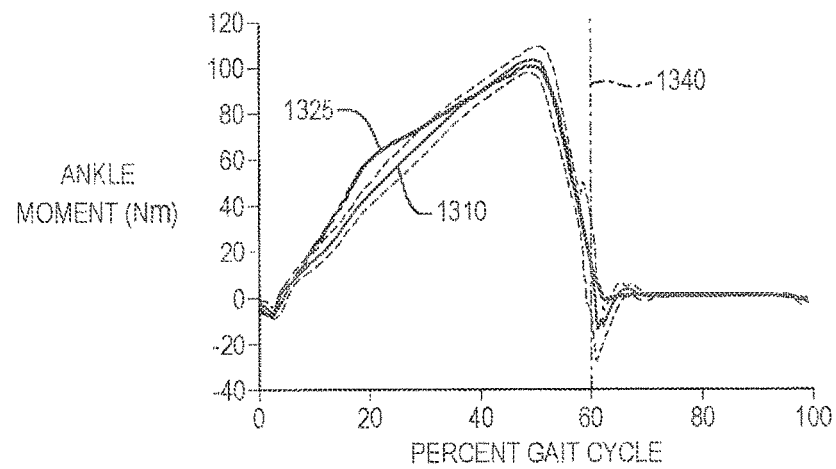
Figure 13C:
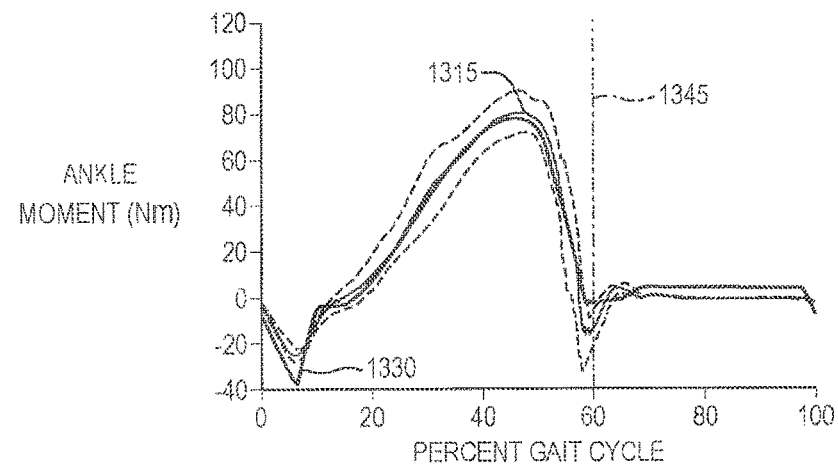

FIGS. 13A-C are plots of prosthesis torque over one complete gait cycle (heel-strike to heel-strike of the same foot) for three walking conditions: level-ground (FIG. 13A), ramp ascent (FIG. 13B), and ramp descent (FIG. 13C). Shown for each are commanded torque mean 1305, 1310, 1315 (thin line)± standard deviation (dashed lines), and prosthesis torque, as estimated using the measured SEA torque contribution and angle-based estimate of the parallel spring torque contribution 1320, 1325, 1330 (thick line). Vertical (dash-dot) lines 1335, 1340, 1345 indicate the end of the stance phase.

Figure 14A:
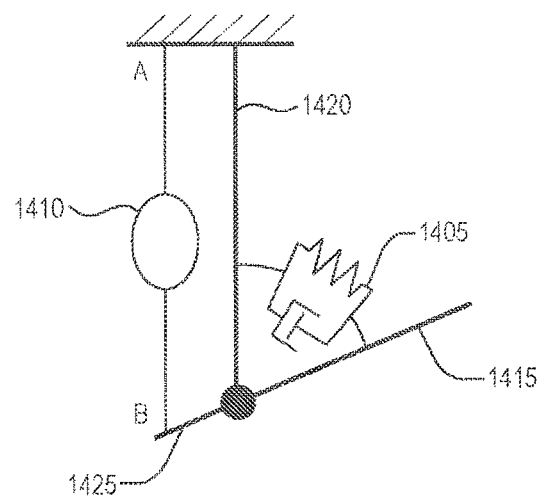
FIGS. 14A-C depict an exemplary embodiment of the musculoskeletal model as implemented on the prosthetic microcontroller, including the two-link ankle joint model (FIG. 14A), detailed Hill-type muscle model (FIG. 14B), and geometry of the muscle model skeletal attachment (FIG. 14C), according to one aspect of the present invention.
Figure 14B:
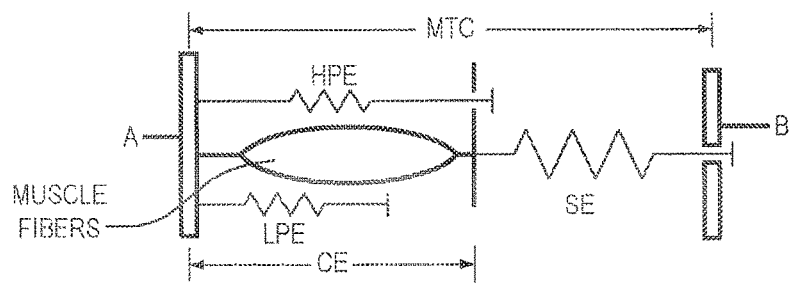
Figure 14C:
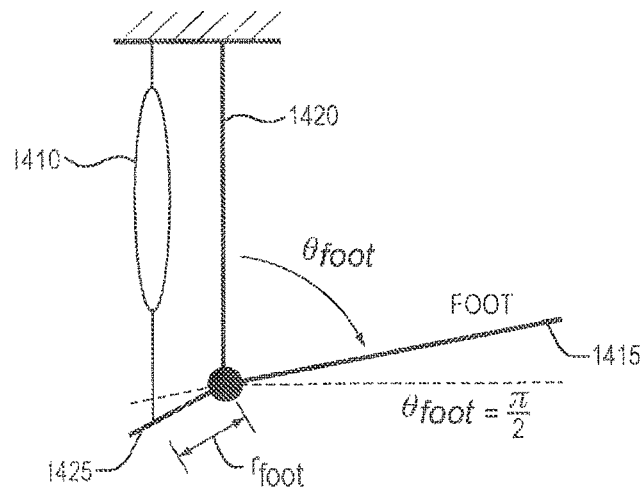

Dorsiflexor Model. FIGS. 14A-C depict an exemplary embodiment of the musculoskeletal model as implemented on the prosthetic microcontroller, including the Hill-type muscle model and spring-damper attachments to the two-link ankle joint model (FIG. 14A), detailed Hill-type muscle model (FIG. 14B), and geometry of the muscle model skeletal attachment (FIG. 14C) including the variable moment-arm implementation and angle coordinate frame for the muscle model. Depicted in FIGS. 14A and 14C are mechanical representations of dorsiflexor (spring-damper) 1405, planar flexor (MTC) 1410, foot 1415, shank 1420, and heel 1425.

The dorsiflexor in FIG. 14A is the dorsiflexor actuator. It represents the Tibialis Anterior and other biological dorsiflexor muscles. This dorsiflexor is implemented as a virtual rotary spring-damper with a set point of [θ=0, θ̇=0] and relation:

$$T_{dorsi} = K_P \theta + K_V \dot{\theta}. \qquad (1)$$

Here, $K_P$ is the spring constant, and $K_V$ is the damping constant, θ is the ankle angle and θ̇ is the ankle angular velocity. For the stance phase, the value of $K_P$ was optimized along with other muscle model parameters to best match the stance phase behavior of the biological ankle for normal level-ground walking. The damping term, $K_V$, was experimentally tuned for stance phase to 5 Nm·s/rad to prevent the forefoot from bouncing off the ground at foot-flat. Also during the stance phase, the dorsiflexor acts only to provide dorsiflexion torque, so to mimic the unidirectional property of biological muscles. Furthermore, when the torque generated by the dorsiflexor drops to zero during stance as a result of the foot becoming perpendicular to the shank, the dorsiflexor is disabled for the remainder of the stance phase. Therefore, the dorsiflexor only contributes to the torque production early in the stance phase, when human dorsiflexor muscles are known to play a significant role [J. Perry, Gait Analysis: Normal and Pathological Function, New Jersey: SLACK Inc., 1992, Chapter 4, pp. 55-57]. In the swing phase, the dorsiflexor acts as a position controller, driving the foot to the set-point [θ=0, θ̇=0]. For this, a gain of $K_P$=220 Nm/rad and damping constant of $K_V$=7 N·m·s/rad provides for quick ground clearance of the foot early in the swing phase.

Plantar Flexor Model. The virtual plantar flexor in FIGS. 14A-C comprises a muscle-tendon complex, (MTC) which represents a combination of human plantar flexor muscles. The MTC is based on S. K. Au, J. Weber, and H. Herr, "Biomechanical design of a powered ankle-foot prosthesis," Proc. IEEE Int. Conf. On Rehabilitation Robotics, Noordwijk, The Netherlands, pp. 298-303, June 2007, where it is discussed in further detail. It consists of a contractile element (CE) which models muscle fibers and a series element (SE) which models a tendon. The contractile element consists of three unidirectional components: a Hill-type muscle with a positive force feedback reflex scheme, a high-limit parallel elasticity, and a low-limit, or buffer, parallel elasticity. In series with the contractile element is the series element, which is a nonlinear, unidirectional spring representing the Achilles tendon. The attachment geometry of the muscle-tendon complex to the ankle joint model is nonlinear, complicating the calculation of torques resulting from the actuator force.

Plantar Flexor Series Elastic Element. The series elastic element (SE) operates as a tendon in series with the muscle contractile element as in [H. Geyer, A. Seyfarth, R. Blickhan, "Positive force feedback in bouncing gaits?," Proc. R Society. Lond. B 270, pp. 2173-2183, 2003]. Taking ε as the tendon strain defined as:

$$\varepsilon = \frac{l_{SE} - l_{slack}}{l_{slack}}, \qquad (2)$$

where $l_{SE}$ is the length of the series element and $l_{slack}$ is its rest length, the series element is specified to be a nonlinear spring described by H. Geyer, A. Seyfarth, R. Blickhan, "Positive force feedback in bouncing gaits?," Proc. R Society. Lond. B 270, pp. 2173-2183, 2003:

$$F_{SE} = \begin{cases} F_{max}\left(\frac{\varepsilon}{\varepsilon_{ref}}\right)^2, & \varepsilon > 0 \\ 0, & \varepsilon \leq 0 \end{cases}, \qquad (3)$$

where $F_{max}$ is the maximum isometric force that the muscle can exert. Following H. Geyer, A. Seyfarth, R. Blickhan, "Positive force feedback in bouncing gaits?," Proc. R Society. Lond. B 270, pp. 2173-2183, 2003, this quadratic form was used as an approximation of the commonly-modeled piecewise exponential-linear tendon stiffness curve. This approximation was made so to reduce the number of model parameters.

Plantar Flexor Contractile Element. The contractile element (CE) of the plantar flexor virtual actuator, FIG. 14B, is a Hill-type muscle model with a positive force feedback reflex scheme. It includes active muscle fibers to generate force, and two parallel elastic components, as in H. Geyer, H. Herr, "A muscle-reflex model that encodes principles of legged mechanics predicts human walking dynamics and muscle activities," (Submitted for publication). The Hill-type muscle fibers exert a unidirectional force. This force is a function of the muscle fiber length, $l_{CE}$, velocity, $v_{CE}$, and muscle activation, A. The resulting force, $F_{MF}$ is, as in H. Geyer, A. Seyfarth, R. Blickhan, "Positive force feedback in bouncing gaits?," Proc. R Society. Lond. B 270, pp. 2173-2183, 2003, given by:

$$F_{MF}(l_{CE}, v_{CE}, A) = F_{max} f_L(l_{CE}) f_V(v_{CE}) A. \qquad (4)$$

The force-length relationship, $f_L(l_{CE})$, of the Hill-type muscle is a bell-shaped curve given by:

$$f_L(l_{CE}) = \exp\left[c\left|\frac{l_{CE} - l_{opt}}{l_{opt} w}\right|^3\right], \qquad (5)$$

where, $l_{opt}$ is the contractile element length, $l_{CE}$, at which the muscle can provide the maximum isometric force, $F_{max}$. The parameter w is the width of the bell-shaped curve, and the parameter c describes the curve's magnitude near the extremes of the bell, where:

$$f_L(l_{CE} = (1 \pm w) l_{opt}) = \exp(c). \qquad (6)$$

The force-velocity relationship, $f_v(v_{CE})$, of the CE is the Hill equation:

$$f_V(v_{CE}) = \begin{cases} \dfrac{v_{max} - v_{CE}}{v_{max} + v_{CE}}, & v_{CE} < 0 \\ N + (N-1)\dfrac{v_{max} + v_{CE}}{7.56Kv_{CE} - Kv_{CE}}, & v_{CE} \geq 0 \end{cases} \quad (7)$$

where $v_{max} < 0$ is the maximum contractile velocity of the muscle, $v_{CE}$ is the fiber contraction velocity, K is the curvature constant, and N defines the dimensionless muscle force (normalized by $F_{max}$) such that $$N = f_V(v_{CE} = -v_{max}). \quad (8)$$

Following H. Geyer, H. Herr, "A muscle-reflex model that encodes principles of legged mechanics predicts human walking dynamics and muscle activities," (Submitted for publication), the force-length relationship for the high-limit parallel elasticity (HPE), set in parallel with the CE, is given by:

$$F_{HPE}(l_{CE}) = \begin{cases} F_{max}\left(\dfrac{l_{CE} - l_{opt}}{l_{opt}w}\right)^2, & l_{CE} > l_{opt} \\ 0, & \text{otherwise} \end{cases} \quad (9)$$

A low-limit, buffer parallel elasticity (LPE) is also included, based on H. Geyer, H. Herr, "A muscle-reflex model that encodes principles of legged mechanics predicts human walking dynamics and muscle activities," (Submitted for publication). This was given the form of the nonlinear spring:

$$F_{LPE}(l_{CE}) = \begin{cases} F_{max}\dfrac{\left[\dfrac{(l_{CE} - l_{opt}(1-w))}{l_{opt}}\right]^2}{(w/2)}, & l_{CE} \leq l_{opt}(1-w) \\ 0, & \text{otherwise} \end{cases} \quad (10)$$

Therefore, the total plantar flexor force is described by:

$$F_{CE} = F_{MF}(l_{CE}, v_{CE}, A) + F_{HPE} - F_{LPE}. \quad (11)$$

Where $F_{CE}$ is the force developed by the contractile element. Since the CE and SE are in series, the following equation holds: $F_{CE} = F_{SE} = F_{MTC}$.

Figure 15:
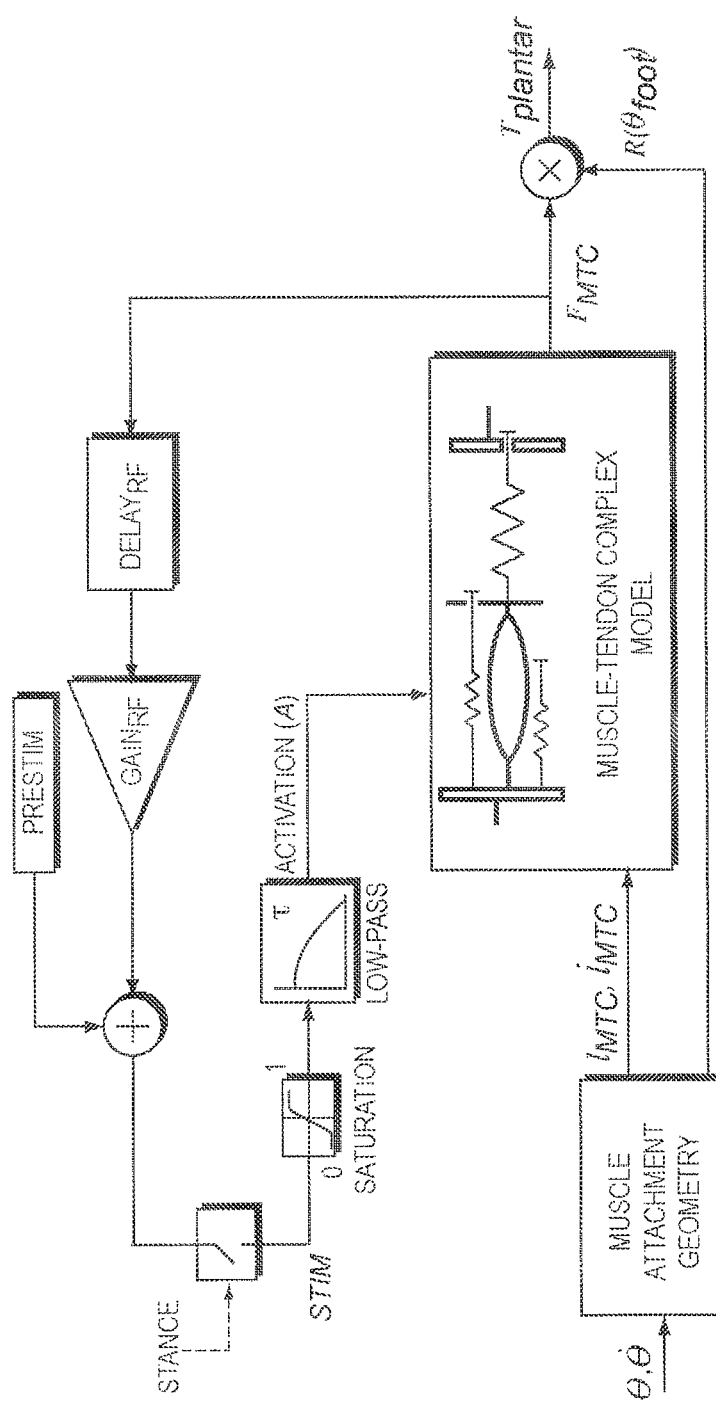
FIG. 15 depicts an exemplary embodiment of a reflex scheme for the virtual plantar flexor muscle, including the relationship among ankle angle, muscle force, and the plantar flexor component of ankle torque, according to one aspect of the present invention.

Reflex Scheme. The contractile element activation, A, is generated using the positive-force feedback reflex scheme shown in FIG. 15, as in [H. Geyer, H. Herr, "A muscle-reflex model that encodes principles of legged mechanics predicts human walking dynamics and muscle activities," (Submitted for publication); H. Geyer, A. Seyfarth, R. Blickhan, "Positive force feedback in bouncing gaits?," Proc. R Society. Lond. B 270, pp. 2173-2183, 2003]. FIG. 15 depicts an exemplary embodiment of a reflex scheme for the virtual plantar flexor muscle, including the relationship among ankle angle, muscle force, and the plantar flexor component of ankle torque.

As depicted in FIG. 15, this feedback loop includes a stance phase switch for disabling the plantar flexor force development during the swing phase. During stance, the plantar flexor force, $F_{MTC}$, is multiplied by a reflex gain $Gain_{RF}$, delayed by $Delay_{RF}$ and added to an offset stimulation, PRESTIM to obtain the neural stimulation signal. The stimulation is constrained to range from 0 to 1, and is low-pass filtered with time constant T to simulate the muscle excitation-contraction coupling. The resulting signal is used as activation in equation (4) with an initial value of PreA. In addition, a suppression gain, $Gain_{SUPP}$, following H. Geyer, H. Herr, "A muscle-reflex model that encodes principles of legged mechanics predicts human walking dynamics and muscle activities," (Submitted for publication), was implemented to help prevent the two actuators from fighting each other during stance. Here, the torque generated by the dorsiflexor is reduced by either $Gain_{SUPP} \cdot F_{MTC}$ or until its value drops to zero.

Plantar Flexor Geometry and Implementation. Within the muscle model framework, the ankle angle, $\theta_{foot}$, is defined as shown in FIG. 14C. Using this angle as the input to the model, the length of the muscle-tendon complex is calculated as in H. Geyer, H. Herr, "A muscle-reflex model that encodes principles of legged mechanics predicts human walking dynamics and muscle activities," (Submitted for publication) by:

$$l_{MTC} = r_{foot}\rho(\sin(\phi_{ref} - \phi_{max}) - \sin(\theta_{foot} - \phi_{max})) + l_{slack} + l_{opt}. \quad (12)$$

where $\rho$ is a scaling factor representing the pennation angle of the muscle fibers, and $\phi_{ref}$ is the ankle angle at which $l_{CE} = l_{op}$, under no load.

The fiber length, $l_{CE}$ can be computed using $l_{CE} = l_{MTC} - l_{SE}$, where $l_{SE}$ is obtained from the inverse of (3) given the current value of $F_{CE} = F_{SE} = F_{MTC}$ from the muscle dynamics. The fiber contraction velocity, $v_{CE}$, can then be obtained via differentiation. This creates a first order differential equation governed by the dynamics of the neuromuscular model. This equation can be solved for $F_{MTC}$ given the time history of $\theta_{foot}$ and initial condition. However, since integration is computationally more robust than differentiation, an integral form of this implementation was used to solve for $F_{MTC}$, as described in H. Geyer, H. Herr, "A muscle-reflex model that encodes principles of legged mechanics predicts human walking dynamics and muscle activities," (Submitted for publication).

Given the attachment radius, $r_{foot}$, and the angle, $\phi_{max}$, at which maximum muscle-tendon moment arm is realized, the relationship between $F_{MTC}$ and the resulting plantar flexor contribution to ankle torque, $T_{plantar}$, is given by $$T_{plantar} = F_{MTC}\cos(\theta_{foot} - \phi_{max})r_{foot} = F_{MTC} \cdot R(\theta_{foot}) \quad (13)$$

where $R(\theta_{root})$ is a variable moment arm resulting from the muscle attachment to the ankle joint model. This relationship is shown graphically in FIG. 15. Hence, the plantar flexor model can ultimately be treated as a dynamical system linking a single input, $\theta_{foot}$, to a single output, $T_{plantar}$.

Neuromuscular Model Parameter Determination. The plantar flexor model is a lumped representation of all of the biological plantar flexor muscles. Likewise, the dorsiflexor represents all biological dorsiflexor muscles. In this work, joint and torque measurements were taken only at the ankle joint. As a result, the state of multi-articular muscles, such as the gastrocnemius, could not be accurately estimated. Therefore the plantar flexor was based upon the dominant monarticular plantar flexor in humans, the Soleus. Therefore, the majority of the plantar flexor parameters values are those reported in H. Geyer, H. Herr, "A muscle-reflex model that encodes principles of legged mechanics predicts human walking dynamics and muscle activities," (Submitted for publication) for the Soleus muscle. Some parameters of the plantar flexor, as well as those for the dorsiflexor, however, were expected to either have been significantly affected by the lumped models, or were not well known from biology. These six parameters were fitted using a combination of a Genetic Algorithm and gradient descent to enable the neuromuscular model to best match the walking data of an intact subject.

Non-Optimized Parameter Values are shown in Table 6.

TABLE 6

| | | | |
|---|---|---|---|
| $l_{opt}$ [m] | 0.04 | w | 0.56 |
| $l_{slack}$ [m] | 0.26 | c | ln(0.05) |
| $v_{max}$ [$l_{opt}$/s] | 6.0 | N | 1.5 |
| $\varepsilon_{ref}$ | 0.04 | K | 5 |
| PreA | 0.01 | ρ | 0.5 |
| T [s] | 0.01 | $r_{foot}$ [m] | 0.05 |
| PreSTIM | 0.01 | Delay$_{RF}$ [s] | 0.02 |

Non-amputee Subject Data Collection. Kinetic and kinematic walking data were collected at the Gait Laboratory of Spaulding Rehabilitation Hospital, Harvard Medical School, in a study approved by the Spaulding committee on the Use of Humans as Experimental Subjects [H. Herr, M. Popovic, "Angular momentum in human walking," The Journal of Experimental Biology, Vol. 211, pp 487-481, 2008]. A healthy adult male (81.9 kg) was asked to walk at slow walking speed across a 10 m walkway in the motion capture laboratory after informed consent was given.

The motion-capture was performed using a VICON 512 motion-capture system with eight infrared cameras. Reflective markers were placed at 33 locations on the subject's body in order to allow the infrared cameras to track said locations during the trials. The cameras were operated at 120 Hz and were able to track a given marker to within approximately 1 mm. The markers were placed at the following bony landmarks for tracking the lower body: bilateral anterior superior iliac spines, posterior superior iliac spines, lateral femoral condyles, lateral malleoli, forefeet and heels. Wands were placed over the tibia and femur, and markers were attached to the wands over the mid-shaft of the tibia and the mid-femur. Markers were also placed on the upper body at the following sites: sternum, clavicle, C7 and T10 vertebrae, head, and bilaterally on the shoulder, elbow, and wrist joints.

Ground reaction forces were measured using two staggered force plates (model no. 2222 or OR6-5-1, by Advanced Mechanical Technology Inc., Watertown, Mass., USA) which were incorporated into the walkway. The precision of these force plates measuring ground reaction force and center of pressure is approximately 0.1 N and 2 mm respectively. The force plate data was collected at 1080 Hz and synchronized with the VICON motion capture data. Joint torques were calculated from the ground reaction forces and joint kinematics using a modified version of a standard inverse dynamics model. Vicon Bodybuilder, by Oxford Metrics, UK was used to perform the inverse dynamics calculations.

Six trials were obtained for a slow level-ground walking speed (1.0 m/s mean) and a single trial was used to represent the target ankle and torque trajectories for this walking condition. The end of the stance phase was defined as the point in time when the joint torque first dropped to zero after the peak torque was reached in the gait cycle. This event occurred at 67% gait-cycle for the selected trial.

Figure 16A:
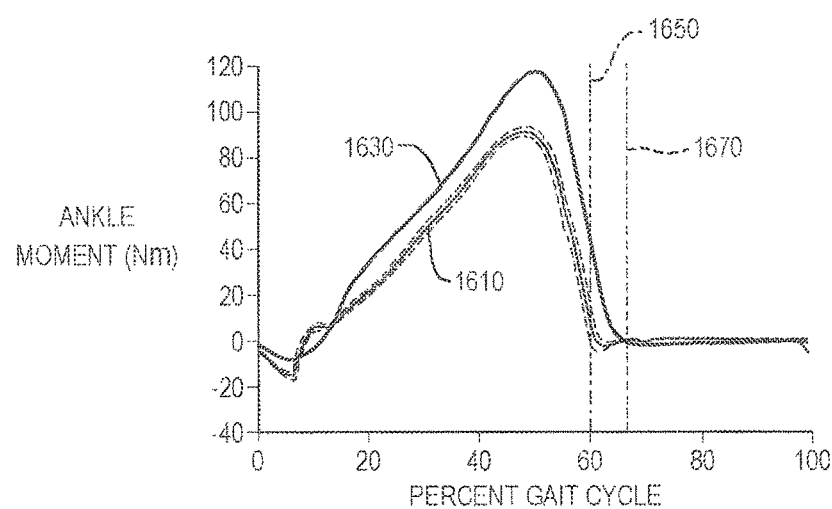
FIGS. 16A and 16B depict prosthesis-measured torque and angle trajectories during trials with an amputee subject compared to those of the biological ankle of a weight and height-matched subject with intact limbs, including ankle torque and ankle angle, respectively.
Figure 16B:
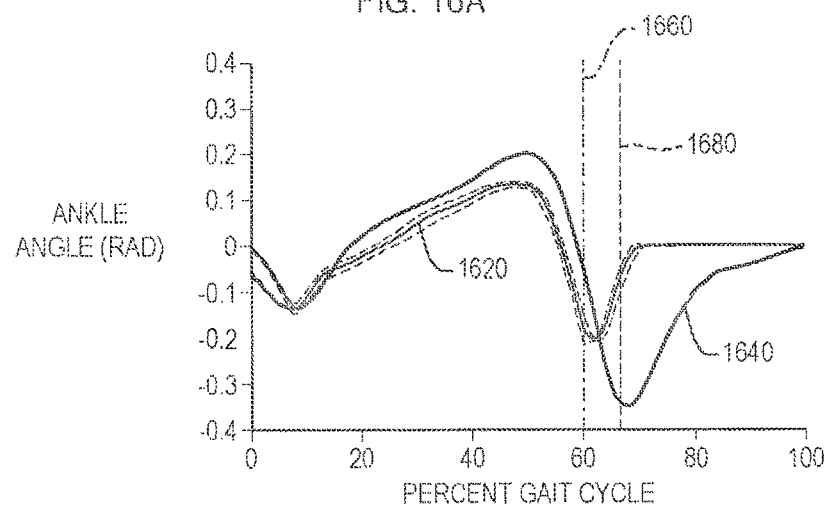

FIGS. 16A and 16B depict prosthesis-measured torque and angle trajectories during trials with an amputee subject compared to those of the biological ankle of a weight and height-matched subject with intact limbs. Shown in FIGS. 16A and 16B are ankle torque (FIG. 16A) and ankle angle (FIG. 16B) over a level-ground gait cycle from heel-strike (0% Cycle) to heel-strike of the same foot (100% Cycle). Plotted in FIGS. 16A and 16B are mean 1610, 1620 (thin line)± one standard deviation (dashed lines) for the prosthesis measured torque and angle profiles resulting from the neuromuscular-model control, and the ankle biomechanics 1630, 1640 (thick line) for a gait cycle of the weight and height-matched subject with intact limbs at the same walking speed (1 m/sec). Vertical lines indicate the average time of the beginning of swing phase 1650, 1660 (thin dash-dot line) for the prosthesis gait cycles and the beginning of the swing phase 1670, 1680 (thick dash-dot line) of the biological ankle.

Fitting of Model Parameters to Experimental Data via Optimization. The following parameters were chosen for tuning: $F_{max}$, $Gain_{FB}$, $Gain_{SUPP}$, $\phi_{ref}$, and $\phi_{max}$. The goal of the parameter tuning was to find the parameter set that would enable the neuromuscular model to best match a biological ankle torque trajectory for a particular walking condition, given the corresponding biological ankle angle trajectory as input to the model. The cost function for the optimization was defined as the squared error between the biologic and model torque profiles during the stance phase, given the biological ankle angle trajectory, i.e.:

$$\text{Cost} = \sum_{t \in STANCE} (T_m(t) - T_{bio}(t))^2. \quad (14)$$

where $T_m$ is the torque output of the model, and $T_{bio}$ is the biological ankle torque.

A Genetic Algorithm optimization was chosen to perform the initial search for optimal parameter values, and a direct search was included to pinpoint the optimal parameter set. The Genetic-Algorithm tool in Matlab was used to implement both optimization methods. The level-ground human walking data at the selected 1.0 m/s walking speed was used to provide the reference behavior for the optimization. The allowable range for each of the optimization parameters are shown in Table 7.

TABLE 7

Optimization Parameter Ranges

| Parameter (Units) | Minimum Value | Maximum Value |
|---|---|---|
| $F_{max}$ (N) | 3000 | 7000 |
| $Gain_{FB}$ | 0.6 | 1.5 |
| $K_P$ (N · m/rad) | 20 | 250 |
| $Gain_{SUPP}$ | 0 | 5 |
| $\phi_{ref}$ (rad) | 0.52 | 2.09 |
| $\phi_{max}$ (rad) | 1.40 | 2.44 |

The initial population was chosen by the optimizer. The parameter values obtained from the parameter optimization are shown in Table 8.

TABLE 8

Fitted Values of Neuromuscular Model Parameters

| | |
|---|---|
| $F_{max}$ (N) | 3377 |
| $Gain_{FB}$ | 1.22 |
| $K_P$ (N · m/rad) | 72.9 |
| $Gain_{SUPP}$ | 0 |
| $\phi_{ref}$ (rad) | 1.49 |
| $\phi_{max}$ (rad) | 1.95 |

Results of the parameter optimization. As a verification of the optimization effectiveness, the optimization was run with the final parameters using the biological ankle angle profile as input to the neuromuscular model. A comparison of the resulting torque profile to the biologic torque profile is shown in FIG. 17.

Figure 17:
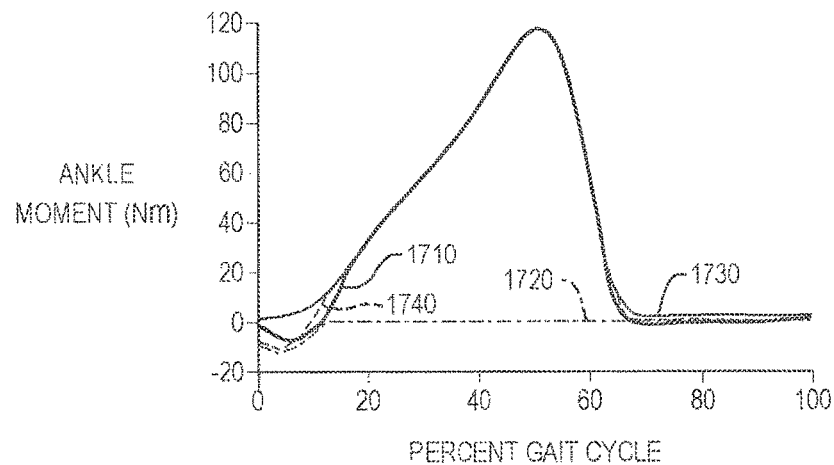
FIG. 17 is a comparison of the torque profile after parameter optimization to the biologic torque profile, according to one aspect of the present invention.

As shown in FIG. 17, a comparison of the ankle moment profile from the intact biological ankle to that of the neuromuscular model with the biological ankle angle profile as the input and with optimized parameter values, are biological ankle moment (grey line) 1710, modeled dorsiflexor component (dash-dot line) 1720, modeled plantar flexor muscle component (thin line) 1730, and total neuromuscular model (plantar flexor and dorsiflexor) moment (dashed line) 1740. The neuromuscular model ankle moment matches the biological ankle moment almost exactly for most of the gait cycle.

Low-Level Torque Control. The physical torque actually produced at the ankle joint during stance phase is from the combined actions of the parallel spring and the motorized drive train. The rotary parallel spring stiffness is approximately linear in the range of operation, with a spring stiffness of 500 N·m/rad. Using this spring constant, the parallel spring contribution is predicted and subtracted from the desired ankle torque. The remaining torque must be produced by the motorized drive train.

The performance of the motorized drive train is improved by use of lead compensation, friction compensation and feed-forward techniques, as shown in FIG. 12. Experimental investigations of the open loop drive train dynamics were performed and used to implement these improvements [M. Eilenberg, "A Neuromuscular-Model Based Control Strategy for Powered Ankle-Foot Prostheses," Master's Thesis, Massachusetts Institute of Technology, Cambridge, Mass., 2009]. The output torque versus commanded torque for level-ground walking, ramp ascent, and ramp descent is shown in FIGS. 13A-C. The prosthesis output torque was estimated using the strain gauge on the series spring for the SEA torque contribution, and the ankle angle-based parallel spring torque estimate for the parallel spring torque contribution.

Clinical Evaluation. The prosthesis was placed on the right leg of a healthy, active, 75 kg transtibial amputee. The subject was allowed time to walk on the prosthesis for natural adjustment. The wireless link to the prosthesis was used to record the walking data from these trials. During the level-ground walking trials, the subject was asked to walk across a 10 m long path. The target intended walking speed was set to 1.0 m/s to match that of the intact subject. The subject began walking approximately 5 m from the beginning of the pathway, and stopped walking approximately 3 m past the end of the path. Markers on the ground were used to note the beginning and end of the 10 m path. A stopwatch was used to verify the average walking speed for each trial by noting when the subject's center of mass passed over each of the markers. A total of 10 trials were captured. Trials with walking speeds within 5% of the target speeds were used for processing, resulting in 45 gait cycles. The subject was next asked to walk up an 11-degree, 2 m long incline at a self-selected speed. The subject started on level-ground approximately 2 m from the start of the incline and stopped approximately 1 m past the incline on a platform for 10 ramp-ascent trials. This same path was then navigated in reverse for 12 ramp-descent trials.

Data Analysis. The first three and last three gait cycles of the level-ground trials were assumed to be transients, and were therefore ignored. Each of the remaining gait cycles were re-sampled to span 1000 data points. Mean and standard-deviation trajectories were computed from the resulting data. For both ramp ascent and descent, the last step on the ramp was used as the representative gait cycle. Each selected gait cycle was re-sampled and averaged in the same manner as described for the level-ground trials.

The net work was calculated for each individual gait cycle by numerically integrating ankle torque over ankle angle from heel-strike to toe-off. Here the swing phase was ignored for the net work calculations. The average net work for each walking condition was then computed from the individual gait cycle net work values.

Results. Torque Tracking. A precondition of the present experiments was the ability of the ankle-foot prosthesis to actually produce the torques and speeds that would be commanded by the neuromuscular controller. This ability is demonstrated in FIGS. 13A-C, illustrating commanded torque versus measured output torque for level-ground walking, ramp ascent, and ramp descent.

Adaptation to Ground Slope. The evaluation of ground slope adaptation of the neuromuscular-model controlled prosthesis was confirmed by the clinical trial data of FIGS. 9a-9c. The numerically integrated data of those trials gave net work values (work loop areas) as follows:

| Level-Ground | 5.4 ± 0.5 Joules |
|---|---|
| Ramp Ascent | 12.5 ± 0.6 Joules |
| Ramp Descent | 0.1 ± 1.7 Joules |

Comparison to a Biological Ankle. The purpose of this neuromuscular model is to represent the inherent dynamics of the human ankle-foot complex in a useful way. Therefore, one may evaluate the resulting prosthesis controller based upon its ability to mimic the human behavior. FIGS. 16A and 16B, discussed previously, show the level-ground walking torque and angle profiles from the prosthesis along with those of a weight and height-matched subject with intact limbs.

Figure 18A:
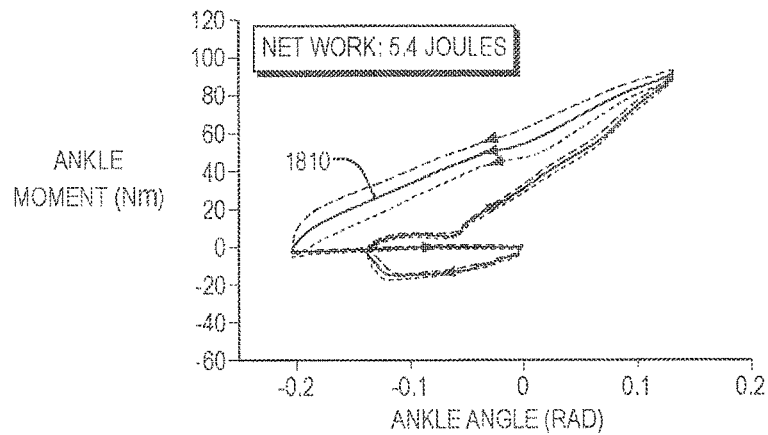
FIGS. 18A-C are plots of experimentally measured prosthesis torque-angle trajectories for an exemplary embodiment of the invention for three different walking conditions: level ground (FIG. 18A), ramp ascent (FIG. 18B), and ramp descent (FIG. 18C).
Figure 18B:
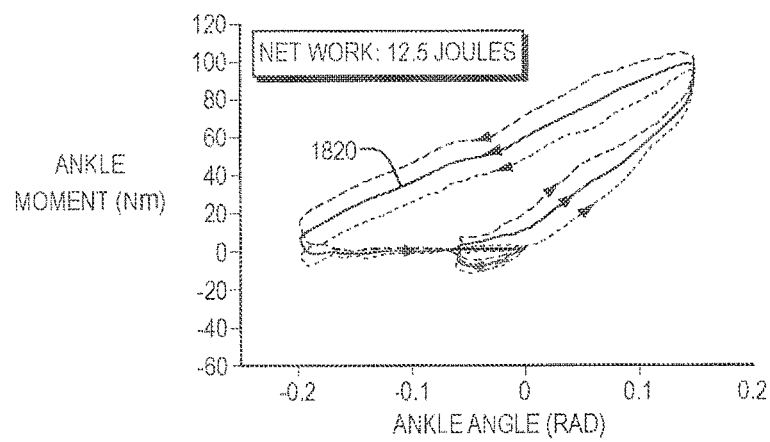
Figure 18C:
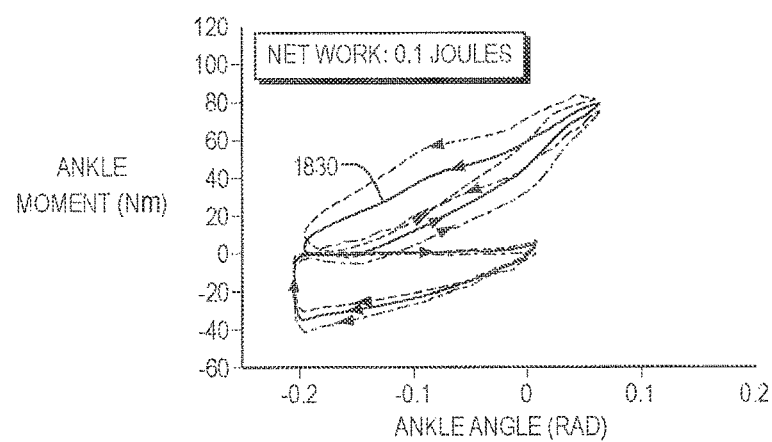

FIGS. 18A-C are plots of measured prosthesis torque-angle trajectories for three different walking conditions: level ground (FIG. 18A), ramp ascent (FIG. 18B), and ramp descent (FIG. 18C). Shown in FIGS. 18A-C, are mean 1810, 1820, 1830± one standard deviation. Arrows indicate forward propagation in time. The average prosthesis net work increases with increasing ground slope. This result is consistent with human ankle data from the literature [A. S. McIntosh, K. T. Beatty, L. N. Dwan, and D. R. Vickers, "Gait dynamics on an inclined walkway," Journal of Biomechanics, Vol. 39, pp 2491-2502, 2006].

The measured ankle torque and ankle angle profiles of the prosthesis qualitatively match those of a comparable intact individual for level-ground walking. The differences observed are of a low order, and may reasonably be attributed to a number of factors, including atrophy and/or hypertrophy in the clinical subject's leg muscles resulting from amputation, differences in limb lengths, and perhaps the lack of a functional biarticular gastrocnemius muscle. In addition, the limited range of the prosthetic angle sensor prohibited the prosthesis from reaching the full range of motion of the intact ankle.

Ground Slope Adaptation. The neuromuscular control presented here exhibits an inherent adaptation to ground slope without explicit sensing of terrain. The increased ankle net work during ramp ascent, and the decreased ankle net work during ramp descent, as compared to that of level ground walking, is consistent with the behavior of an intact human ankle under the same conditions, according to data from [A. S. McIntosh, K. T. Beatty, L. N. Dwan, and D. R. Vickers, "Gait dynamics on an inclined walkway," Journal of Biomechanics, Vol. 39, pp 2491-2502, 2006]. This variation of stance-phase positive net work across walking conditions indicates a slope-adaptive behavior that is emergent of the neuromuscular model. The ability of the neuromuscular model to produce these biomimetic changes in behavior suggests that the model embodies an important characteristic of the human plantar flexor muscles. In addition, it is anticipated that the model has the potential for speed adaptation. In an attempt to move faster, the wearer may push harder on the prosthesis. This additional force could cause the modeled reflex to command higher virtual muscle forces, resulting in greater energy output, and hence higher walking speeds.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the Appl. of the principles of the present invention. Other arrangements, methods, modifications, and substitutions by one of ordinary skill in the art are therefore also considered to be within the scope of the present invention, which is not to be limited except by the claims that follow.

What is claimed is:

1. A method for controlling at least one robotic limb joint of a robotic limb, the method comprising the steps of:
providing a neuromuscular model including a muscle model, a muscle geometry, and reflex control equations;
receiving feedback data relating to a measured state of the robotic limb, the robotic limb being a powered prosthesis, orthosis, or exoskeleton;
using the feedback data, the muscle model, the muscle geometry, and the reflex control equations of the neuromuscular model, to determine at least one torque command to be applied to the at least one robotic limb joint; and
applying the at least one torque command to the at least one robotic limb joint.

2. The method of claim 1, further including receiving the at least one torque command from the neuromuscular model with a torque control system, and wherein the at least one torque command is applied by the torque control system.

3. The method of claim 2, wherein the robotic limb includes at least one sensor mounted to the robotic limb, and the feedback data is provided by the at least one sensor mounted to the robotic limb.

4. The method of claim 3, wherein the neuromuscular model and the torque control system are configured to control the robotic limb, wherein the robotic limb is a robotic leg, and wherein the method further includes, with a finite state machine synchronized to a leg gait cycle, receiving the feedback data from the at least one sensor and determining a gait phase of the robotic leg using the feedback data received.

5. The method of claim 4, wherein the neuromuscular model and the torque control system are configured to control the robotic leg, and wherein the robotic leg comprises an ankle joint.

6. The method of claim 5, wherein the robotic leg further comprises a knee joint.

7. The method of claim 6, wherein the robotic leg further comprises a hip joint.

8. The method of claim 4, wherein the neuromuscular model and the torque control system are configured to control the robotic leg, and wherein the robotic leg comprises a knee joint.

9. The method of claim 3, wherein the at least one sensor is an angular joint displacement and velocity sensor, a torque sensor, or an inertial measurement unit.

10. The method of claim 3, wherein the feedback data includes a joint angle and a joint angular velocity measured by the at least one sensor.

11. The method of claim 10, wherein the muscle model comprises a contractile element and a series-elastic element arranged in a muscle tendon unit.

12. The method of claim 11, wherein the reflex control equations are configured in a local feedback loop, and further including, with the reflex control equations, receiving muscle force feedback from the muscle model and providing the stimulation input to the muscle model.

13. The method of claim 12, wherein the muscle force feedback is positive force feedback.

14. The method of claim 12, wherein the reflex control equations are configured to mimic a stretch reflex of an intact human muscle.

15. The method of claim 10, further including using muscle tendon lever arm and muscle tendon length equations of the muscle geometry, in combination with the measured joint angle, to determine a muscle moment arm value and a muscle tendon length value.

16. The method of claim 15, further including, with the muscle model, determining muscle force using the muscle tendon length value and a stimulation input.

17. The method of claim 2, wherein the torque control system includes a feed forward gain, a lead compensator and a friction compensator to adapt the at least one torque command and thereby obtain at least one current command.

18. The method of claim 17, wherein the torque control system further includes a motor controller, and wherein applying the at least one torque command includes driving an actuator of the at least one robotic limb joint with the at least one current command using the motor controller.

19. The method of claim 18, wherein the torque control system further includes a parallel spring model.

* * * * *